US010559221B2

(12) United States Patent
Martucci et al.

(10) Patent No.: US 10,559,221 B2
(45) Date of Patent: Feb. 11, 2020

(54) PROCESSOR-IMPLEMENTED SYSTEMS AND METHODS FOR ENHANCING COGNITIVE ABILITIES BY PERSONALIZING COGNITIVE TRAINING REGIMENS

(71) Applicant: Akili Interactive Labs, Inc., Boston, MA (US)

(72) Inventors: W. E. Martucci, Westwood, MA (US); Adam Piper, Petaluma, CA (US); Matthew Omernick, Larkspur, CA (US); Adam Gazzaley, San Francisco, CA (US); Eric Elenko, Boston, MA (US); Ketki Karanam, Newton, MA (US)

(73) Assignee: Akili Interactive Labs, Inc., Boston, MA (US)

( * ) Notice: Subject to any disclaimer, the term of this patent is extended or adjusted under 35 U.S.C. 154(b) by 497 days.

(21) Appl. No.: 15/312,557

(22) PCT Filed: May 20, 2015

(86) PCT No.: PCT/US2015/031780
§ 371 (c)(1),
(2) Date: Nov. 18, 2016

(87) PCT Pub. No.: WO2015/179522
PCT Pub. Date: Nov. 26, 2015

(65) Prior Publication Data
US 2017/0098385 A1    Apr. 6, 2017

Related U.S. Application Data

(60) Provisional application No. 62/001,141, filed on May 21, 2014.

(51) Int. Cl.
*G09B 19/00* (2006.01)
*A61B 5/00* (2006.01)
*G09B 5/02* (2006.01)

(52) U.S. Cl.
CPC ............ *G09B 19/00* (2013.01); *A61B 5/4088* (2013.01); *A61B 5/4848* (2013.01); *G09B 5/02* (2013.01)

(58) Field of Classification Search
CPC ........ A61B 5/4088; A61B 5/4848; A61B 5/00; G09B 19/00
(Continued)

(56) References Cited

U.S. PATENT DOCUMENTS 6,585,518 B1    7/2003    Jenkins et al.
8,016,416 B1    9/2011    Straus
(Continued)

FOREIGN PATENT DOCUMENTS

EP    2031572    3/2009
JP    2006503359 A    1/2006
(Continued)

OTHER PUBLICATIONS

Anguera JA et al., 2013 Nature, 501: 97-101.
(Continued)

*Primary Examiner* — Michael A Cuff
(74) *Attorney, Agent, or Firm* — Gregory Finch; Finch Palino, LLC

(57) ABSTRACT

Systems and methods are provided for the implementation of personalized cognitive training. As an example, a processor-implemented method is provided for enhancing cognitive abilities of a user by personalizing cognitive training regimens through difficulty progression. The method includes: performing a cognitive assessment of a user using a set of assessment tasks; estimating a maximal performance of the user related to the set of assessment tasks; determining a performance range based at least in part on the maximal performance of the user; dividing the performance range into a plurality of progress gates, the plurality of progress gates corresponding to a plurality of task difficulty levels; selecting a first progress gate within the performance range; generating a first set of training tasks associated with the first progress gate; and collecting the user's first training responses to the first set of training tasks.

40 Claims, 20 Drawing Sheets

(58) Field of Classification Search
USPC .......................................................... 434/238
See application file for complete search history.

(56) References Cited

U.S. PATENT DOCUMENTS

| | | | |
|---|---|---|---|
| 8,343,012 | B2 | 1/2013 | Redmann |
| 9,265,458 | B2 | 2/2016 | Stack |
| 2005/0175972 | A1 | 8/2005 | Goldman et al. |
| 2005/0199010 | A1 | 9/2005 | Coleman et al. |
| 2006/0089335 | A1 | 4/2006 | Liu et al. |
| 2007/0141541 | A1 | 6/2007 | Chan et al. |
| 2007/0299319 | A1 | 12/2007 | Chan et al. |
| 2008/0028276 | A1 | 1/2008 | Li et al. |
| 2009/0031217 | A1 | 1/2009 | Tysbo |
| 2010/0092929 | A1 | 4/2010 | Hallowell et al. |
| 2010/0094155 | A1 | 4/2010 | Prichep |
| 2010/0152249 | A1 | 6/2010 | Rasgon |
| 2010/0292545 | A1 | 11/2010 | Berka et al. |
| 2012/0088222 | A1 | 4/2012 | Considine et al. |
| 2012/0090446 | A1 | 4/2012 | Moreno |
| 2012/0108997 | A1 | 5/2012 | Guan et al. |
| 2012/0196257 | A1 | 8/2012 | Verghese et al. |
| 2012/0208169 | A1 | 8/2012 | Nutley et al. |
| 2012/0214143 | A1 | 8/2012 | Severson et al. |
| 2012/0258436 | A1* | 10/2012 | Lee .................. G09B 19/00 434/362 |
| 2012/0271194 | A1 | 10/2012 | MacLullich et al. |
| 2013/0091453 | A1 | 4/2013 | Kotler et al. |
| 2013/0344000 | A1* | 12/2013 | Kaplin ................ A61K 31/19 424/9.3 |
| 2014/0019059 | A1* | 1/2014 | Shankle .............. G16H 50/20 702/19 |
| 2014/0279746 | A1 | 9/2014 | De Bruin et al. |
| 2014/0370479 | A1 | 12/2014 | Gazzaley |
| 2015/0004577 | A1 | 1/2015 | Wu et al. |
| 2015/0112899 | A1* | 4/2015 | Dagum ............... A61B 5/6898 706/12 |
| 2015/0187227 | A1* | 7/2015 | Zhang ................. G09B 19/00 434/236 |
| 2015/0199010 | A1 | 7/2015 | Coleman et al. |
| 2016/0078780 | A1* | 3/2016 | Alexander ............ G09B 19/00 600/508 |
| 2016/0155355 | A1 | 6/2016 | Merzenich et al. |
| 2016/0262680 | A1 | 9/2016 | Martucci et al. |

FOREIGN PATENT DOCUMENTS

| | | |
|---|---|---|
| JP | 2014508309 A | 4/2014 |
| WO | WO-2004036499 A1 | 4/2004 |
| WO | 2012/064999 | 5/2012 |
| WO | WO-2014138925 A1 | 9/2014 |
| WO | WO-2015049234 A1 | 4/2015 |
| WO | WO-2015179522 A1 | 11/2015 |
| WO | WO-2015192021 A1 | 12/2015 |

OTHER PUBLICATIONS

Hastie, T. et al., The Elements of Statistical Learning, 2nd Edition, Springer: 2009.
International Preliminary Report on Patentability issued in PCT/US2015/031780, dated Nov. 22, 2016 (13 pages).
International Search Report and Written Opinion issued in PCT/US2015/031780, dated Aug. 19, 2015 (15 pages).
Annex to European Patent Office Communication dated Sep. 19, 2018, for Application No. 15795907.3, 5 pg.
Australian Examination Report No. 1 dated Nov. 26, 2018 for Application No. 2015264260, 3 pages.
Baniqued, et al., "Selling Points: What Cognitive Abilities are Tapped by Casual Video Games?," Acta psycholgica, (2013), vol. 142, No. 1, pp. 74-86.
Caron, "Gaming & Culture—Of gyroscopes and gaming: the tech behind the Wii MotionPlus," Aug. 26, 2008, https://arstechnica.com/gaming/2008/08/wii-motion-sensor/, pp. 1-8.
Charron, et al., Divided Representation of Concurrent Goals in the Human Frontal Lobes, Science, (Apr. 2010), vol. 328, No. 5975, pp. 360-363.
Colich, et al., "Neural Aspects of Inhibition Following Emotional Primes in Depressed Adolescents," J Clin Child Adolesc Psychol., (2016), vol. 45, No. 1, pp. 21-30.
Communication Pursuant to Article 94(3) dated Sep. 19, 2018, for Application No. 15795907.3, 2 pg.
Communication Pursuant to Rule 161(2) and 162 dated Jan. 4, 2017, for Application No. 15795907.3, 2 pg.
Search Report and Written Opinion dated Nov. 28, 2018, for Application No. PCT/US2018/00179, 18 pg.
Extended European Search Report dated Oct. 11, 2018, for Application No. 16762544.9, 11 pg.
International Search Report and Written Opinion dated Dec. 4, 2018 for International Application No. PCT/US2018/045206 (19 pages).
International Search Report and Written Opinion dated Nov. 7, 2017 for International Application No. PCT/US2017/048698 (30 pages).
International Search Report and Written Opinion dated Oct. 13, 2017 for International Application No. PCT/US2017/045385 (30 pages).
International Search Report and Written Opinion dated Sep. 29, 2017 for International Application No. PCT/US2017/042938 (21 pages).
Japanese Notice of Reasons for Rejection dated Dec. 7, 2018, for Application No. 2017-513600, 5 page.
Junco, et al. "Perceived Academic Effects of Instant Messaging Use," Computers & Education, (2011), vol. 56, pp. 370-378.
Kautz, et al., "Fostering and Measuring Skills: Improving Cognitive and Non-Cognitive Skills to Promote Lifetime Success," National Bureau of Economic Research, (Sep. 2007), 87 pages.
Laricchiuta, et al., Individual differences in response to positive and negative stimuli: endocannabinoid-based insight on approach and avoidance behaviors, Frontiers in Systems Neuroscience, (Dec. 2014), vol. 8, Article 238, 22 pages.
Mayer, et al., "Nine Ways to Reduce Cognitive Load in Multimedia Learning," Education Psychologist, (2003), vol. 38, No. 1, pp. 43-52.
Pashler, "Dual-Task Interference in Simple Tasks: Data and Theory," Psychological Bulletin, (1994), vol. 116, No. 2, pp. 220-244.
Written Opinion dated May 26, 2016, for Application No. PCT/US2016/022115, 13 pg.
Compass, "Psilocybin therapy Background and Key findings from prior published studies," Compass Pathways Powerpoint presentation, (2018), 11 pages.
Compass, Transforming mental health through psychoactive care pathways, Compass Pathways Powerpoint presentation, (Jan. 2018), 19 pages.
Rucker, et al., "Psychedelics in the treatment of unipolar mood disorders: a systematic review," Journal of Psychopharmacology, (2016), pp. 1-10.

* cited by examiner

A

| Feature | Project: EVO early version | Project: EVO with performance bounds in place | t-test (p-value) |
|---|---|---|---|
| Number of training runs analyzed | 25 | 16 | - |
| RMSD from peak: Tapping (mean ± s.d) | 2.01 ± 0.5 | 2.24 ± 0.42 | Not significant (0.14) |
| RMSD from peak: Navigation (mean ± s.d) | 4.86 ± 1.12 | 1.83 ± 0.45 | Significant (1.08 × 10⁻¹¹) |
| % positive df/dt: Tapping (mean ± s.d) | 70% ± 7% | 73% ± 6% | Not significant (0.1648) |
| % positive df/dt: Navigation (mean ± s.d) | 86% ± 4% | 83% ± 2% | Significant (0.0158) |

B

C

D

| TEST | PRE-TRAINING SCORE | POST-TRAINING SCORE | p-value |
|---|---|---|---|
| TOVA: | | | |
| IMPULSIVITY INDEX HALF2 | 1.12 ± 0.38 | 0.84 ± 0.40 | 0.005* |
| IMPULSIVITY INDEX TOTAL | 1.04 ± 0.34 | 0.89 ± 0.41 | 0.045* |
| STD. DEVIATION OF REACTION TIME | 0.78 ± 1.39 | 1.41 ± 2.18 | 0.042* |
| CANTAB: | | | |
| SWM TOTAL ERRORS | 18.8 ± 6.01 | 13.40 ± 7.46 | 0.023* |
| SWM MEDIAN TIME TO 1st RESPONSE | 16215.25 ± 4969.13 | 11769.55 ± 1441.33 | 0.009* |

SCORES EXPRESSED AS: MEAN ± STD. DEV.
*: SIGNIFICANT

Fig. 11D

PROCESSOR-IMPLEMENTED SYSTEMS AND METHODS FOR ENHANCING COGNITIVE ABILITIES BY PERSONALIZING COGNITIVE TRAINING REGIMENS

CROSS-REFERENCE TO RELATED APPLICATIONS

This application is a national stage application under 35 U.S.C. § 371 of International Application No. PCT/US2015/031780, filed on May 20, 2015, which claims the benefit of U.S. Provisional Patent Application No. 62/001,141, filed on May 21, 2014. The entire contents of the above applications, including drawings, are incorporated by reference.

BACKGROUND

Cognitive impairment is recognized as a major issue in a wide range of populations varying from ones where cognitive deficits are the major disease hallmark through normal aging. From children through the elderly, cognitive deficits can significantly impact quality of life. A number of pharmacological, medical device, and behavioral therapy approaches have been developed to target cognition in disease and healthy populations.

Cognitive training has emerged as a particularly promising approach toward improving cognition or preventing cognitive decline. Cognitive training methods have the benefits of being non-invasive, deliverable in multiple formats, and applicable across a range of participant demographics. Additionally, emerging evidence suggest that very specific cognitive training paradigms can have robust cognitive improvements in specific patient populations (Anguera J A et al., 2013 Nature, 501: 97-101). However, the general applicability of cognitive training approaches has been limited by the technical problem of low efficiency (essentially, time spent engaging in a training regimen is not actually cognitively challenging to the individual during the whole cognitive training regimen). It is recognized that cognitive training may be challenging to an individual in order for neural plasticity and cognitive improvements to occur. However, with current limitations in training protocols, some cases of cognitive training regimens may become so inefficient that an individual may spend large blocks of time executing a training protocol at a difficulty well above or well below what is suited to his/her abilities.

SUMMARY

The present disclosure describes systems and methods for the implementation of personalized cognitive training. As an example, a processor-implemented method is provided for enhancing cognitive abilities of a user by personalizing cognitive training regimens. A cognitive assessment of a user is performed using a set of assessment tasks. A maximal performance of the user related to the set of assessment tasks is estimated. A performance range is determined based at least in part on the maximal performance of the user. The performance range is divided into a plurality of progress gates corresponding to a plurality of task difficulty levels for personalizing cognitive training regimens.

As another example, a processor-implemented method is provided for enhancing cognitive abilities of a user by personalizing cognitive training regimens through difficulty progression. A progress gate corresponding to a particular task difficulty level is selected within a personalized performance range for a user (e.g., determined by a cognitive assessment). A set of training tasks associated with the progress gate are generated. The user's training responses to the set of training tasks are collected. Whether the user succeeds at the progress gate is determined based at least in part on the user's training responses. In response to the user succeeding at the progress gate, another progress gate (e.g., corresponding to a higher task difficulty level) within the performance range is selected for further cognitive training of the user.

In one embodiment, a processor-implemented method is provided for enhancing cognitive abilities of a user by personalizing cognitive training regimens through difficulty progression. The method includes: performing, using one or more data processors, a cognitive assessment of a user using a set of assessment tasks; estimating, using the one or more data processors, a maximal performance of the user related to the set of assessment tasks; and determining, using the one or more data processors, a performance range based at least in part on the maximal performance of the user. Further, the method includes: dividing, using the one or more data processors, the performance range into a plurality of progress gates, the plurality of progress gates corresponding to a plurality of task difficulty levels, data related to the performance range being stored in a data structure in a non-transitory machine-readable storage medium; selecting, using the one or more data processors, a first progress gate within the performance range; and generating, using the one or more data processors, a first set of training tasks associated with the first progress gate. The method also includes: collecting the user's first training responses to the first set of training tasks; and determining, using the one or more data processors, whether the user succeeds at the first progress gate based at least in part on the user's first training responses. The method further includes: in response to the user succeeding at the first progress gate, selecting, using the one or more data processors, a second progress gate within the performance range; generating, using the one or more data processors, a second set of training tasks associated with the second progress gate; and collecting the user's second training responses to the second set of training tasks for determining whether the user succeeds at the second progress gate.

In another embodiment, a processor-implemented method is provided for enhancing cognitive abilities of a user by personalizing cognitive training regimens through difficulty progression. The method includes: performing, using one or more data processors, an initial cognitive assessment of a user using a first set of assessment tasks; estimating, using the one or more data processors, an initial maximal performance of the user related to the first set of assessment tasks; and determining, using the one or more data processors, the initial performance range based at least in part on the initial maximal performance of the user. The method further includes: dividing, using the one or more data processors, the initial performance range into a first plurality of progress gates, the first plurality of progress gates corresponding to a first plurality of task difficulty levels, data related to the initial performance range being stored in a first data structure in a non-transitory machine-readable storage medium; selecting, using the one or more data processors, a first progress gate within the initial performance range; and generating, using the one or more data processors, a first set of training tasks associated with the first progress gate. In addition, the method includes: collecting the user's first training responses to the first set of training tasks; and determining, using the one or more data processors, whether the user succeeds at the first progress gate based at least in part on the user's first training responses. Furthermore, the method includes: in response to the user succeeding at the first progress gate, performing, using the one or more data processors, a cognitive assessment of the user using a second set of assessment tasks; estimating, using the one or more data processors, an updated maximal performance of the user related to the second set of assessment tasks; and determining, using the one or more data processors, an updated performance range based at least in part on the updated maximal performance of the user, data related to the updated performance range being stored in a second data structure in the non-transitory machine-readable storage medium; dividing, using the one or more data processors, the updated performance range into a second plurality of progress gates, the second plurality of progress gates corresponding to a second plurality of task difficulty levels; selecting, using the one or more data processors, a second progress gate within the updated performance range; generating, using the one or more data processors, a second set of training tasks associated with the second progress gate; and collecting the user's second training responses to the second set of training tasks for determining whether the user succeeds at the second progress gate.

In some embodiments, the processor-implemented method includes performing multiple training tasks and, determined by the performance on training tasks, succeeding at multiple progress gates before a new assessment is triggered. For example, prior to the selection of the first progress gate as described above, a third progress gate is selected within the initial performance range. A third set of training tasks associated with the third progress gate are generated. The user's third training responses to the third set of training tasks are collected. Whether the user succeeds at the third progress gate is determined based at least in part on the user's third training responses. The first progress gate within the initial performance range is selected in response to the user succeeding at the third progress gate, and the performance of the first set of training tasks associated with the first progress gate triggers a new assessment.

In yet another embodiment, a processor-implemented system is provided for enhancing cognitive abilities of a user by personalizing cognitive training regimens through difficulty progression. The system includes: one or more processors and one or more non-transitory machine-readable storage media. The one or more processors are configured to: perform a cognitive assessment of a user using a set of assessment tasks; estimate a maximal performance of the user related to the set of assessment tasks; determine a performance range based at least in part on the maximal performance of the user; divide the performance range into a plurality of progress gates, the plurality of progress gates corresponding to a plurality of task difficulty levels; select a first progress gate within the performance range; generate a first set of training tasks associated with the first progress gate; collect the user's first training responses to the first set of training tasks; and determine whether the user succeeds at the first progress gate based at least in part on the user's first training responses. The one or more processors are further configured to: in response to the user succeeding at the first progress gate, select a second progress gate within the performance range; generate a second set of training tasks associated with the second progress gate; and collect the user's second training responses to the second set of training tasks to determine whether the user succeeds at the second progress gate. The one or more non-transitory machine-readable storage media are configured to store data related to the first set of training tasks, data related to the second set of training tasks, and data related to the performance range.

In yet another embodiment, a processor-implemented system is provided for enhancing cognitive abilities of a user by personalizing cognitive training regimens through difficulty progression. The system includes one or more processors and one or more non-transitory machine-readable storage media. The one or more processors are configured to: perform an initial cognitive assessment of a user using a first set of assessment tasks; estimate an initial maximal performance of the user related to the first set of assessment tasks; determine the initial performance range based at least in part on the initial maximal performance of the user; divide the initial performance range into a first plurality of progress gates, the first plurality of progress gates corresponding to a first plurality of task difficulty levels; select a first progress gate within the initial performance range; generate a first set of training tasks associated with the first progress gate; collect the user's first training responses to the first set of training tasks; and determine whether the user succeeds at the first progress gate based at least in part on the user's first training responses. The one or more processors are further configured to: in response to the user succeeding at the first progress gate, perform a cognitive assessment of the user using a second set of assessment tasks; estimate an updated maximal performance of the user related to the second set of assessment tasks; determine an updated performance range based at least in part on the updated maximal performance of the user; divide the updated performance range into a second plurality of progress gates, the second plurality of progress gates corresponding to a second plurality of task difficulty levels; select a second progress gate within the updated performance range; generate a second set of training tasks associated with the second progress gate; and collect the user's second training responses to the second set of training tasks to determine whether the user succeeds at the second progress gate. The one or more non-transitory machine-readable storage media are configured to store data related to the first set of training tasks, data related to the second set of training tasks, date related to the initial performance range, and data related to the updated performance range.

In some embodiments, the processor-implemented system is configured to perform multiple training tasks and, determined by the performance on training tasks, succeeding at multiple progress gates before a new assessment is triggered. For example, the one or more processors are further configured to: prior to the selection of the first progress gate, select a third progress gate within the initial performance range; generate a third set of training tasks associated with the third progress gate; collect the user's third training responses to the third set of training tasks; determine whether the user succeeds at the third progress gate based at least in part on the user's third training responses; and select the first progress gate within the initial performance range in response to the user succeeding at the third progress gate. The performance of the first set of training tasks associated with the first progress gate triggers a new assessment.

According to one embodiment, a computer-readable medium is encoded with instructions for commanding one or more processors to execute operations of a method for enhancing cognitive abilities of a user by personalizing cognitive training regimens through difficulty progression. The method includes: performing a cognitive assessment of a user using a set of assessment tasks; estimating a maximal performance of the user related to the set of assessment tasks; determining a performance range based at least in part on the maximal performance of the user; dividing the performance range into a plurality of progress gates, the plurality of progress gates corresponding to a plurality of task difficulty levels; selecting a first progress gate within the performance range; generating a first set of training tasks associated with the first progress gate; collecting the user's first training responses to the first set of training tasks; and determining whether the user succeeds at the first progress gate based at least in part on the user's first training responses. The method further includes: in response to the user succeeding at the first progress gate, selecting a second progress gate within the performance range; generating a second set of training tasks associated with the second progress gate; and collecting the user's second training responses to the second set of training tasks for determining whether the user succeeds at the second progress gate.

According to another embodiment, a computer-readable medium is encoded with instructions for commanding one or more processors to execute operations of a method for enhancing cognitive abilities of a user by personalizing cognitive training regimens through difficulty progression. The method includes: performing an initial cognitive assessment of a user using a first set of assessment tasks; estimating an initial maximal performance of the user related to the first set of assessment tasks; determining the initial performance range based at least in part on the initial maximal performance of the user; dividing the initial performance range into a first plurality of progress gates, the first plurality of progress gates corresponding to a first plurality of task difficulty levels; selecting a first progress gate within the initial performance range; generating a first set of training tasks associated with the first progress gate; collecting the user's first training responses to the first set of training tasks; and determining whether the user succeeds at the first progress gate based at least in part on the user's first training responses. The method further includes: in response to the user succeeding at the first progress gate, performing a cognitive assessment of the user using a second set of assessment tasks; estimating an updated maximal performance of the user related to the second set of assessment tasks; determining an updated performance range based at least in part on the updated maximal performance of the user; dividing the updated performance range into a second plurality of progress gates, the second plurality of progress gates corresponding to a second plurality of task difficulty levels; selecting a second progress gate within the updated performance range; generating a second set of training tasks associated with the second progress gate; and collecting the user's second training responses to the second set of training tasks for determining whether the user succeeds at the second progress gate.

In some embodiments, the processor-implemented method includes performing multiple training tasks and, determined by the performance on training tasks, succeeding at multiple progress gates before a new assessment is triggered. For example, prior to the selection of the first progress gate as described above, a third progress gate is selected within the initial performance range. A third set of training tasks associated with the third progress gate are generated. The user's third training responses to the third set of training tasks are collected. Whether the user succeeds at the third progress gate is determined based at least in part on the user's third training responses. The first progress gate within the initial performance range is selected in response to the user succeeding at the third progress gate, and the performance of the first set of training tasks associated with the first progress gate triggers a new assessment.

According to yet another embodiment, a method is provided for enhancing a cognitive ability in a subject in need thereof, wherein said method comprises performing by the subject the processor-implemented method according to any embodiment in the present disclosure. For example, the subject's cognitive ability is assessed by a cognitive ability test, wherein the cognitive ability test is selected from the group consisting of Mini Mental State Exam, CANTAB cognitive battery, Repeatable Battery for the Assessment of Neuropsychological Status, Clinical Global Impression scales, Clinician's interview-Based Impression of Change, Severe Impairment Battery, Alzheimer's Disease Assessment Scale, Positive and Negative Syndrome Scale, Schizophrenia Cognition Rating Scale, Conners Adult ADHD Rating Scales, Hamilton Rating Scale for Depression, Hamilton Anxiety Scale, Montgomery-Asberg Depressing Rating scale, Young Mania Rating Scale, Children's Depression Rating Scale, Penn State Worry Questionnaire, Hospital Anxiety and Depression Scale, Aberrant Behavior Checklist, and Activities of Daily Living scales, General Practitioner Assessment of Cognition, Eriksen Flanker Task, Stroop Task, Intelligence quotient, Raven's Progressive Matrices, Behavior Rating Inventory of Executive Function (BRIEF), Test of Everyday Attention (and Test of Everyday Attention for Children), Test of Memory and Learning, Wisconsin Card Scoring Test, and Delis Kaplan Executive Function System.

As an example, the subject's cognitive ability is enhanced as indicated by a score improvement in a cognitive ability test, wherein the cognitive ability test is selected from the group consisting of Mini Mental State Exam, CANTAB cognitive battery, Repeatable Battery for the Assessment of Neuropsychological Status, Clinical Global Impression scales, Clinician's interview-Based Impression of Change, Severe Impairment Battery, Alzheimer's Disease Assessment Scale, Positive and Negative Syndrome Scale, Schizophrenia Cognition Rating Scale, Conners Adult ADHD Rating Scales, Hamilton Rating Scale for Depression, Hamilton Anxiety Scale, Montgomery-Asberg Depressing Rating scale, Young Mania Rating Scale, Children's Depression Rating Scale, Penn State Worry Questionnaire, Hospital Anxiety and Depression Scale, Aberrant Behavior Checklist, Activities of Daily Living scales, General Practitioner Assessment of Cognition, Eriksen Flanker Task, Stroop Task, Intelligence quotient, Raven's Progressive Matrices, Behavior Rating Inventory of Executive Function (BRIEF), Test of Everyday Attention (and Test of Everyday Attention for Children), Test of Memory and Learning, Wisconsin Card Scoring Test, and Delis Kaplan Executive Function System. In certain embodiments, a subject performing a processor-implemented method provided herein experiences an improvement of cognition after performing the processor-implemented method for at least 10 minutes, 20 minutes, 30 minutes, 40 minutes, 50 minutes, or at least one hour, at a frequency of twice a day, daily, every two days, every three days, every four days, every five days, every six days, or weekly for a total period of one day, two days, three days, four days, five days, six days, one week, two weeks, three weeks, four weeks, one month, two months, three months, four months, five months, or at least six months. Improved cognition in the subject can be measured as improvement of performance in a cognitive ability test (e.g., one of the cognitive ability tests listed in Table 1 and Table 2). In certain embodiments, the improvement can be an improvement by at least 2%, 3%, 4%, 5%, 6%, 7%, 8%, 9%, 10%, 15%, 20%, 25%, 50%, or at least 75% in the performance of one of the cognitive ability tests listed in Table 1 or Table 2 relative to the subject's performance in the cognitive ability test prior to the performance by the subject of a processor-implemented method provided herein. The improvement can be an improvement in score and/or an improvement in timing.

As yet another example, the subject's cognitive ability is assessed by pre-training and post-training physiological tests that measure internal markers of disease or health such as detection of amyloid beta, cortisol and other stress response markers; and brain imaging studies that assess a condition based on presence of specific neural signatures. For example, the subject suffers from age-related cognitive decline, mild cognitive impairment, Alzheimer's disease, Parkinson's disease, Huntington's disease, depression, schizophrenia, dementia, Pick's disease, cognitive deficit associated with fatigue, multiple sclerosis, post traumatic stress disorder, obsessive-compulsive disorder, brain damage, anxiety, stress, panic, depression, dysphoria, malaise, attention deficit disorder, Autism Spectrum Disorder, chronic neurological illnesses or chronic psychiatric illnesses.

According to yet another embodiment, a method of monitoring a treatment of a disease that results in impaired cognition in a subject is provided. The method includes: (i) performing by the subject the processor-implemented method according to any embodiment in the present disclosure to obtain a first set of performance data; (ii) administering to the subject a treatment for said disease for a period of time; (iii) after the period of time, performing by the subject the processor-implemented method according to any embodiment in the present disclosure to obtain a second set of performance data; (iv) comparing first set of performance data and the second set of performance data; and (v) adjusting the treatment for said disease in the subject. In certain embodiments, adjusting the treatment for said disease in the subject comprises increasing or decreasing the frequency of administration of said treatment and/or increasing or decreasing the dose of the treatment and/or administering a new treatment for said disease.

DETAILED DESCRIPTION

Figure 1A:
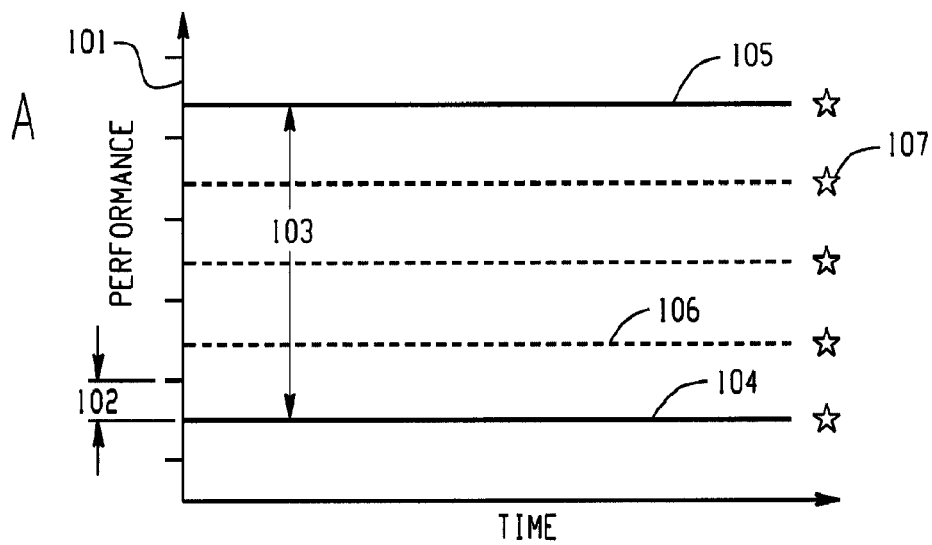
FIG. 1A depicts an example diagram showing definitions of Difficulty Level, Performance Range, Progress Gates, and an individual's performance value.
Figure 1B:
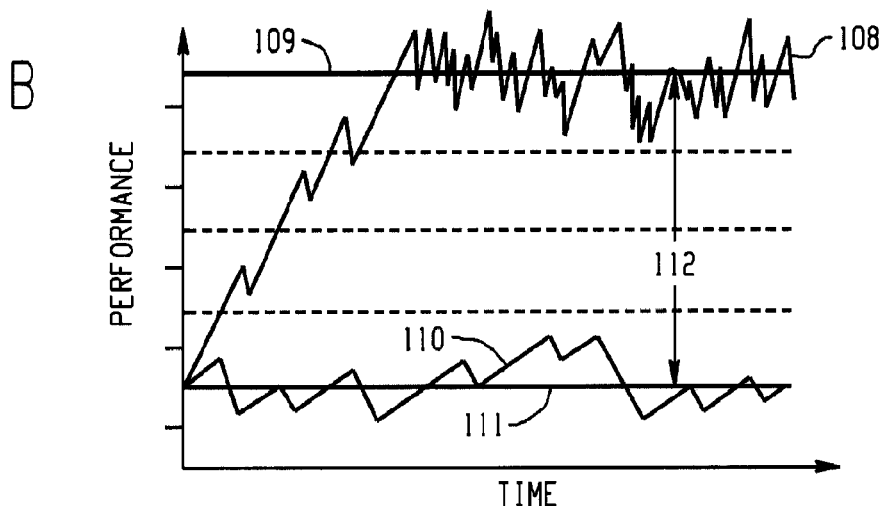
FIG. 1B depicts an example diagram showing a user's single and dual task "performance cases" being mapped onto the diagram shown in FIG. 1A.

FIG. 1 is a graphical representation of the framework for setting personalized difficulty and rewards in an adaptive training regimen, according to the system and methods of the present disclosure. FIG. 1A is a plot of performance on a task over time. The performance axis (101) is divided into discrete, uniform intervals, with each interval corresponding to a unit difficulty level (102). A unit difficulty level corresponds to a specific increment in a parameter related to task complexity, for example, a 50 s increment in the response time window for a target discrimination task. During training, a subject may be permitted to sample all difficulty levels on the performance axis ad infinitum, or, in an embodiment, the subject is allowed to experience a specific subset of difficulty levels. This pre-determined range of difficulty levels that a subject is permitted to sample during training is defined as the subject's performance range, shown in 103. The performance range of an individual is personalized based on his/her current baseline performance on the task, and his/her target maximal ability determined from a recent assessment. The subject's performance range may be defined by one of many suitable methods outlined in the disclosure. In an embodiment, the performance range is set between the difficulty level corresponding to the subject's performance on a single task (higher performance) and the level corresponding to the subject's performance on the same single task when performed concurrently with another task i.e. the subject's performance in a dual task situation (lower performance). This is illustrated in detail in FIG. 1B. Further, the performance range is divided into 'progress gates' tied to specific difficulty levels within the range that the subject may perform at in order to progress in training. Progress gates may be distributed continuously throughout the performance range or may be set at discrete difficulty levels within this range. According to an embodiment of the present disclosure, progress gates are distributed at discrete intervals within the performance range, with a starting progress gate (104) set at the lower bound of the subject's performance range, an ending progress gate (105) set at the upper•bound of the subject's performance range and intermediate progress gates (106) distributed evenly between the starting and ending progress gates. Each progress gate is represented by rewards (107), which are presented to the subject when he/she achieves performance at the progress gate.

FIG. 1B illustrates a subject's performance during an assessment, mapped onto the performance and difficulty framework described in FIG. 1A according to an embodiment in the present disclosure. In this embodiment, the median convergence value of the subject's performance on a single task during assessment (108) is set as the upper bound of the subject's performance range for training. The upper bound corresponds to the subject's ending progress gate (109). The median convergence value of the subject's performance on the same task when performed concurrently with another task, i.e., the subject's performance in a dual task condition (110) is set as the lower bound of the subject's performance range for training. This corresponds to subject's starting progress gate (111). Therefore, the subject's performance range (112) for training extends between the difficulty levels corresponding to the subject's current ability on a task performed in a dual-task (more challenging) situation and the subject's performance in a single task (i.e. less challenging) situation.

Figure 1C:
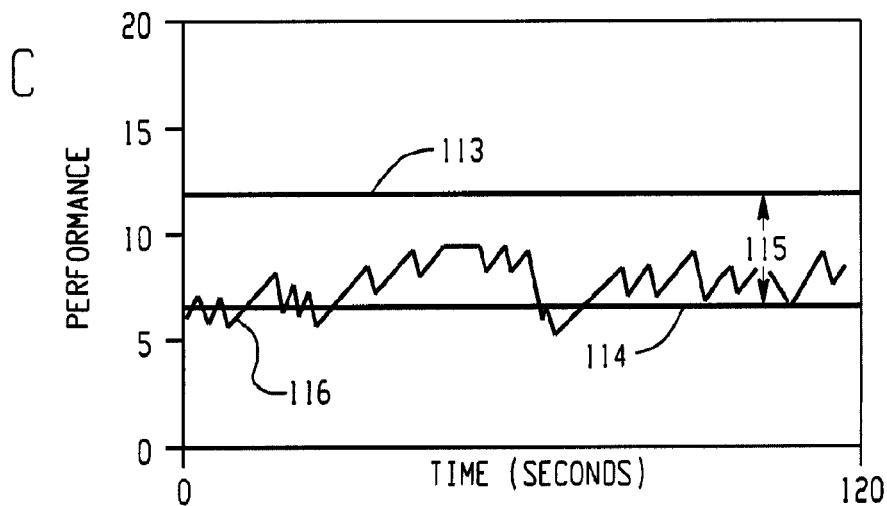
FIG. 1C depicts an example diagram showing a single training phase from a cognitive training program, in accordance with one embodiment in the present disclosure.

FIG. 1C is a screenshot of a single subject's performance in a cognitive training game (e.g., Project: EVO). The subject's performance range (115) is shown, defined as the range of difficulty levels between the median convergence value of the subject's performance on a single task (113) and the median convergence value of the subject's performance on the task when performed in a dual-task condition (114), as described in detail in FIG. 1B. The subject's performance trajectories on the task over time in the single and dual-tasks situations during assessment are not shown. 114 and 113 correspond to the subject's starting and ending progress gates respectively. The intermediate progress gates between the starting and ending progress gates are not shown. 116 shows the subject's performance on the task over time during a single training session. Note, that in accordance with one embodiment in the present disclosure, the subject initiates training at a difficulty level corresponding to the starting progress gate, and samples a range of difficulty levels within a predetermined increment of the performance range during training.

Figure 2:
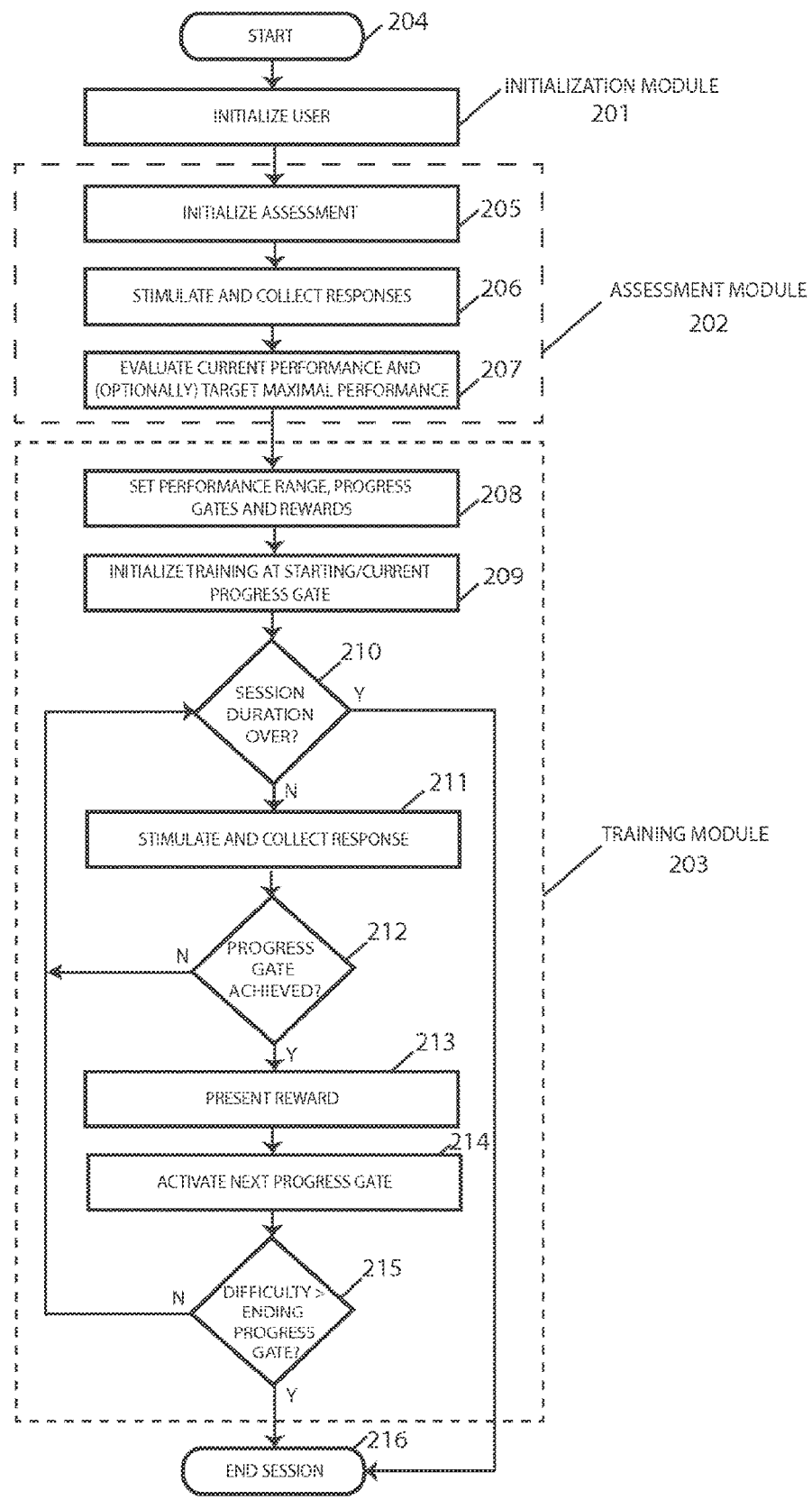
FIG. 2 is an example flow chart that describes a cognitive training method in accordance with embodiments in the present disclosure.

FIG. 2 is a high-level flow chart of one embodiment of the method and system for personalized adaptive training as described in the present disclosure. The system comprises 3 modules, an initialization module 201, an assessment module 202 and a training module 203. First, at step 204, a session begins. A new subject is initiated into the system by the initialization module 201, by collecting demographic information regarding the subject and creating a new subject profile (not shown). Existing subjects may be initialized by the system into a new session, by recovering their saved subject profiles and data on past training and performance. Initiated subjects are next guided to the assessment module 202, where, at step 205, they are offered instructions for performing specific tasks. At step 206, subjects are presented with suitable stimuli and their responses are recorded. At step 207, the subject's responses are evaluated to determine their current baseline performance on the presented task(s).

The system may optionally evaluate the target maximum skill level to train the subject towards in the subsequent training module 203. The training module 203 is activated after a subject successfully completes the assessment module 202. In this module, step 208 first performs operations for the personalization of the training difficulty and rewards for the subject participating in training. The subject's baseline performance measured in the recent assessment is used to define the subject's training performance range i.e. the range of task difficulty levels that the subject will be allowed to sample during the training steps 209-216. Additionally, the subject's personalized progress gates and rewards are defined, with the starting and ending progress gates set at the lower and upper bounds of his/her training performance range respectively; and the intermediate progress gates and rewards set at specific difficulty levels within the performance range that the subject may perform at in order to advance in training.

Once the system has determined the performance range, task difficulty levels and reward levels for the participating subject, the subject is initialized into the training at step 209. Training for a new subject is initiated at a difficulty level corresponding to the subject's starting progress gate. Training for an existing subject is initiated at a difficulty level corresponding to the highest progress gate the subject successfully performed at in a previous training session. Upon the start of the cognitive training process at step 209, the training may continue for the length of the predetermined duration of the session at step 210. After the desired session length is reached, the training session ends at step 216. If the current duration time is less than the desired duration time, the system continues to the present to the subject suitable stimuli related to the task(s) to be completed for training, and collects the subject's responses at step 211.

The difficulty of the task(s) presented to the subject at step 211 may be adjusted by the system by any adaptive means such as block adaptation, maximum likelihood procedures, single staircase algorithms or other suitable approaches known in the art. When a subject submits a correct response at 211, the difficulty of the task(s) may be incremented until the current task difficulty level matches a pre-determined difficulty level specified by a progress gate. When this condition is achieved, the subject's performance is evaluated to determine if it satisfies the criteria for a successful completion of the progress gate (212). The system may employ one or more of various criteria to define successful performance at the progress gate. Some examples are: time to attain the task difficulty level corresponding to the progress gate, duration of performance at the difficulty level corresponding to the progress gate or combined performance on dual or multiple tasks at pre-determined difficulty levels. If the subject's performance is deemed successful and a progress gate is achieved, the system presents to the subject a suitable reward at step 213 to indicate progress. The system then activates the next incremental progress gate at step 214, permitting the subject to experience task difficulty levels greater than the difficulty level specified by the most recently achieved progress gate. The system iteratively stimulates the subject, adjusts task difficulty levels and activates incremental progress gates (steps 211-214), until the subject achieves performance at the difficulty level corresponding to the ending progress gate. The session ends at step 216 when the subject achieves the ending progress gate.

Figure 3:
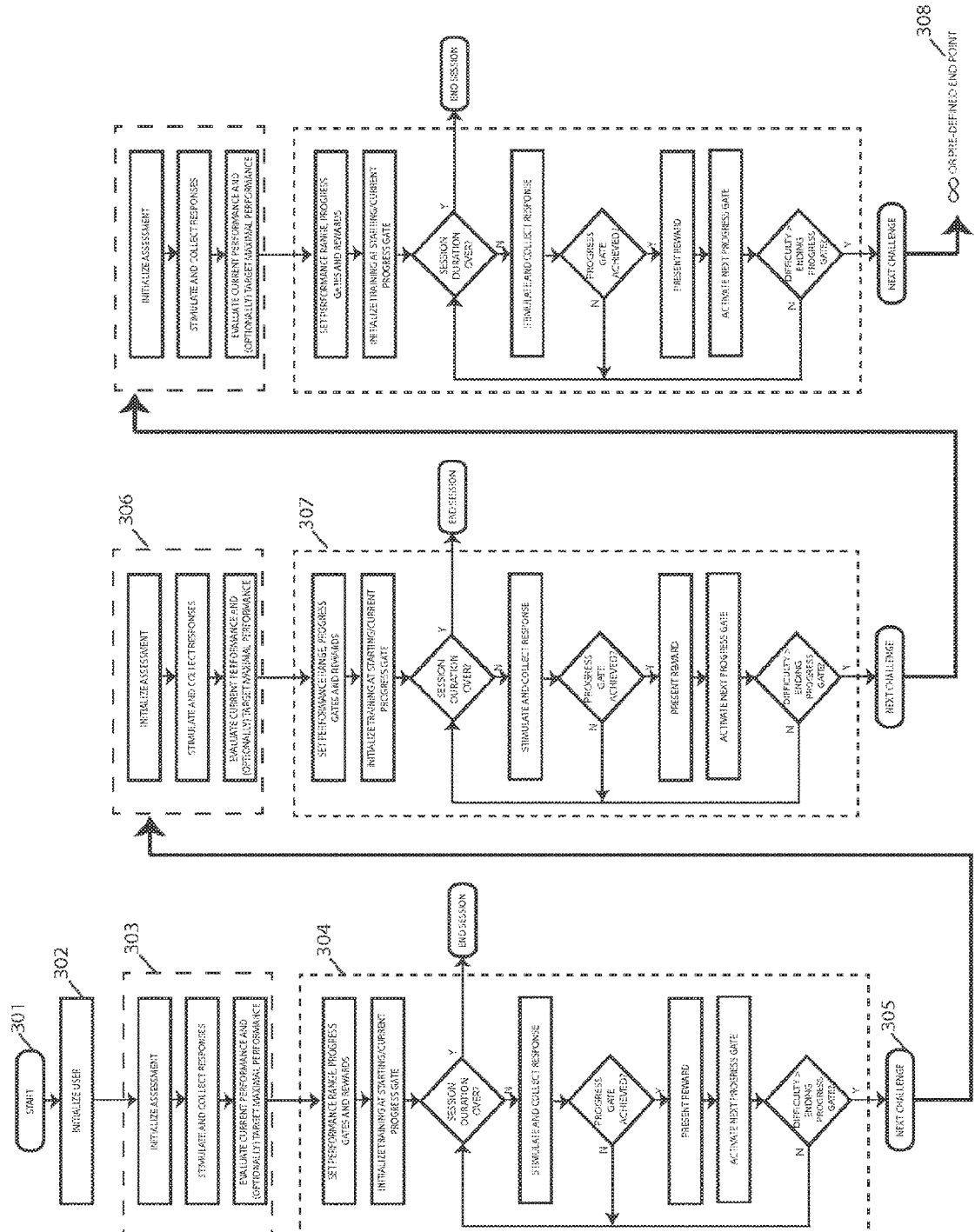
FIG. 3 is an example flow chart that describes a cognitive training method in accordance with an embodiment in the present disclosure.

FIG. 3 is a flow chart of an embodiment of the method and system for personalized adaptive training, illustrating the repeating assessment-training cycles described in the present disclosure.

It is an aspect of the present disclosure, to minimize the practice effects experienced by a subject with increasing time and interaction with the cognitive training system. The cognitive training provided to the individual by the system is continuously challenging, and is tailored to the subject's true current cognitive ability. Accordingly, the system conducts multiple assessments throughout the training regimen, each assessment re-setting the difficulty and reward parameters for the subsequent training. As illustrated in FIG. 3, a new session begins at step 301 and is followed by initialization (302), assessment (303) and training (304) of the subject as described in detail in FIG. 2. When a subject successfully completes training on the set task(s) by performing at a difficulty level corresponding to his/her personalized ending progress gate, the system directs the subject to a new challenge (305), which may comprise a more complex or difficult variation of the recently completed task(s) or a new set of tasks. The new challenge is initiated by a fresh assessment (306) to determine the subject's baseline cognitive abilities after the prior training session, followed by training on the new set of tasks (307). This cycle of assessment-training-new challenge assessment-training may continue ad infinitum or until the system achieves a pre-defined end point (308) such as completion of a set number of challenges or reaching a pre-determined duration of training, for example a week or a month.

Figure 4:
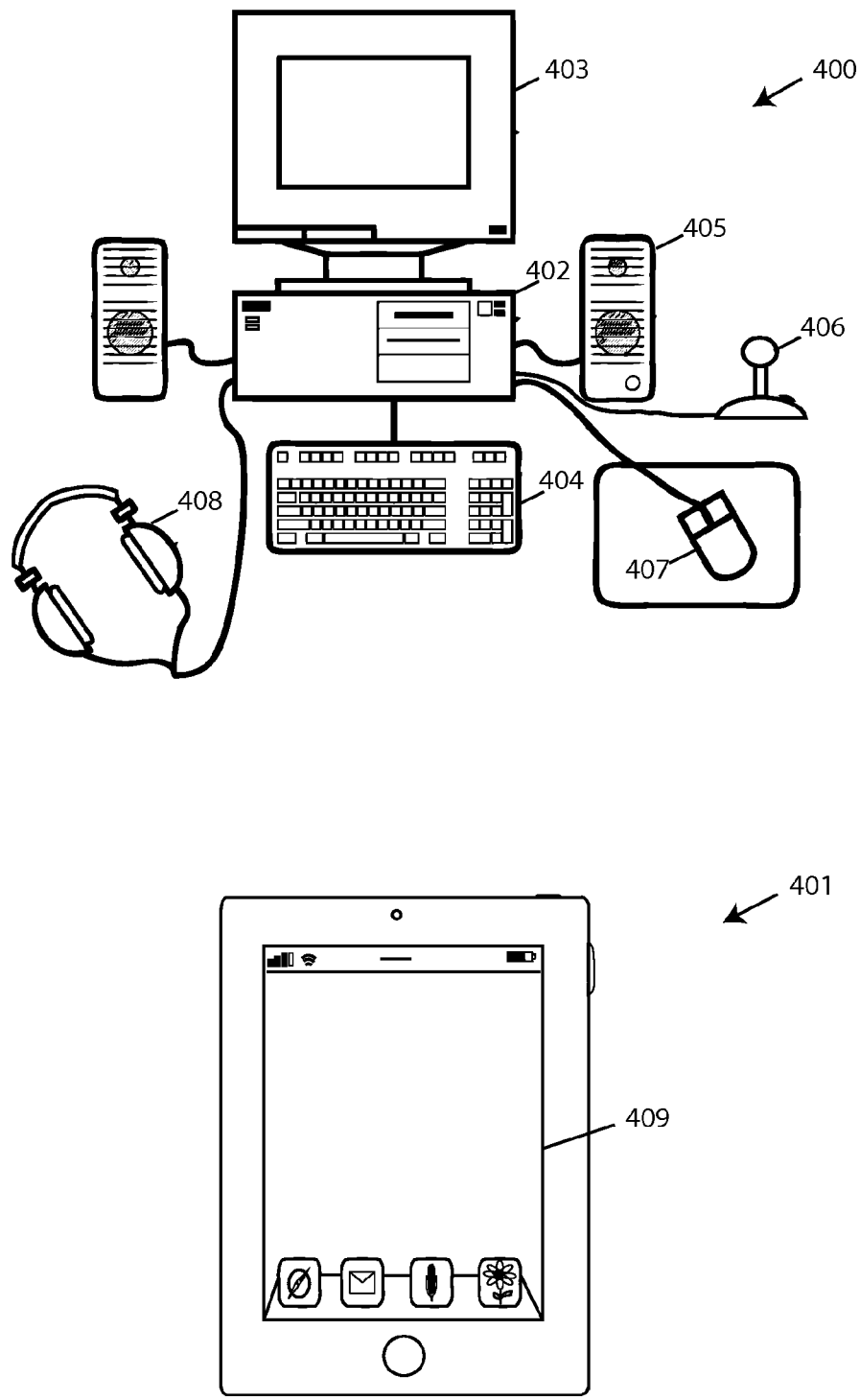
FIG. 4 depicts example computer devices that can be used to practice embodiments of the present disclosure.
Figure 5A:
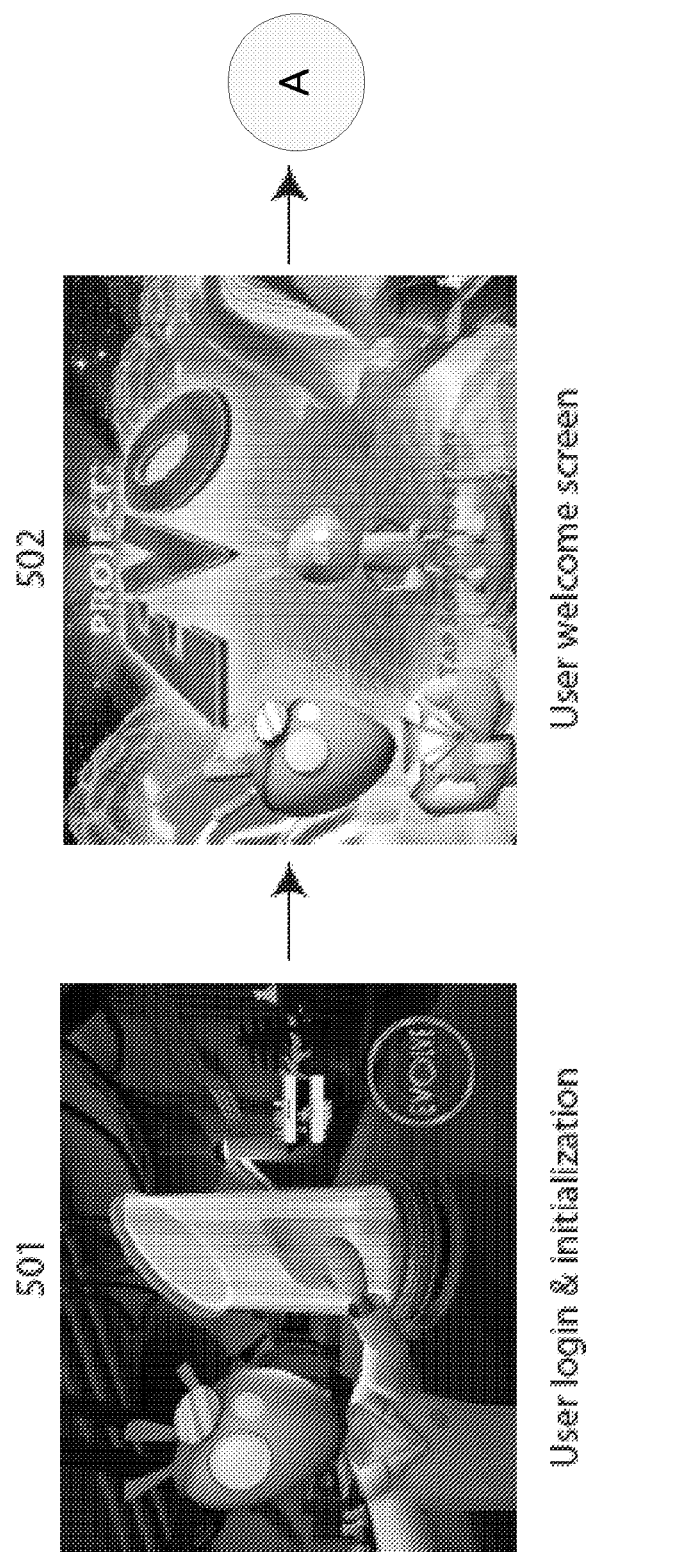
FIG. 5A-FIG. 5F depict example screenshots of a cognitive training program.
Figure 5B:
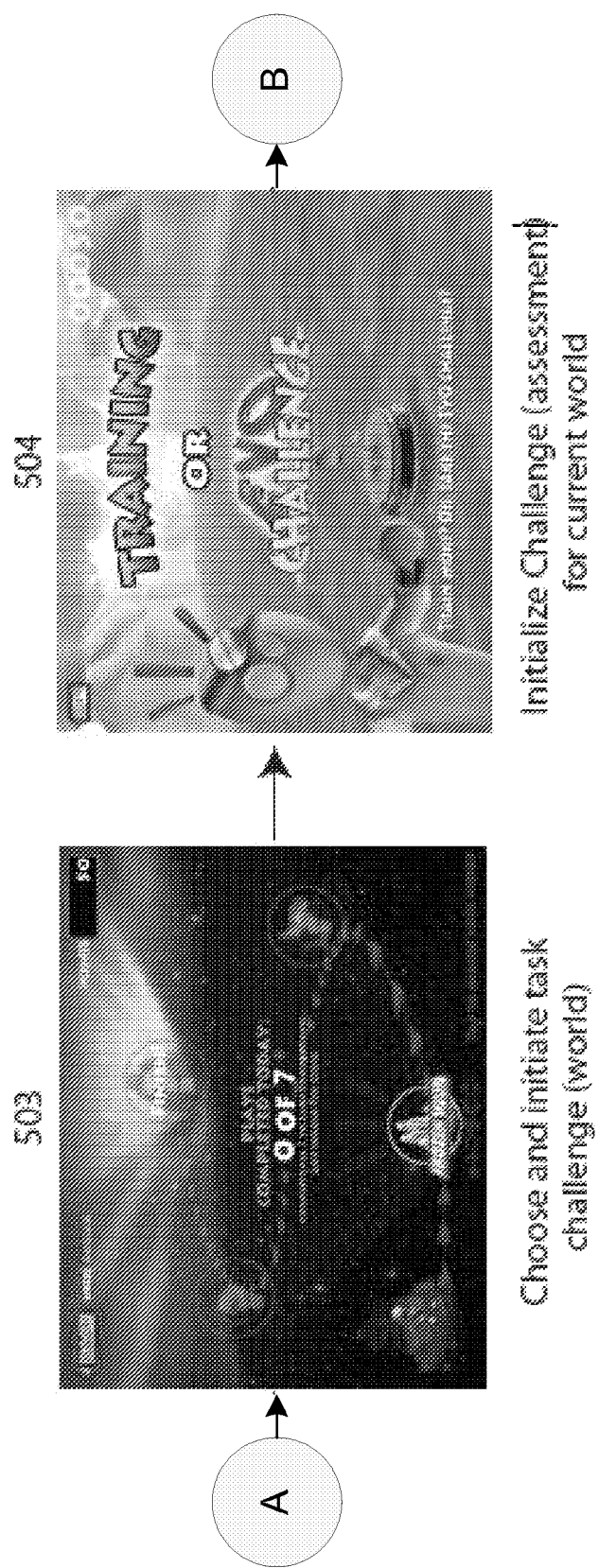
Figure 5C:
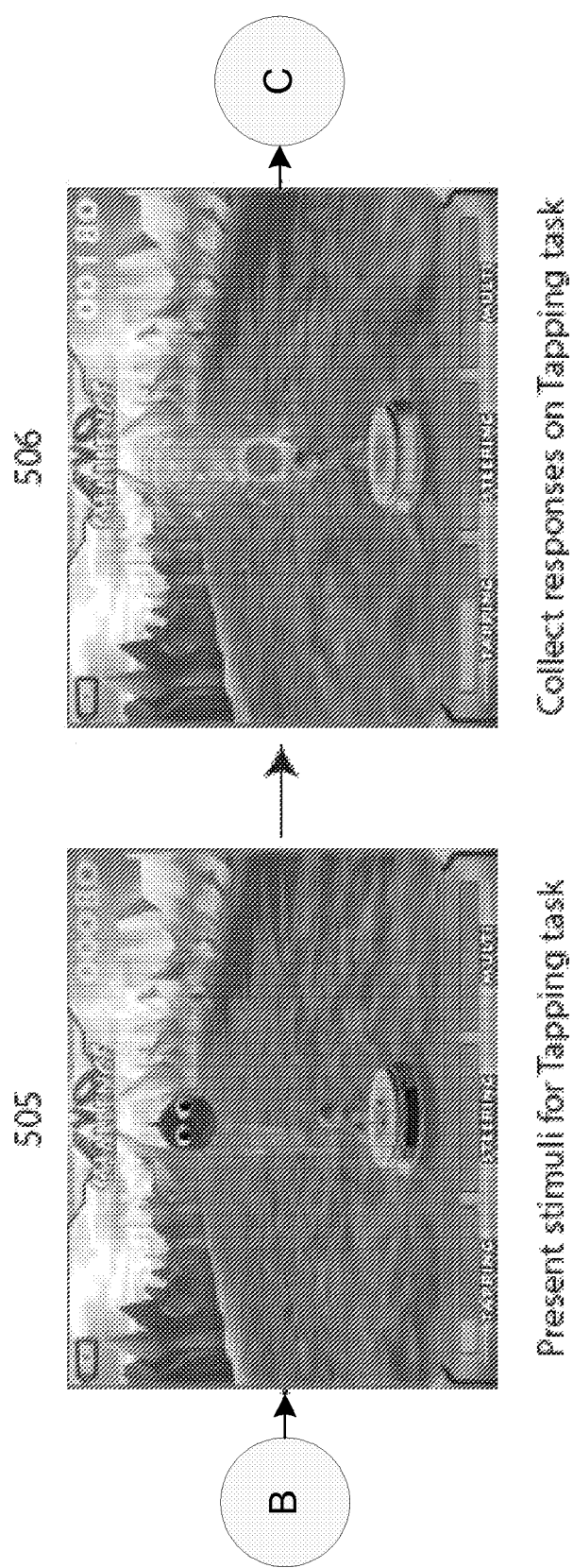
Figure 5D:
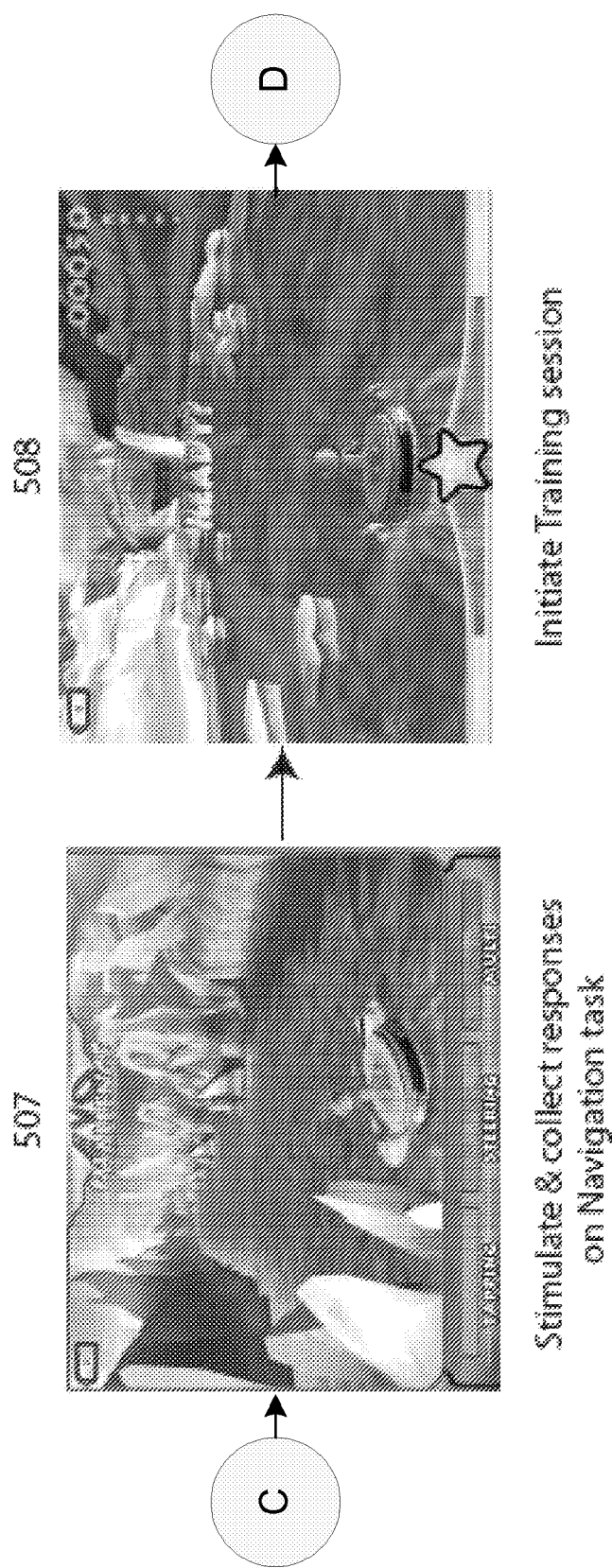
Figure 5E:
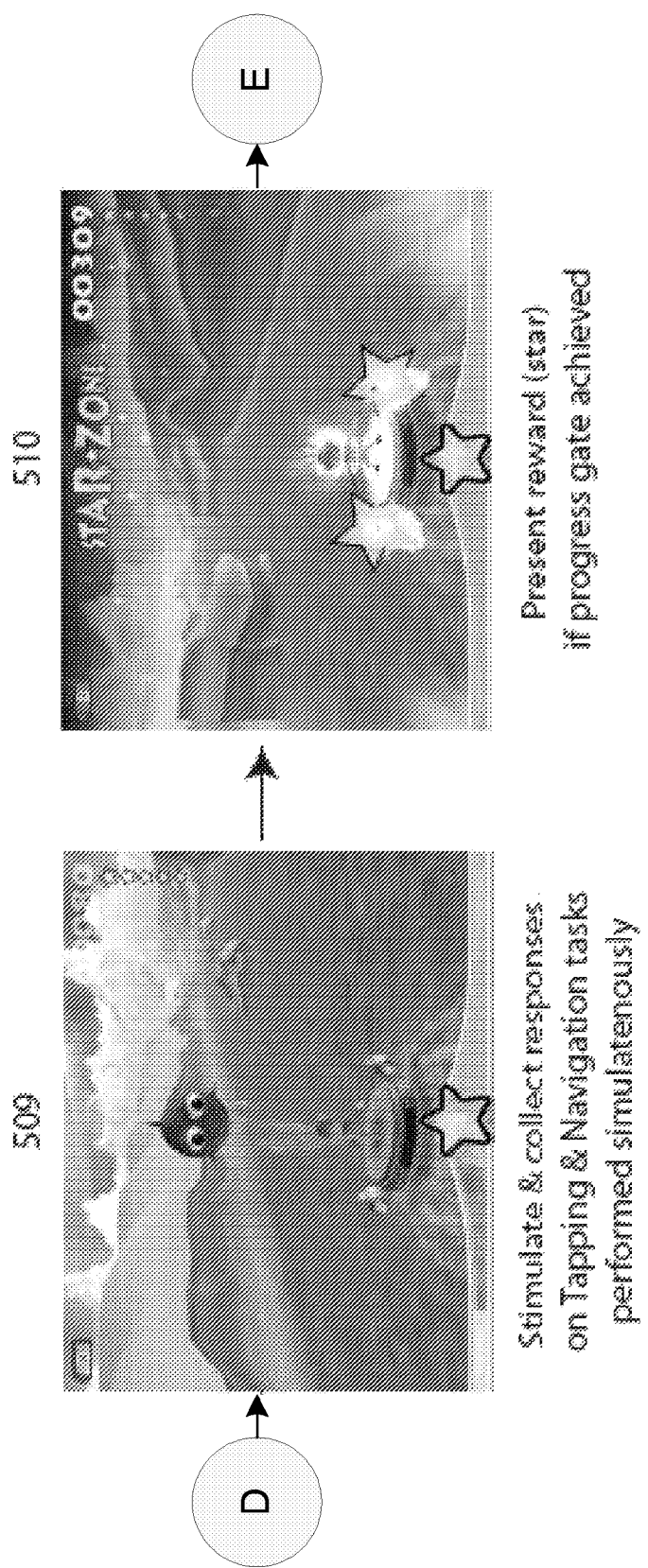
Figure 5F:
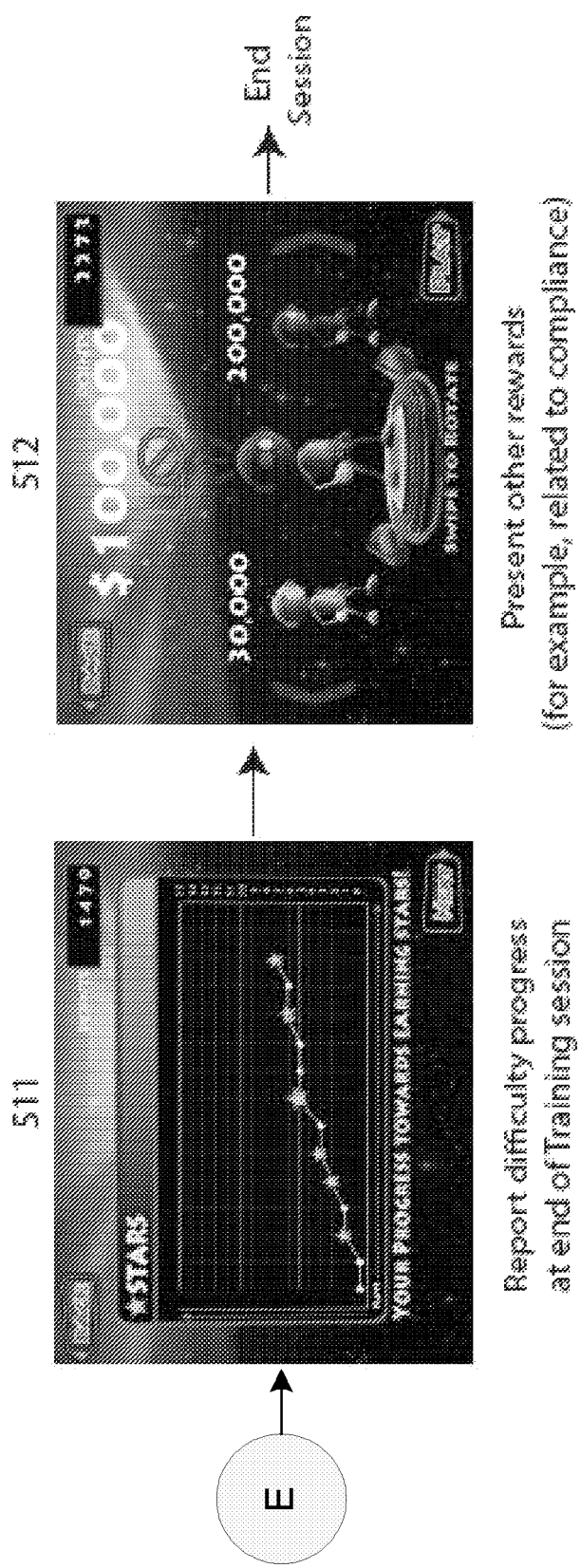

FIG. 4 illustrates two types of computer systems 400 and 401 with which embodiments of the present disclosure may be practiced. The computer system 400 contains a computer 402, having a CPU, memory, hard disk and CD ROM drive (not shown), attached to a monitor 403. The monitor 403 provides visual prompting and feedback to the subject during execution of the computer program. Attached to the computer 402 are a keyboard 404, speakers 405, a joystick 406, a mouse 407, and headphones 408. In some embodiments, the speakers 405 and the headphones 408 may provide auditory prompting, stimuli and feedback to the subject during execution of the computer program. The joystick 406 and mouse 407 allow the subject to navigate through the computer program, and to select particular responses after visual or auditory prompting by the computer program. The keyboard 404 allows the subject or an instructor to enter alphanumeric information about the subject into the computer 402. Embodiments of the present disclosure can be deployed on a number of different computer platforms e.g. IBM or Macintosh or other similar or compatible computer systems, gaming consoles or laptops.

401 illustrates a suitable mobile computing environment, for example, a tablet personal computer or a mobile telephone or smart phone on which certain embodiments in the present disclosure can be deployed. In a basic configuration, mobile computing device is a handheld computer having both input elements and output elements. Input elements may include touch screen display 409 and input buttons (not shown) that allow the user to enter information into the mobile computing device. The screen display 409 provides visual prompting, stimuli and feedback to the user during execution of the computer program. The output elements comprise the inbuilt speaker (not shown) that in some embodiments may provide auditory prompting, stimuli and feedback to the user during execution of the computer program. In alternative embodiments, the mobile computing device may incorporate additional input or output elements such as a physical keypad to enter alphanumeric information or a headphone jack (not shown). Additionally, the mobile computing device may incorporate a vibration module (not shown) which causes mobile computing device to vibrate to provide stimulus or feedback to a user during execution of the computer program.

FIG. 5A-FIG. 5F include a pictorial representation of a cognitive training game (e.g., Project: EVO), which uses methods described in the present disclosure to present to an individual a personalized cognitive training experience. FIG. 5A-FIG. 5F show exemplary screenshots from one game session comprising the initiation, assessment and training steps described in detail in FIG. 2. The session begins with a user login screen (501), where new users first set up a user profile and enter demographic information. New and existing users are then greeted with a welcome screen (502), inviting them to tap the screen to initiate a new task challenge. Users can select which task challenge ('world') to undertake in the next step (503). Project: EVO comprises multiple worlds with progressive task complexity. New users can choose the first world for their initial session. Subsequent worlds are unlocked when users are able to successfully perform at the previous worlds. Once a user selects a world, the system provides an option to initiate an assessment (called a 'Challenge' session in the game) or a training session (504). New users may initiate with an assessment, while existing users are provided an option to retake an assessment or to continue with training Project: EVO evaluates and trains individuals on two types of tasks: a perceptual reaction task called Tapping, and a visuomotor task called Navigation. The assessment begins with the Tapping task where users are stimulated with visual targets and their responses collected (505, 506). This is followed by an assessment of the user's ability on the Navigation task performed in isolation (507), and his/her performance on both Tapping and Navigation tasks performed simultaneously (not shown). Once the user's baseline performance levels have been determined in the assessment and the personalized performance range and difficulty progression for the training session calculated, users are directed to initiate a training session (508). During training, users have to perform the Tapping and Navigation tasks simultaneously, and their performance on both tasks (i.e. their multitasking performance) is recorded (509). When users perform at a difficulty level corresponding to a progress gate, they are presented with a reward in the form of a star (510). At the end of the training session, users are reported their overall progress in training (511). Users are also presented with other rewards that may be tied to performance or other metrics such as number of assessment or training sessions completed (512). The session ends, and users are redirected to screen 503 to continue assessment and training in the same world or progress to the next world.

Figure 6:
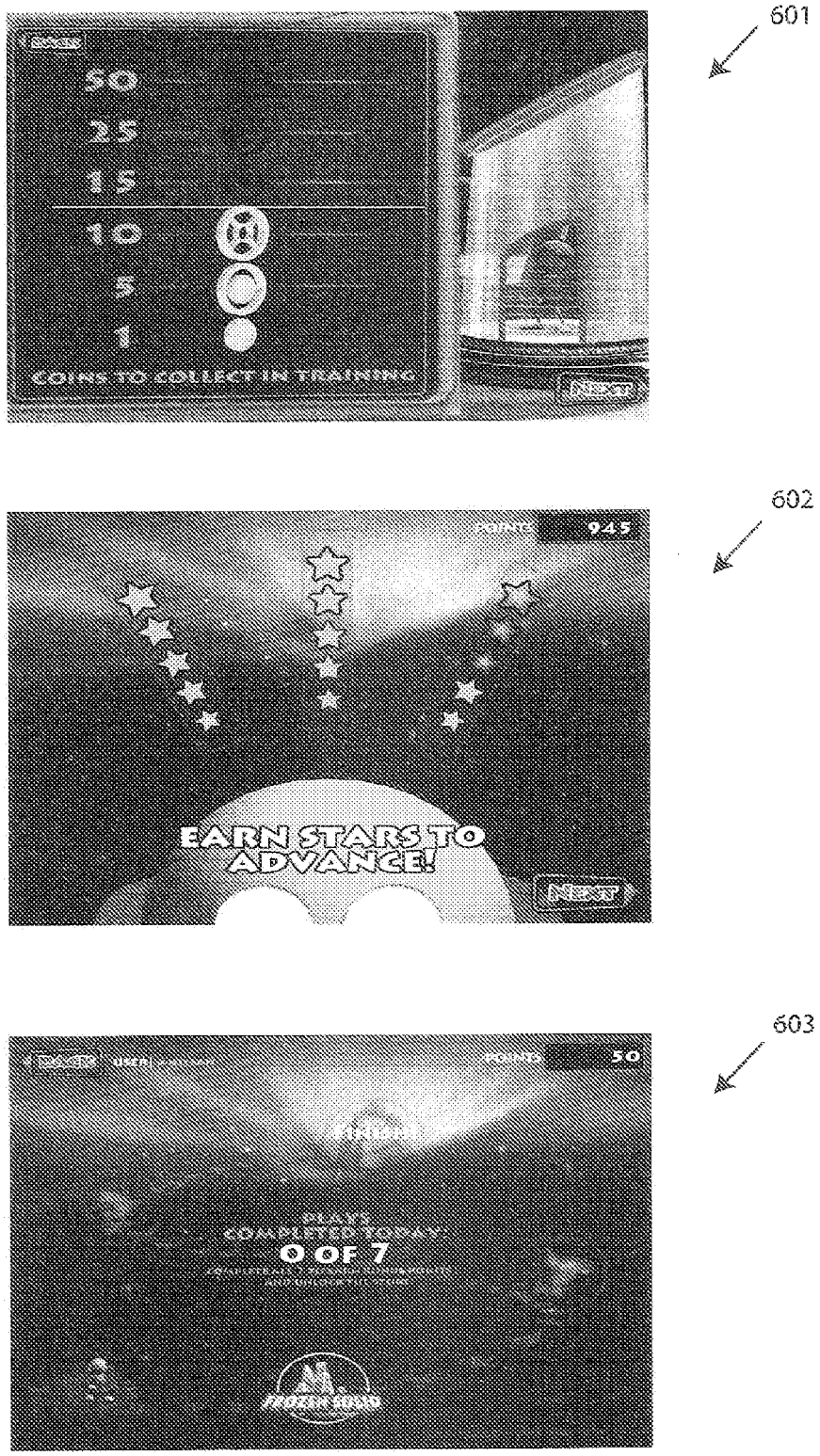
FIG. 6 depicts an example picture of rewards that are linked to difficulty levels in the cognitive training program, in accordance with one embodiment in the present disclosure.

FIG. 6 is a pictorial representation of the rewards presented to the user in the cognitive game Project: EVO, to motivate user engagement and compliance. Three exemplary rewards are shown, which are tied to the user's performance and personalized difficulty progression in the game, in accordance with one embodiment in the present disclosure. 601 is a screenshot of the wrap-up screen presented to the user after an assessment session, which reports the number of 'supercoins' earned by the user during the assessment. Supercoins represent rewards offered to the user for performing at specific difficulty levels during an assessment, and are intended to motivate the user to perform at his/her maximal current ability during the assessment. 602 is a screenshot from the game reporting the user's star level.

Stars represent rewards tied to the user's personalized performance range and progress gates for training A user earns a star each time he/she successfully performs at a difficulty level corresponding to a progress gate. In Project: EVO, a user's performance range for training is divided into 5 progress gates, allowing the user to earn up to 5 stars in a training session. After earning 5 stars, the user is presented with a re-assessment to evaluate his/her new baseline performance levels and reset the performance range for subsequent training sessions. In Project: EVO, a user undergoes multiple re-assessments and training cycles and has to earn 15 stars before he/she is allowed to progress to the next world. 603 is a screenshot of the multiple worlds in Project: EVO. When a user successfully completes training in one world, he/she is rewarded with access to subsequent worlds which comprise tasks with greater complexity than the recently completed world.

Figure 7A:
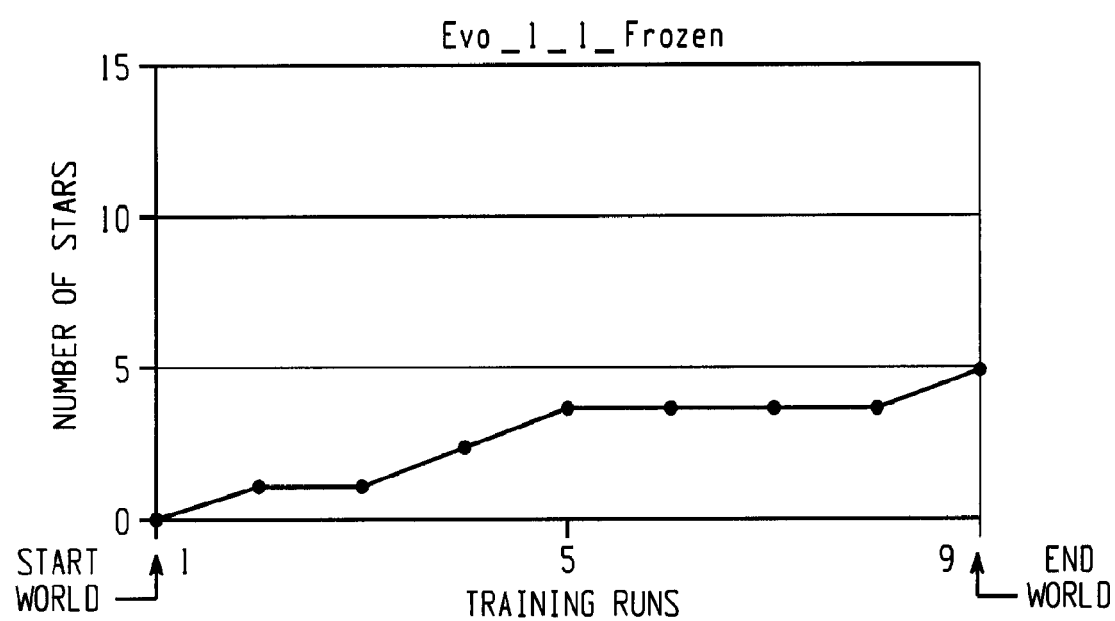
FIG. 7 illustrates example progression data of an exemplary individual study participant through a version of the cognitive training program that has one assessment and one adaptive training phase per task.
Figure 7B:
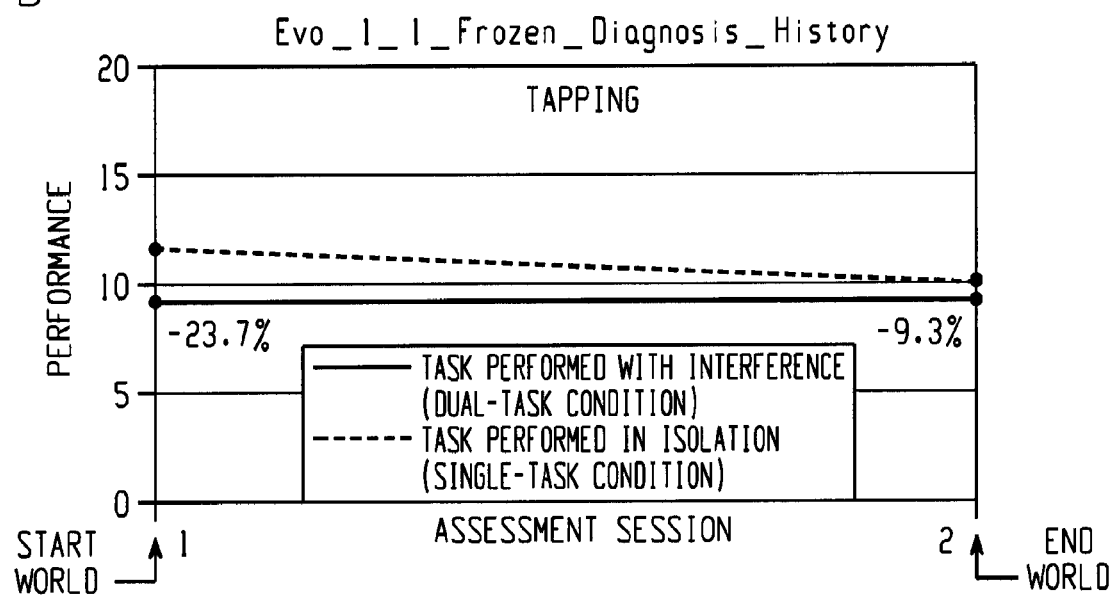
Figure 7B:
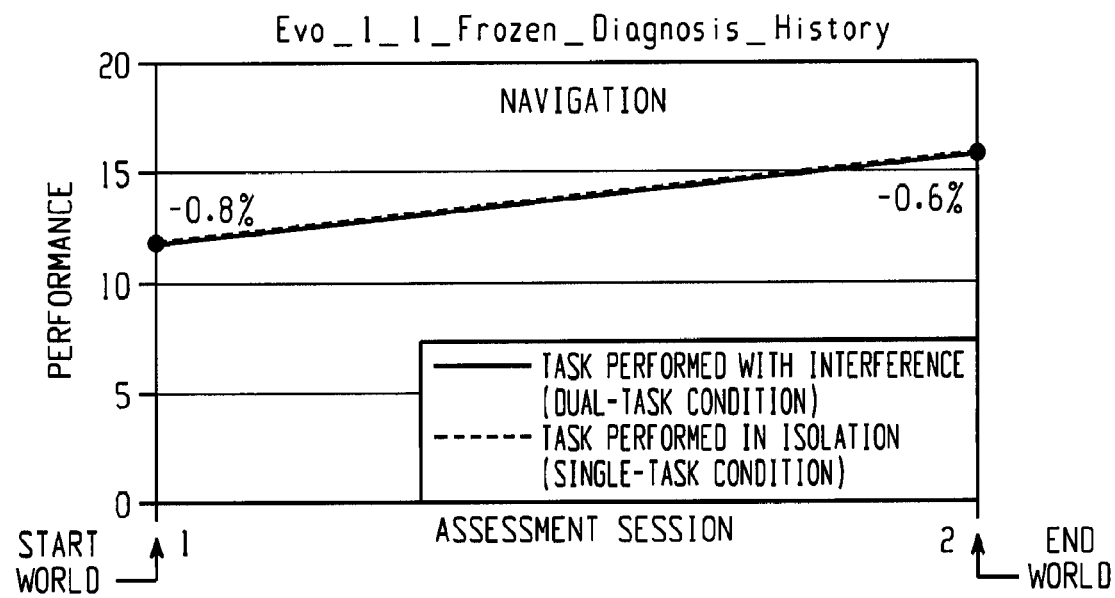

FIG. 7 illustrates the performance data of an exemplary individual study participant on the cognitive training program (e.g., a game Project: EVO). Data was acquired on an early version of Project: EVO that did not incorporate multiple re-assessment and training cycles described by the methods in the present disclosure. Therefore, in this version of the game, assessments (indicated by arrows in FIG. 7A) were conducted at the beginning and at the end of each task-challenge. There were no interim assessments to re-evaluate the individual's baseline performance after a reasonable period of training to recalibrate the performance range and difficulty progression for subsequent training and minimize practice effects. As can be seen in FIG. 7A, the individual demonstrates rapid progress on training, requiring 9 training sessions to attain the star rewards to complete the current task challenge (5 stars) and progress to the next world.

FIG. 7B illustrates the individual's performance on the Tapping and Navigation tasks performed in isolation (dashed lines) and performed simultaneously (solid lines) during the assessments conducted at the beginning and at the end of the task challenge. Percentages indicate the interference cost experienced by the individual at each assessment when performing both Tapping and Navigation tasks simultaneously.

The individual shows improvement in his general ability on the Navigation task (indicated by increase in performance in the single task condition in the later assessment) as well as in his multitasking ability on both Tapping and Navigation tasks (indicated by the reduced interference cost in the later assessments) as a result of training.

FIG. 8 illustrates the performance data of an exemplary individual study participant on an advanced version of the cognitive training program (e.g., a game Project: EVO) that incorporates multiple re-assessment and training cycles in accordance with one embodiment in the present disclosure. In this version, assessments (indicated by arrows in FIG. 8C), were conducted at the beginning and at the end of each task-challenge, and in between during training, at each 5 star increment (i.e., when the individual attained 5 stars and 10 stars). As described by the methods in the present disclosure, each reassessment was used to recalibrate the individual's baseline performance and reset his personalized training performance range and difficulty progression for subsequent training to minimize practice effects.

Figure 8A:
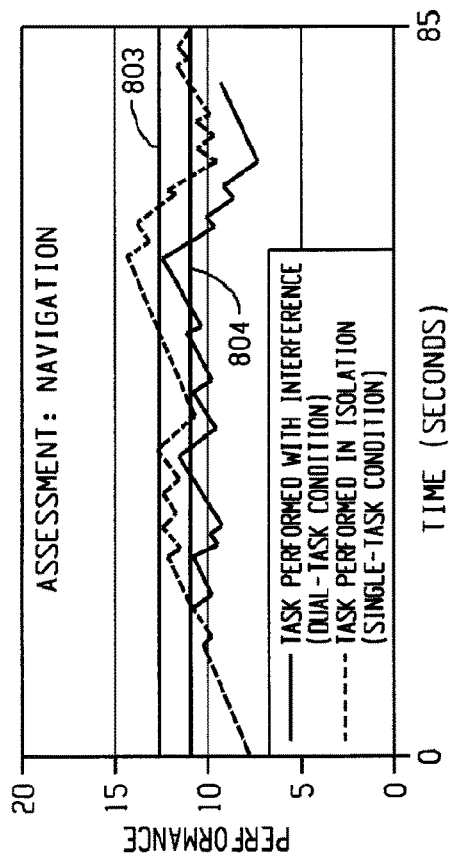
FIG. 8 illustrates example progression data of an exemplary individual study participant through another version of the cognitive training program that includes multiple cycles of assessment and adaptive training phases, in accordance with one embodiment in the present disclosure.
Figure 8A:
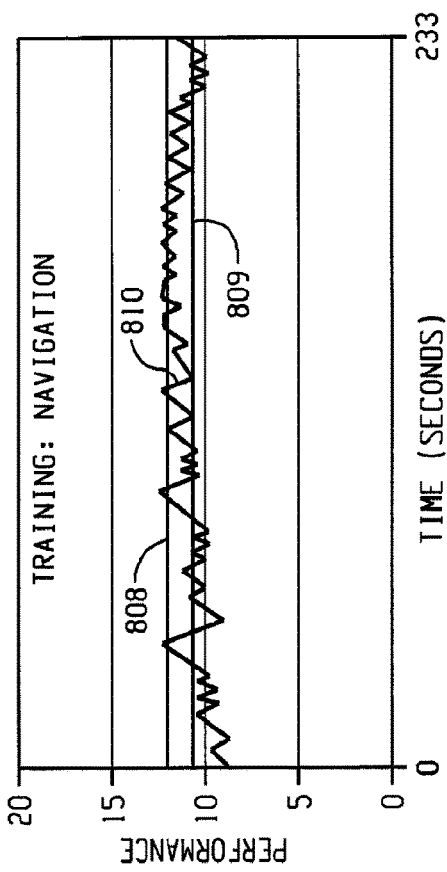

FIG. 8A shows the participant's baseline assessment data on the Tapping and Navigation tasks. The average difficulty level of the single task (801 and 804) and dual-task (802 and 803) phases for each task are shown visually by horizontal lines that cross the y-axis. In accordance with one embodiment in the present disclosure, these levels are used to set the personalized training performance range and the starting (805 and 808) and the ending (806 and 809) progress gates for the individual in the subsequent training module.

Figure 8B:
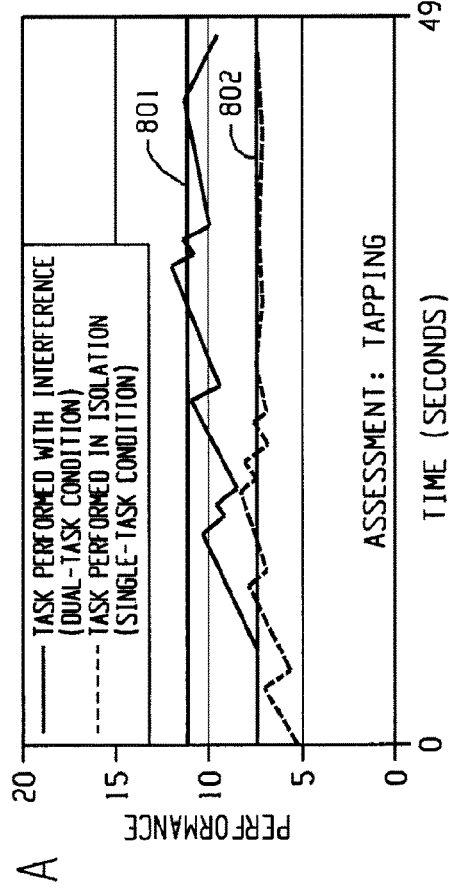
Figure 8B:
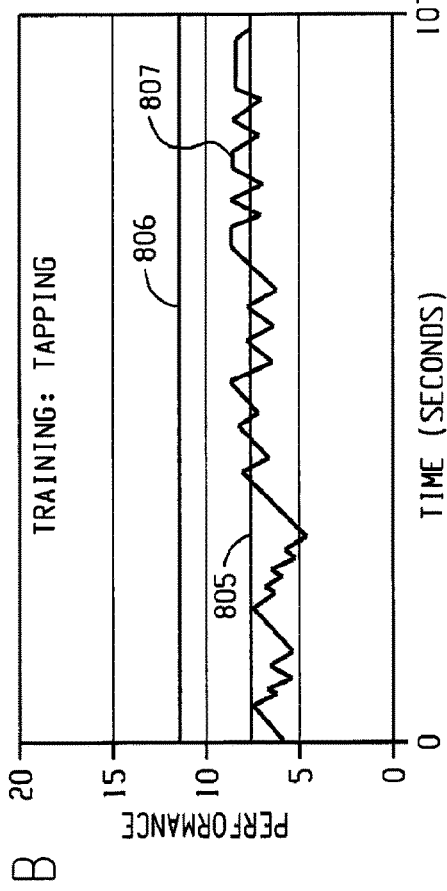

FIG. 8B shows performance data from the first training run performed by the individual. The trajectories 807 and 810 indicate performance on the Tapping and Navigation tasks respectively, when both tasks are performed simultaneously during training.

Figure 8C:
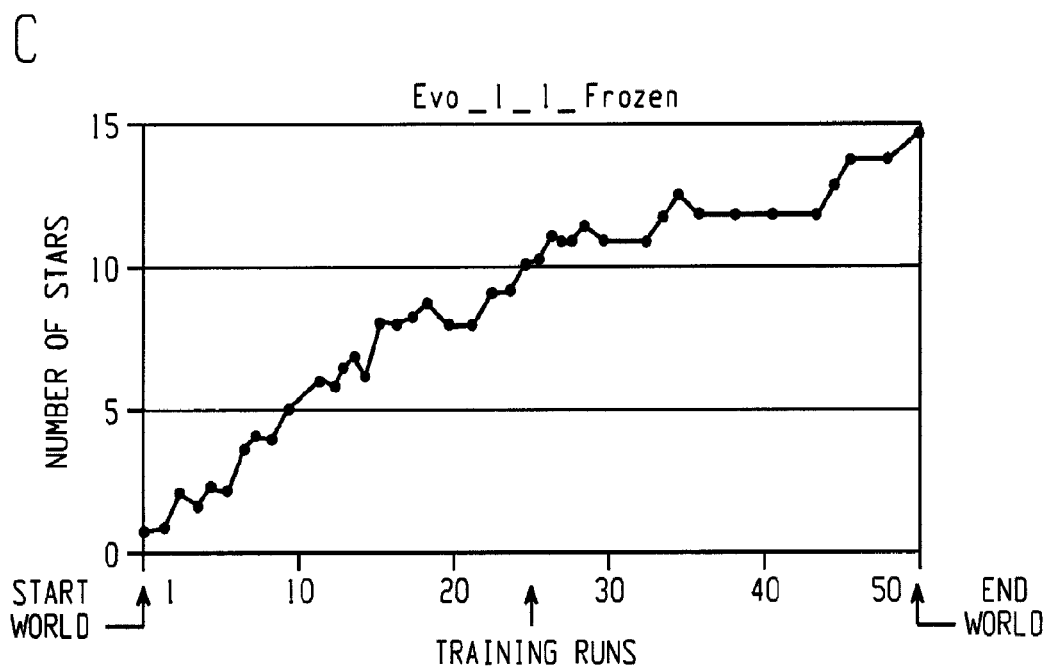

FIG. 8C shows the individual's progress through the task challenge. In this advanced version of Project: EVO, the individual experiences a training regimen that is continuously challenging and suited to his true current abilities on the tasks. As a result, he may need more training to improve his performance on the tasks. As seen in the figure, the individual takes 10 training runs to attain 5 stars, 15 training runs to attain 10 stars and an additional 25 training runs to reach the final 15 star level and successfully complete the task challenge. Further, reassessment of the individual's improved baseline abilities and resetting of his training performance range at each 5 star increment, allows for training of the individual across his full cognitive range. While other cognitive training systems and the early version of Project: EVO that did not incorporate the reassessment-training cycles would have deemed the individual to have attained maximum performance in 10 training runs (i.e. at the 5 star level), this advanced version of Project: EVO allowed for additional improvements in cognition by further training the individual till the 15 star level.

Figure 8D:
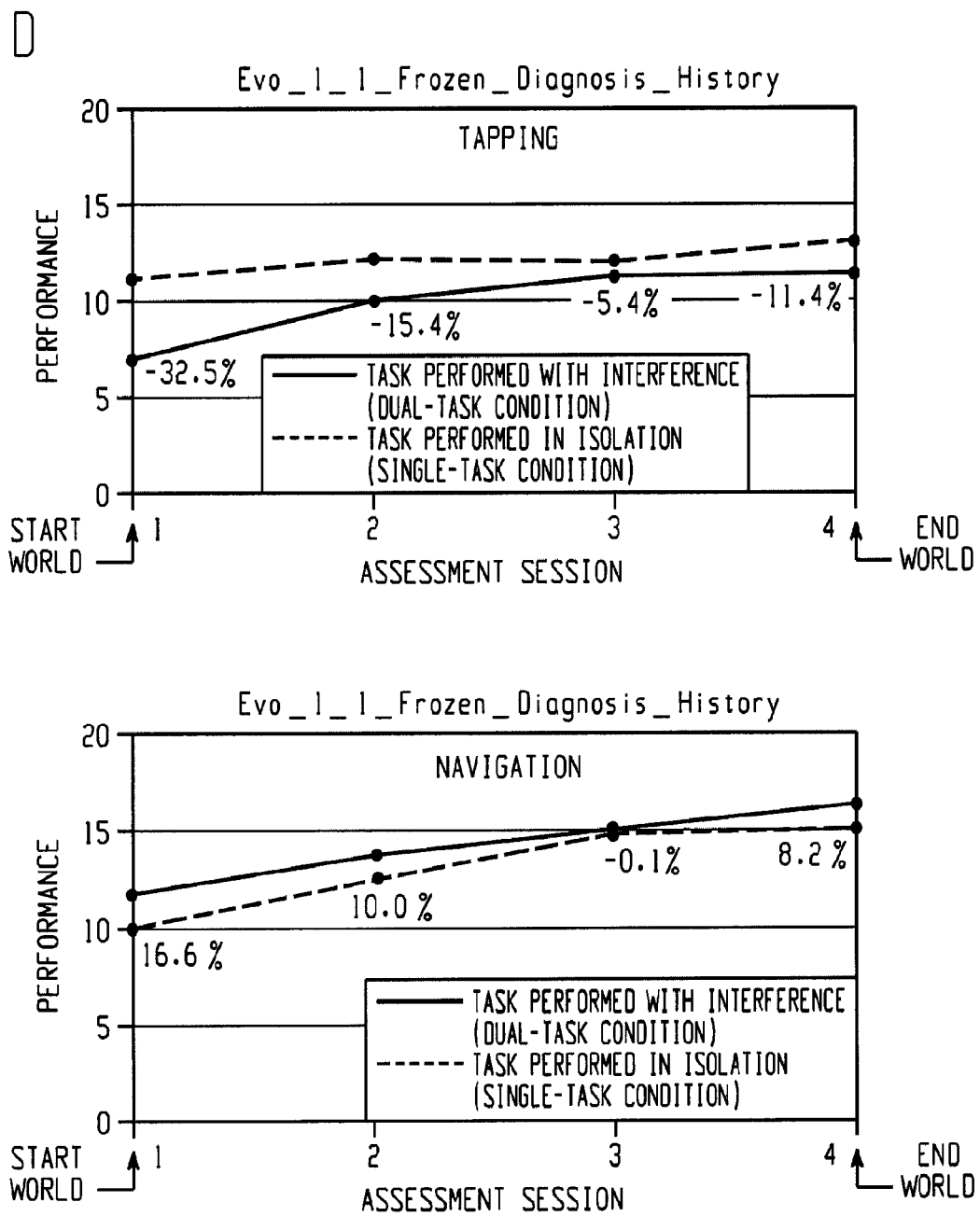

FIG. 8D illustrates the individual's performance on the Tapping and Navigation tasks performed in isolation (dashed lines) and performed simultaneously (solid lines) in the 4 assessment sessions conducted during the current task challenge. Percentages indicate the interference cost experienced by the individual at each assessment when performing both Tapping and Navigation tasks concurrently.

Compared to the individual illustrated in FIG. 7, who trained on an earlier version of Project: EVO, without the reassessment-training cycles, the current individual shows greater improvement in his general ability on both Tapping and Navigation tasks (indicated by higher performance in the single task condition in the last assessment as compared to the initial assessment). Additionally, this individual achieves a ~3 fold improvement in interference cost on the Tapping task and a 2 fold improvement in interference on the Navigation task at the end of training.

FIG. 9 illustrates the performance data from two exemplary individuals that trained on different versions of the cognitive game Project: EVO that differed in the incorporation of lower and upper limit constraints to the individual's performance range during training. It is an embodiment in the present disclosure that a user's training performance range be constrained by lower and upper bounds to ensure play between the individual's current and target performance levels, so as to ensure that the training regimen is continuously and optimally challenging to the individual, without being too easy or too difficult for the user based on his/her current ability.

Figure 9A:
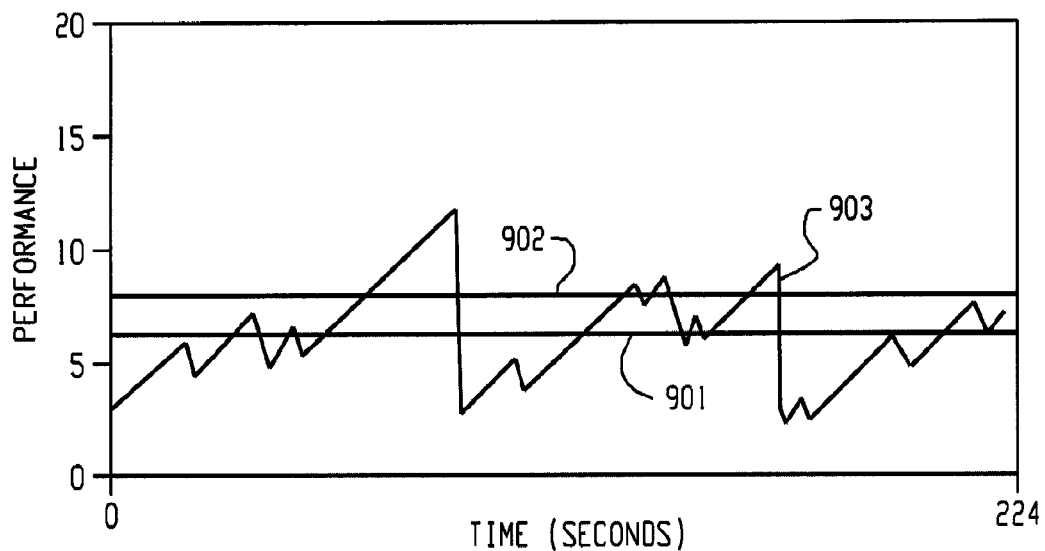
FIG. 9A illustrates an example play pattern of an exemplary individual study participant from a version of the cognitive training program that does not have lower or upper limit bound constraints to ensure play between the user's current and target performance range.

FIG. 9A shows the data from the individual that trained on an earlier version of Project: EVO without the upper/lower bound constrains. As can be seen from his performance trajectory (903), the individual deviates far below and far above his intended performance range between the starting difficulty level (901) and the ending difficulty level (902) making the training to easy or too difficult respectively.

Figure 9B:
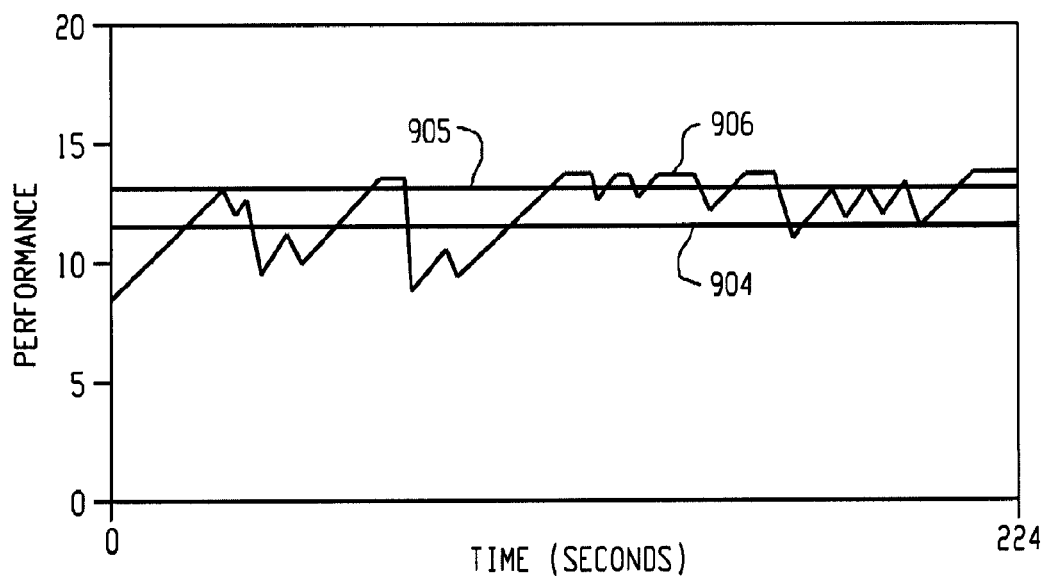
FIG. 9B illustrates an example play pattern of an exemplary individual study participant from another version of the cognitive training program that includes lower and upper limit bound constraints to ensure play between the user's current and target performance range, in accordance with one embodiment in the present disclosure.

FIG. 9B shows data from the individual who trained on an advanced version of Project: EVO that incorporated the upper and lower bound constraints. The individual's overall performance (906) does not deviate significantly below the starting (904) and above the ending (905) training difficulty levels indicating an optimally challenging training.

Figure 10:
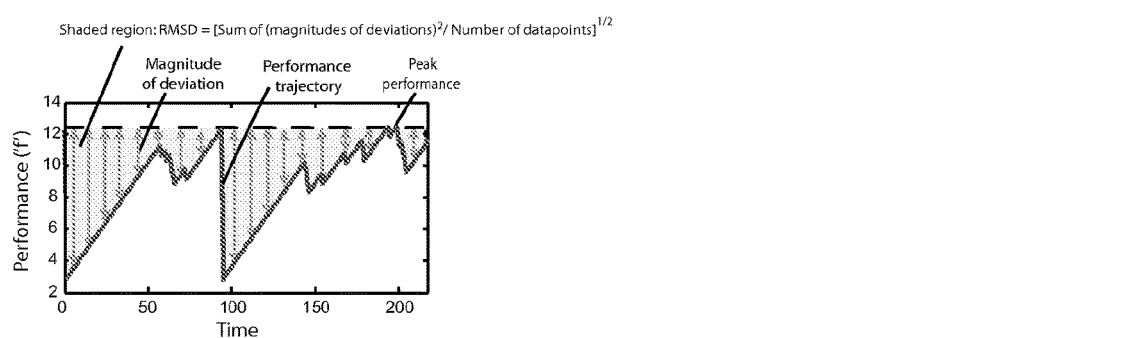
FIG. 10 depicts an example diagram showing how close or far (expressed as RMSD) an exemplary set of study participants samples performance values in a training session relative to their peak performance on a version of the cognitive training program that does not have lower or upper limit bound constraints versus another version of the cognitive training program that includes lower and upper limit bound constraints, in accordance with one embodiment in the present disclosure.
Figure 10:
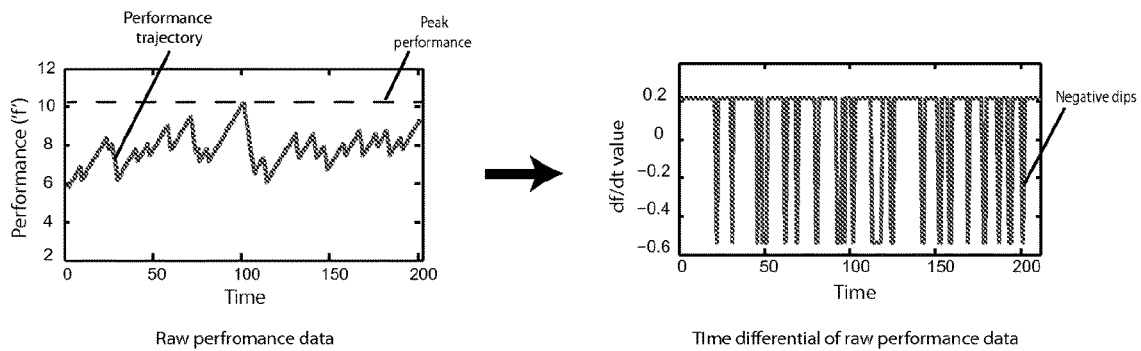

FIG. 10 illustrates how far the performance of an exemplary set of study participants deviates from their peak performance during a training session on an early version of Project: EVO that did not have lower or upper limit constraints on performance versus on an advanced version of Project: EVO that incorporates lower and upper bounds on performance, in accordance with one embodiment in the present disclosure. The magnitude of deviation of performance from the peak performance is calculated as the root mean square difference (RMSD) between the two values over the individual's performance trajectory over time (shown in FIG. 10B). Greater RMSD values indicate larger deviations in the participant's performance to difficulty levels significantly above or below his/her peak performance level indicating sub-optimal training that is either too challenging or too easy. As shown in FIG. 10A, incorporation of bounds on the performance levels an individual is allowed to sample, significantly reduces deviations from peak performance on the Navigation task in the advanced version of Project: EVO. This ensures that the participant maintains a consistent and challenging pace of training A suitably challenging pace of training is also evidenced as rapid and frequent turnarounds/reversals in performance values near the participant's peak performance (illustrated in FIG. 10C), compared to a less challenging training regimen that initiates or drops performance to a difficulty level that is too easy for the participant (illustrated in FIG. 10B). The later results in large, positive accelerations in performance with few reversals as the individual rapidly builds performance to higher difficultly levels that are more suitable to his/her current ability. Reversals in performance values can identified as 'dips' to negative values in the time differential of performance (shown in FIG. 10C). A higher percentage of negative dips are observed on the time differentials of performances on the Navigation task for participants that trained on the advanced version of Project: EVO, compared to the earlier version (tabulated in FIG. 10A). Therefore, incorporation of the upper and lower bounds on performance in accordance with the methods in the present disclosure, results in more challenging training.

Figure 11A:
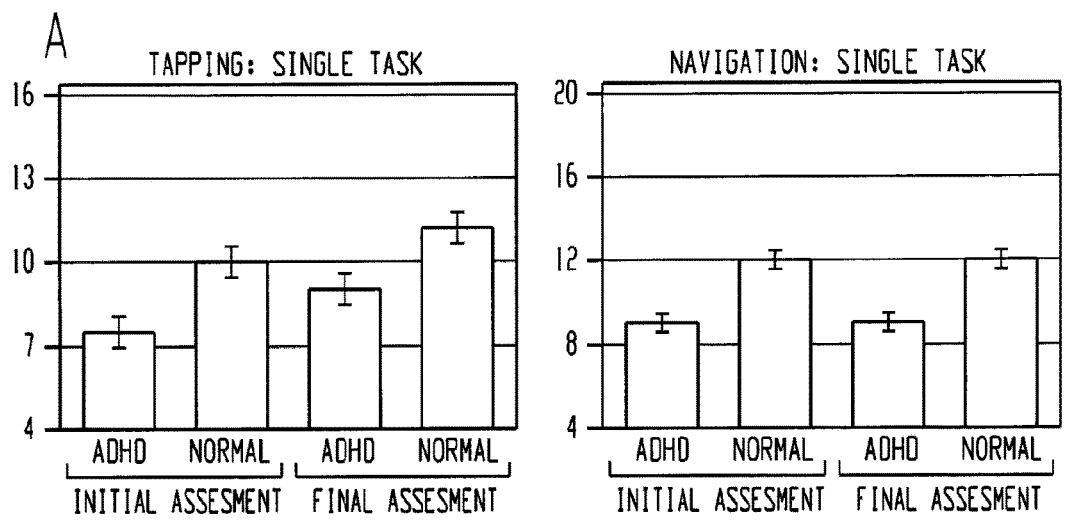
FIG. 11 is an example results summary from participants in an ADHD study who trained on the cognitive training program developed in accordance with one embodiment in the present disclosure.
Figure 11B:
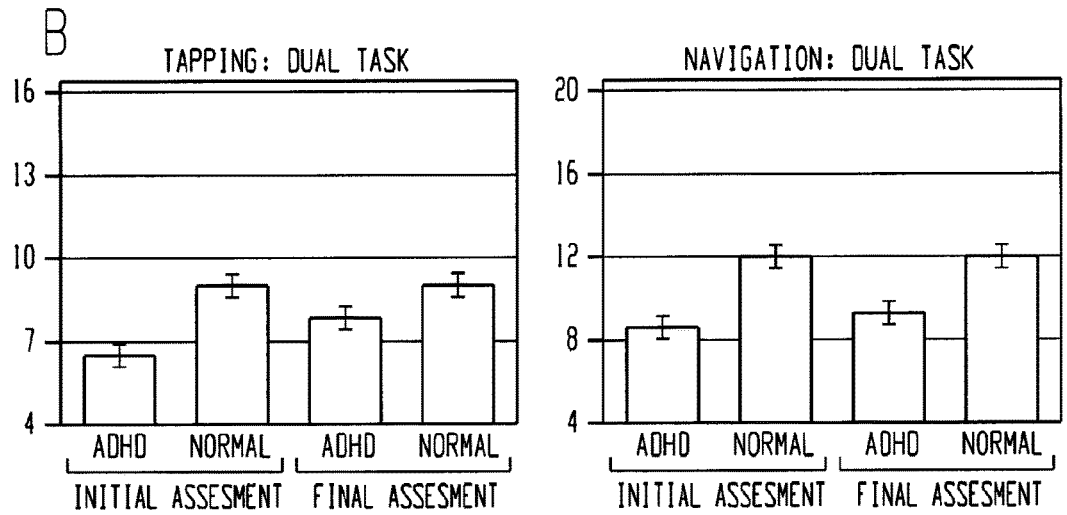
Figure 11C:
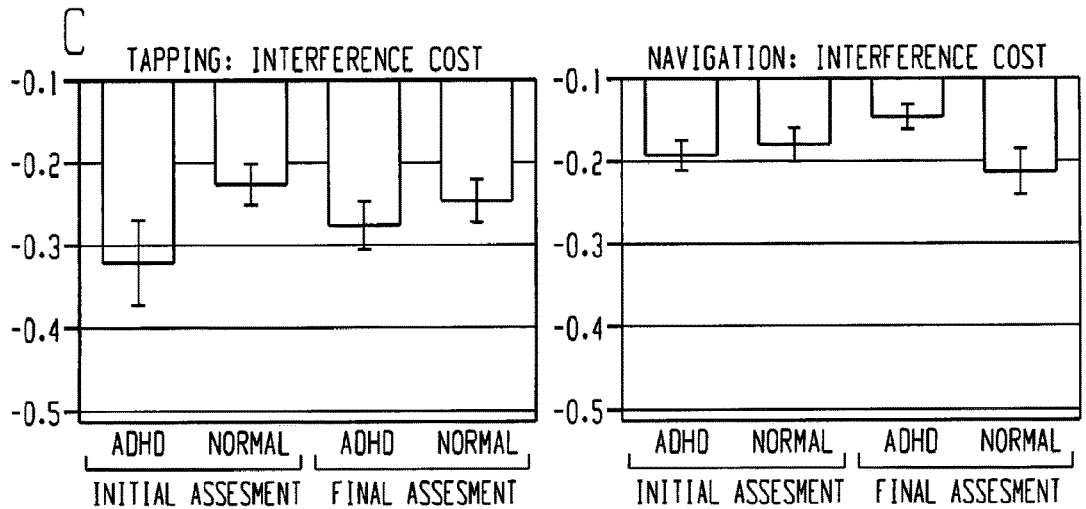

FIG. 11 summarizes results of a pilot study conducted in a pediatric ADHD population that trained on the cognitive training game "Project: EVO" developed in accordance with one embodiment in the present disclosure. The participants' cognitive abilities were measured on the EVO system and on clinical gold-standard assessments for cognition and executive function, both before and after a 4 week training session on Project: EVO. FIGS. 11A-B demonstrate that both ADHD and control groups showed significant improvements in their general abilities on the Tapping and Navigation tasks when performed in isolation (11A) or simultaneously (11B). FIG. 11C illustrates the improvements observed in the interference processing costs experienced by both groups in the initial assessment and after the 4-week training period. FIG. 11D tabulates measurements on the TOVA and CANTAB clinical evaluation scales for cognition for the ADHD group. The group showed significant improvements in attention (measured by the Std. Deviation of Reaction Time on the TOVA), memory (evaluated by the Spatial Working Memory i.e. SWM measures on CANTAB) and impulsivity (evaluated by the Impulsivity indices on the TOVA), after the 4-week training period on Project: EVO. The results demonstrate that Project: EVO significantly improves cognitive and multitasking abilities, which are transferrable to broader, real-world cognitive measures.

The system and methods described herein are not to be interpreted as limited, in any way, to cognitive training regimens. Cognitive training is to be understood as one illustrated embodiment in the present disclosure, representative for teaching one skilled in the art to employ the systems and methods disclosed herein for the personalization and improvement of adaptive training protocols.

DEFINITIONS

When describing the methods and systems of the present disclosure, the following terms include the following meanings unless otherwise indicated, but the terms are not to be understood to be limited to their accompanying meaning as rather it is to be understood to encompass any meaning in accordance with the teachings and description of the present disclosure.

The term "task," as used herein, refers to any method or process of presenting a stimulus to an individual and receiving a response to the presented stimulus in order to complete a goal. The function of the task is to measure or improve the individual's general ability or skill level in a specific or related cognitive or noncognitive domain represented by the task.

The term "training," as used herein, refers to a series of modules or time based segments of one or more specific tasks that an individual is instructed to accomplish with the goal of improving the individual's function or ability in a specific or related cognitive or non-cognitive domain represented by the tasks.

The term "personalize," as used herein, refers to any method or process of customizing the training presented to an individual to the individual's current baseline and desired skill level in a specific cognitive or non-cognitive domain. Personalization may be achieved by adjusting the range of difficulty levels and difficulty progression, or the rewards experienced by the individual during training. The function of personalization is to maximize the improvement in skill level and the engagement experienced by the individual during or as a result of the training.

The term "difficulty," as used herein, refers to any parameter relating to the stimulus presented to the user during a task or the user response that correlates to the complexity or challenge associated with achieving a successful outcome.

The term "level," as used herein, refers to the discrete difficulty values associated with a specific task. Each difficulty level corresponds to a specific increment in a parameter related to task difficulty or complexity.

The term "performance," as used herein, refers to the responses received from an individual to a stimulus provided on a task by the method and system of the present disclosure, which provide a measure of the individual's current abilities or skill level with relation to the presented task.

The term "performance range" as used herein, refers to the personalized range of task difficulty levels that an individual is allowed to sample during a training regimen presented according to the method and system of the present disclosure.

The term "rewards," as used herein, refers to any positive feedback presented to the individual by the system and method of the present disclosure, to indicate progress, recognize performance, or provide motivation to complete the assigned task(s) during assessment or training. Rewards may be provided in an auditory, visual, haptic or any other suitable sensory form.

Methods

The present disclosure features a new system for the implementation of efficient cognitive training of an individual, which employs a personalized difficulty and reward progression based on the individual's own abilities and performance. In certain embodiments of the present disclosure, the range of difficulty levels are modulated based on the most recent in-program assessment of the user's abilities, and progression through a specific range set by the computational system is marked by rewards that the user experiences as he/she reaches the various difficulty levels. Further, certain embodiments of the present disclosure comprise repeated assessment-training cycles as the individual progresses through the training regimen, in order to customize the training difficulty levels, progression and rewards to individual's most recent cognitive abilities. Additionally, the difficulty levels an individual is permitted to sample during training are bound by lower and upper limit constraints to ensure a continually challenging and efficient training regimen. It is appreciated that each of these methods, described in detail in the below sections, can be implemented independently to personalize and improve the efficiency of an adaptive training regimen. Alternately, the described features can be combined into a comprehensive, integrated platform for efficient cognitive training.

Assessment

An assessment, as described in the present disclosure, refers to a phase of the system that makes measurements of the individual's performance and is not intended as a training regimen. The assessment phase is a component of the present disclosure, as the assessment is the general term used herein to refer to the portion of the cognitive training method and system that allows for determination of an individual's cognitive performance or abilities. It is this measurement, or alternatively a combination or manipulation of multiple such measurements, which is used to personalize and set difficulty levels in the training portion of the cognitive training of an individual, according to the present disclosure. An assessment can refer to any of a variety of methods known to one skilled in the art to measure an individual's performance on a cognitive task, which in some embodiments in the present disclosure are responses to a stimulus provided by the cognitive method and system. Measurements may be made by simple static measurements of performance (for example, the percentage of stimuli that were responded to correctly over a given time period) or may be more complex (for example, the convergence value of signal detection performance as derived from a maximum likelihood estimation method using an adaptive algorithm). Methods of measuring such cognitive tasks in simple cognitive assessments can be found in literature such as U.S. Pub. No. 20070299319A1, Chan S C and Hardy J L and U.S. Pub. No. 20050175972A1, Goldman D et al., which are hereby incorporated by reference. In an embodiment in the present disclosure, and by way of specific example, the measurement of the cognitive task entails the reaction time at which an individual responds to a visual stimulus, as determined by the convergence value from a stimulus-by-stimulus staircase method, for example a 2:1, 3:1, or 4:1 step-size-after-incorrect-response: stepsize-after-incorrect-response. It is appreciated that the assessment may be a fully separate phase (i.e., different time) than training, or in some cases the assessment can be made at the same time that the individual is performing the training regimen.

As mentioned above and described in detail below, it is an aspect of the present disclosure that the training difficulty of an individual is tied to, or personalized based on, the individual's assessment. It is appreciated that there are many methods by which an individual's assessment may be used to personalize the individual's training difficulty. Some general examples and specific guidelines are outlined in the below sections "Performance Range", "Difficulty Level and Progress Gates", and "Difficulty Progression."

Performance can be measured by a variety of methods known in the art and the cognitive literature to determine an individual's abilities or skill level with relation to a cognitive task. Performance may be calculated by a single measurement of performance on the task, such as peak performance, mean, median or mode performance, or low performance. Additionally, performance may be calculated over multiple data points or sessions, for instance means or medians or modes of previous sessions, standard deviations or fractional standard deviations above or below averages, etc. Additionally, performance may not be directly measured in full by an assessment of the individual's performance on the cognitive task. For example, the assessment of performance may include comparison with and modulation of a performance level based on normative data or aggregate data of performance by other individuals on the same or similar cognitive tasks or measurements of similar underlying cognitive systems.

It is an embodiment of the present disclosure that the difficulty of an individual's cognitive training regimen is based on the recent assessment. i.e., in order for the cognitive training to be efficient, the cognitive training difficulty should be informed by an assessment that is proximal to the training and therefore generally representative of the individual's abilities when they begin training. It is appreciated that a "recent" assessment may be defined in a variety of ways that approximate an individual's abilities when they begin training. In an embodiment of the present disclosure, the difficulty levels in training are set based on the individual's performance as measured by the latest and most proximal assessment made of the individual before the individual begins training. Alternatively, recent assessment may mean a recent, but not the most recent assessment, for instance the performance measured at the second or third most recent assessment. It is appreciated that a recent assessment may be made to include more than a single assessment. For instance, in one embodiment of the present disclosure performance of an individual that is used to set training difficulty is a weighted average of the three most recent assessments. Various averaging or composite methods may be used that take into account data from assessments at multiple time points. Additionally, in certain embodiments the assessment may not be separate from the training. For example, in one embodiment of the present disclosure, the individual's performance during an initial, defined part of the training run may be used as assessment to set the training difficulty for the remainder of the training.

An assessment is performed to measure the individual's baseline performance on a cognitive task. In essence, the individual's baseline performance can give an estimation of the individual's current performance on the task being measured. Baseline performance is generally directly measured by an assessment, and may be calculated by a variety of methods as described above. The baseline performance may be calculated by one assessment or by more than one assessment (for example, the 2 or 3 most recent assessments), and may be made by simple averaging, weighted averaging, or other mathematical manipulations.

The individual's maximal performance is also measured. In essence, the individual's maximal performance is an estimation of the top performance that the individual might be able to achieve on a task after a reasonable period of cognitive training, for example 1 week or 1 month. The maximal performance of the individual is a target ability to push the individual towards during training. In some embodiments, the maximal performance is the absolute top difficulty level that an individual has been able to reach whereas the baseline performance has been a lower level of performance (for instance an average or converged value of an adaptive algorithm such as a single staircase). Such a performance level may have been calculated in a single or across multiple assessments. In some cases, an individual's maximal performance is determined by how well the individual performs a task in a specific situation deemed to be easier than another situation, with the goal of having the individual, with appropriate training, eventually be able to match that maximal performance while in the more difficult situation. In one embodiment, maximal performance is determined by an individual's performance on a task while in an isolated environment, while the individual's baseline performance is determined by his/her performance in a distracting (for example, visually stimulating and loud noise) environment. In an embodiment, the maximal performance on a task is determined when the individual performs that single task, whereas the baseline performance is how the individual performs that same task when performing it with a second task (i.e., in a dual-task situation).

An individual's maximal performance may be more difficult to determine than his/her baseline performance if it is not directly calculated by the individual's performance. For example, the maximal performance may not be a performance level that the individual has ever reached, but rather a level that he/she may be able to reach with training. For example, maximal performance may be calculated as an extension or extrapolation, for example linear extrapolation, of the individual's performance data. Alternatively, maximal performance may be determined entirely indirectly, for instance by using data distributions from normative data curves or comparison data of individuals performing the same or similar task. For example, a 45-year-old individual with ADHD may have an average response time in a signal detection task of 600 ms. The maximal or target performance for that individual may be chosen as the average 45-year-old performance on that cognitive task in a neurotypical (i.e., non-ADHD) population, or the average 35 or 25 year-old's performance in the task in ADHD populations, or the average maximal performance attained by other 45-year-old ADHD individuals with similar baseline performances, after a reasonable period of training.

It is appreciated that the exact timing, relative to the training regimen, that the assessment is performed, can be one of a variety of potential alternatives. For example, the assessment may be made one week or one month before a training regimen is started. Alternatively, in an embodiment of the present disclosure the assessment of the individual is made immediately (i.e., within minutes) of when the individual begins his/her training regimen. As described above, the assessment values that program training can be from one or multiple assessments.

It is also appreciated that the location of where the individual performs the assessment can take various potential options. For instance, the individual may perform the assessment in the same physical location that he/she performs the training. Alternatively, the individual may perform the assessment and training in very different environments. With respect to the computer system, the individual may perform the assessment in the same computer program as the training regimen. In some embodiments, it is appreciated that the system may actually make the assessment a calculation of a portion of the individual's performance data during the training phase itself. In such an instance, in essence there is no difference between training phase and assessment phase, the difference is the data used. Alternatively the individual may perform the assessment in an entirely different computer program, or in fact not in a computer program at all.

It is envisioned in the present disclosure that in some embodiments the assessment should be the measurement of an individual on a cognitive task that is similar in nature to the task being performed in training. The assessment gives a representative determination of the performance level on training Therefore, the task may be exactly the same as the training task, it may be an altered version of the training task, or it may be an entirely different task than the training task but similar in the cognitive functions that it measures. Alternatively, in some embodiments the assessment may be a very different cognitive domain, and therefore can inform an individual or a care practitioner of the generalizability or transfer of benefit of training.

Assessment Cycles

In many cases of cognitive tasks, there are practice effects from early assessments to later assessments. Practice effects can generally include instances when individuals improve at the task through familiarity and learning of the task (for example, comfort with the rules, better handle of the mechanics, etc.) as opposed to improvement through deeper cognitive neuroplasticity. Such practice effects can make the measurement of an individual's cognitive progress or cognitive decline (for example, after a period of time, or after a disease progression, or after a training regimen) difficult to interpret, since the later assessment can show performance that is artificially high, owing mainly to the individual's repeating the task and not a true measure of his/her cognitive state. This effect is appreciated in the art and is usually addressed by 1) requiring an individual to do multiple assessments before counting a "valid" assessment or beginning a cognitive training regimen, or 2) administering one or a few assessments before a training regimen or rest period, but then subtracting a known practice effect population average from the next assessment that is performed. Both of these methods may enable one to compare values of an individual's performance between assessments.

However, while these existing methods address the reliability of the cognitive measurement between assessment periods, they unfortunately do not address the impact that practice effects have on cognitive training; namely that a cognitive training regimen set at a specific difficulty level or even an adaptive difficulty level may become less challenging over time due not to an individual's cognitive progress but rather due to his/her practice effects. In some cases, an individual may even be made to move along to a new cognitive task when the cognitive training system has identified (erroneously) that an individual has mastered a cognitive task. Therefore, cognitive training may not be challenging and efficient for an individual when performing cognitive tasks where there are expected to be substantial practice effects.

In these cases where practice effects are an issue, and more generally when a practitioner wants to ensure that an individual is receiving a constantly challenging cognitive training regimen (such as in the methods and systems of the present disclosure), it may be beneficial to rely on a system that can minimize a decrease in challenge to the individual as he/she learns a cognitive task.

Accordingly, it is an aspect of the present disclosure that multiple assessments are made throughout a cognitive training regimen, each assessment re-setting the difficulty progression and performance range for the subsequent cognitive training phase. Thus, it is envisioned that an efficient cognitive training experience entails a repeating cycle where assessment informs the difficulty progression levels in training, and frequently or infrequently a re-assessment is made, the re-assessment results then being used to set training difficulty range and progression levels, and so forth. The process may be carried out for as many times as necessary to reach an end-goal for the individual, such as a certain cognitive function ability attained or a certain time spent on a cognitive training regimen. A final assessment at the end of such cycles may be useful in determining the overall progress from the beginning of cognitive training through the end of a cognitive training regimen, as measured by assessment phases.

In an embodiment of the present disclosure, the precise schedule of assessment cycles (when during the training regimen a re-assessment is presented to the individual) is tied directly to the individual's personalized difficulty progression levels in the training phase, and is presented to the individual after he/she has performed training at the ending difficulty level during his/her training phase. In a particularly preferred embodiment, the number of assessment-training cycles are pre-defined to be a specific number of cycles (e.g., 3, or 5) before the individual is presented an assessment for a new cognitive training task. Such a subsequent cognitive training task may be a more complex variation of the prior cognitive task or a completely new cognitive task meant to provide new challenge to the individual, such varied or new task also presented with a system of assessment-training cycles as described herein.

Performance Range

An aspect of the present disclosure involves the process by which an individual's training difficulty progression is set in a personalized fashion based on that individual. The difficulty progression (i.e., the increasing difficulty of the cognitive task presented to the user during training, meant to continually stress the individual's comfort level i.e., challenge the individual) can potentially be designed to progress ad infinitum within the bounds of human abilities, however a more practical approach is to have a range of performance levels within which the difficulty progression operates. For example, a difficulty progression may incrementally over time present to an individual a target discrimination task with a response time window changing from 3000 ms to 400 ms as the individual succeeds at each 50-ms-faster response time window. This predefined range is referred to as the "performance range" for the individual. The performance range is the range of difficulty levels from the starting difficulty level to the ending difficulty level that the individual is allowed to sample during a training regimen. In an embodiment of the present disclosure, an individual's performance range is determined during an assessment phase, and a similar or permutation of the performance range is then automatically programmed into the training to define the bounds of the individual's difficulty progression.

The starting difficulty level of the performance range may be set based on a variety of parameters from the assessment. The starting value may be substantially similar to the individual's baseline performance on the task during a recent assessment phase. Alternatively, the starting difficulty level may be some mathematical function of the baseline value from the recent assessment phase, for example a percentage such as 90%, 85%, or 80% of the baseline assessment value. It is understood that a variety of mathematical manipulations of the individual's assessment optionally combined with non-individual data may be suitable for the purposes of the present disclosure.

The ending difficulty level of the performance range may be set based on a variety of parameters from the assessment. The ending value may be substantially similar to the individual's maximal or target performance on the task during a recent assessment phase. Alternatively, the ending difficulty level may be some mathematical function of the maximal or target performance value from the recent assessment phase, for example a percentage such as 120%, 110%, 90%, 85%, or 80% of the maximal or target assessment value. It is understood that a variety of mathematical manipulations of the individual's assessment optionally combined with non-individual data may be suitable for the purposes of the present disclosure.

As long as the performance range is specific/personalized to the individual being assessed and undergoing training, and as long as the performance range covers some portion of the individual's current or reasonably expected abilities, a variety of potential performance values of an individual obtained in an assessment can serve to define the range. In one embodiment in the present disclosure, a suitable performance range defined in an assessment and used in the subsequent training phase is the range inclusive of and between the individual's baseline performance and maximal or target performance on a given cognitive task.

Other examples of performance ranges include an individual's performance in two different conditions (for instance an isolated quiet condition versus a noisy distracting condition), the individual's performance on two versions of the same task with different complexity, the difference between the individual performing a single task and that same single task while performing a second task (i.e., a dual- or multi-task), the individual's current performance versus a historical maximal performance for that individual, and an individual's average performance versus population averages for individuals of the same or a target population.

In all examples, where there is one condition that is easier (the individual's performance is better) and the goal is to increase the individual's performance in the condition that is harder (the individual's baseline performance is worse), then the "easier" situation may correspond to the starting difficulty level and the "harder" situation may correspond to the ending difficulty level of the individual's performance range.

Difficulty Level and Progress Gates

The results of an assessment of the individual's abilities are used to set the difficulty level at which an individual will begin his/her cognitive training program, as well as the difficulty levels in the cognitive training program that the individual will be motivated to reach. The difficulty may be defined in the cognitive training module as one of various parameters relating to the stimulus being presented and the user response (see section "Stimulus").

It is an aspect of the present disclosure that the personalized performance range of an individual is divided into distinct progress 'gates' identified by specific difficulty levels that the individual may perform at in order to progress in the training module(s). Progress gates may be distributed at discrete intervals of performance range or may be continuous. In an embodiment of the present disclosure, the individual's personalized performance range is divided into a set of discrete progress gates. A starting progress gate is set at the difficulty level corresponding to the individual's current baseline performance and an ending progress gate is set at the difficulty level corresponding to the individual's target maximal ability. Intermediate progress gates between the starting and ending gates are set at are discrete performance levels, the magnitude of the difficulty increase between each gate being a function of the individual's assessment and performance range. For example, Subject A may be presented by the system of the present disclosure a personalized performance range for response window to a discrimination task from 1000 ms to 600 ms, with progress gates set at 100 ms incremental increases in difficulty. Therefore, Subject A has 5 progress gates: A starting progress gate at the starting difficulty level (1000 ms), an ending progress gate at the ending difficulty level (600 ms) and 3 intermediate progress gates at intervening difficulty levels (900 ms, 800 ms, and 700 ms), that he/she may perform at in order to successfully complete training Subject B, performing the same task but at a much lower overall ability, may be presented by the system a personalized difficulty progression range from 2000 ms to 1000 ms, with a starting progress gate at 2000 ms, ending progress gate at 1000 ms and 3 intervening progress gates at difficulty levels of 1750 ms, 1500 ms, and 1250 ms. Subject C with the same starting ability (1000 ms) as Subject A, but a lower target maximal ability (700 ms), may be presented by the system a personalized performance range from 1000 ms to 700 ms. The progress gates for this individual may be set in one of two ways: (i) The performance range may be divided into 4 progress gates set at each 100 ms incremental increase in difficulty. Therefore, Subject C would be presented with a starting progress gate at 1000 ms, ending progress gate at 700 ms and 2 intervening progress gates at difficulty levels of 900 ms and 800 ms. (ii) Alternately, the system may present to Subject C, the same number of progress gates as Subject A, but alter the difficulty increments between the gates. In this case, the performance range for Subject C would be divided into 5 progress gates set at each 75 ms incremental increase in difficulty, with a starting gate at 1000 ms, ending gate at 700 ms and 3 intervening gates at difficulty levels of 925 ms, 850 ms and 775 ms. Thus, where previous cognitive training systems would provide Subjects A and C with identical training regimen based on their similar baseline cognitive abilities, the system of this present disclosure would enable a more efficient cognitive training of each Subject across their full dynamic range by tailoring the training difficulty levels and progression to their individual maximal capabilities.

The incremental difficulty levels corresponding to the progress gates between the starting and the final difficulty level may be obtained by a variety of methods suitable to the present disclosure. In one embodiment, the incremental progress gates are set based directly on various performance levels at which the individual performed during the assessment. For example, the individual may have sampled, increasingly less frequently than the baseline performance level, a variety of difficulty levels that can be used for the incremental progress gates, as long as they are between the starting and ending level and in a logical succession of difficulty.

Alternatively, the incremental progress gates may be calculated to be a distribution between the starting difficulty level and the ending difficulty level. It is understood that the exact method in which successive incremental progress gates are distributed may include a variety of mathematical manipulations known in the art as methods to divide a range of values. For example, the range, which in the case of the present disclosure may be a performance range, may be divided into equally distributed (i.e., linear) increments between the bounds of the performance range, for example between the starting and ending difficulty levels. Other nonlinear division methods of the range, such as hyperbolic, parabolic, exponential, sigmoidal and the like are suitable and may be beneficial for certain cognitive tasks or certain individuals. The system may also use methods known in the art for analyzing large datasets (Hastie, T. et al., The Elements of Statistical Learning, 2nd Edition, Springer: 2009), and leverage ongoing or previously collected data from the cognitive training progression and success of other individuals or groups of individuals on the same or similar tasks, to determine the most beneficial course incrementing method for an individual and apply that method to the individual's personalized performance range. Standard data mining procedures including supervised and non-supervised learning approaches, unbiased data component analyses such as factor analysis or principal component analysis and other approaches to describing emergent patterns in data and predictor variables for group classification can all be suitable to the present disclosure.

It is an aspect of the present disclosure that the starting, incremental intervals, and ending difficulty levels are all personalized to the individual by being a function of the individual's performance on one or more recent assessments. In an embodiment of the present disclosure, the progress gates are distributed across the individual's performance range, between the individual's last baseline and target level, as determined in the assessment. For example, if the previous assessment determined the individual to be performing at an average response time of 800 ms, but that the individual's maximal or target level response time attainable was 500 ms, the progress gates corresponding to the difficulty of the response interval in training may be set as, for example, 5 or 10 increments of average response time distributed between 800 ms (lowest difficulty level) and 500 ms (most difficult level). In an embodiment, the task being assessed and trained is a dual-task, and the range across which the progress gates are distributed is where the starting gate is set at the dual-task performance on the recent assessment, the ending gate is set at the single-task performance from the recent assessment, and one or more intervening progress gates are evenly distributed at difficulty levels between the starting and ending difficulty level.

Additionally, in training regimens that employ dual-tasks or multi-tasks, the difficulty levels and progress gates for the difficulty progression of the training regimen may be defined by a combined measure of the difficulties on individual tasks. It is to be understood that various composite methods and mathematical manipulations of individual task difficulties may be employed to define the combined task difficulties tied to specific training difficulty levels representative of the progress gates. In one embodiment, in a dual-task situation, the user may need to simultaneously hit progress goals for both tasks in order to complete a corresponding progress gate. In another embodiment, in a dual-task situation, the user may need to simultaneously hit respective thresholds for both tasks in order to complete a corresponding progress gate. For example, a user may exceed the threshold of one task but still not hit the threshold of the other task. Thus, the progress gate cannot be completed.

Difficulty Progression

In general, the difficulty level progression in the cognitive training system and method of the present disclosure begins with a starting difficulty level at which the individual may succeed, followed by incremental increases in the difficulty levels (gates) at which the individual may perform to advance, and ending with a final difficulty level at which the individual may perform to complete the training module and/or to advance to further modules or phases or cognitive tasks of the training program. In an embodiment of the present disclosure, the ending difficulty is used as the level of performance after which the individual is made to have a re-assessment and re-set the training performance range and difficulty progress gates for subsequent training, thus having the effect of more finely tuning a training difficulty to the individual's changing baseline over time and providing a solution to overcome practice effects.

As should be clear from the above description, it is envisioned that an individual does not receive a higher difficulty level (presentation of the stimulus) during the training task until he/she has performed at the difficulty level corresponding to the most proximal progress gate to his/her current performance. The way in which the system and method of the present disclosure qualifies whether an individual has succeeded to perform at a given difficulty level acceptable enough to trigger the progress gate can come in various forms and may depend on the type of cognitive test and the desired success criteria. For example, for tasks that are traditional tests with clear performance measures on each stimulus (such as a reaction time task or a flanker task), the individual may succeed at a given gate by reaching the difficulty level corresponding to the gate for a single or very few stimulus events, by holding the given difficulty level for multiple events or for a predetermined time or until an adaptive algorithm senses convergence at that level, or by exceeding the gate difficulty level by some increment for a short or long period of stimuli or time. For tasks that are more complicated and judged by performance on a series, success can mean completing or nearing completion on a sequence of tasks. In some cases, success at a given progress gate may cause the system to observe performance at that difficulty level (including as described above) multiple times over one or more periods of time such as hours or days, or under multiple conditions, in order to ensure that the individual can reliably perform at the given difficulty level.

Lower Limits.

In some cases, individuals may not be allowed to sample difficulty levels that are significantly below that which they have most recently attained. In essence, the training program can apply a lower bound or a "floor" to the difficulty levels that an individual samples during training Such an action by the system or method may ensure that an individual with an uncharacteristically poor performance (such as being distracted, or dropping the training device, or having a very poor day) does not receive subsequent performance that is too easy and at a level that is not suitably challenging, the next session leading to an inappropriately slow training pace, as has been observed in traditional adaptive algorithm approaches. In one embodiment, once an individual is able to perform at a specified difficulty level, the cognitive training program may no longer offer a significantly lower difficulty level during subsequent training Such a difficulty "floor" may be set at a percentage of the difficulty, such as 95%, 90%, 85%, or 80% of the difficulty level that the individual has currently reached. For example, once a user is able to perform a target discrimination task at an average reaction time of 500 ms, corresponding to a level of 20 in the cognitive training task, the cognitive training algorithm may not allow the user to sample levels below 19, 18, 17, or 16 during subsequent training.

Upper Limits.

In some cases, individuals may not be allowed to sample difficulty levels that are significantly above that which they have most recently attained. In essence, the training program can apply an upper bound or "cap" to the difficulty levels that an individual samples during training Such an action by the system or method may ensure that an individual with an uncharacteristically high performance (such as having taken a cognitive enhancer, or being in an unusually quiet and sterile environment, being excessively cognitively aroused for any of a number of reasons) does not receive subsequent performance that is too difficult and have an inappropriately increased training pace In one embodiment, the cognitive program may not offer a significantly higher difficultly level than the one experienced by the individual in a recent training regimen. Such a difficulty cap may be set at a percentage of the difficulty, such as 110%, 115%, 120% or 125% of the difficulty level that the individual has currently reached. For example, once a user is able to perform a target discrimination task at an average reaction time of 500 ms, corresponding to a level of 20 in the cognitive training task, the cognitive training algorithm may not allow the user to sample levels above 23, 24, 25, or 26 during subsequent training.

Plateau.

It is envisioned that the difficulty progression stays the same during many training cases. However, in some instances it may be favorable for the difficulty progression to automatically adjust or change dynamically in response to an individual's behavioral pattern, for instance to combat decreasing adherence by an individual by providing variability in the training experience. Alternatively, such a change in difficulty progression may be activated as the system's response to an individual who has plateaued and is apparently no longer able to improve their cognitive function. In these cases, it may be beneficial to enable an individual to pass the full ending difficulty level by changing the difficulty levels of the remaining increments and the ending difficulty level. In an embodiment, each time the system registers a pre-defined pattern of plateauing behavior, such as 10 or more sessions played in a row with no improvement in performance, the system can change the next difficulty level increment to exactly match the level at which the user is currently performing. In this case, the system accommodates the user and allows progression through the regimen without making the training feel too easy and still keeping the individual in a challenging and efficient training zone.

It is appreciated that the various parameters of the cognitive training regimen, such as the number and timing of re-assessments, the training performance range including the starting and ending difficulty levels, the training difficulty progression including the number and placement of progress gates and the upper and lower limit constraints on the individual's training performance, can be implemented by the system of the present disclosure by one of a variety of alternative methods. In some embodiments, these parameters can be automatically programmed by the computational system based on the individual's recent assessment(s) and performance. In some embodiments, these parameters may be interactively assigned by an instructor or caregiver of the individual performing the training. In other embodiments, a combination of the above methods may be utilized, in which the training parameters are automatically assigned by the computational system, but their values can be dynamically updated or modified by an instructor or caregiver during an ongoing training regimen.

In some cases, it may be beneficial for an individual to receive feedback on the actual value of his or her performance and progress. This could include the actual value of the difficulty level or progress gate achieved by the individual, or a different numerical representation. In an embodiment of the present disclosure, progress is represented as a simple number, the integer corresponding to the difficulty of the cognitive task achieved by the individual. For example, in a reaction task, the level may be represented as a simple number between 1 and 30, where each successive integer is representative of a drop in the response interval in which individual can register a correct response for the stimuli being presented, for example 50 ms intervals. As another example, the average response interval for the stimuli being presented may be transformed into a much more high-resolution level, such as Level Number=6000/(current average reaction time of the stimulus), and the level number is rounded to the nearest integer, or rounded to the nearest value in the tenths or hundredths decimal place.

However, it is not necessary that the individual has a numerical understanding of his/her performance. The difficulty level and progress experienced by an individual may be represented by a variety of modalities, including numerically, pictorially, auditorially or by other modes that signify to the individual how well he/she is performing. It may be represented by simple figures or pictures or charts, which signify to the individual that he/she is progressing and not by what magnitude. In certain embodiments of the present disclosure, the difficulty level is represented by a simple image with a generally positive connotation, such as a star as shown in panel 511 in FIG. 5F. In some cases, progress is distinguished by emphasizing the image differently at different progress gates. For example, the star may be given a stronger emphasis, including being made brighter, or larger, or more colorful, for each next gate at which the individual can strive to perform.

Rewards

Rewards can be a part of any training regimen, as they may engender increased enthusiasm to engage in the regimen, resulting in increased compliance and probability of completion. Additionally, rewards that motivate the individual to give their true effort to a game (as opposed to completing a task but not really trying), can have a significant impact on training. If an individual is not putting forth effort, then any adaptive system that advances the individual through training based solely on time on task may be presenting to the individual tasks of a difficulty that are not challenging and therefore not targeting the individual's core cognitive capacity. Additionally, rewards that are generally recognized as motivating but are not tied to the individual's performance and prescribed difficulty level (for example, progress bars or rewards upon completing a set time spent on training) may not ensure that the user is completing the training at a level challenging to him/her, and may in fact be de-motivating if an individual senses that the reward (for example, "Great job" congratulations) do not match the effort put forth, creating a sense of falseness in the training mechanics. Unfortunately, many current systems fail to provide solutions to these problems.

Accordingly, it is an aspect of the present disclosure that the cognitive training algorithm for presenting a personalized difficulty progression to an individual can additionally include rewards which are directly tied to such personalized progress gates. Being personalized enables different individuals to experience all rewards, since they are set based on the individual's personal difficulty progression levels and not an absolute scale. Therefore, there may be a standard set of rewards that are set for difficulty progression increments, and therefore attainable by all individuals regardless of their varied abilities on the task. For example, Subject A may be presented by the system a personalized difficulty progression range for response window to a discrimination task from 1000 ms to 600 ms, with incremental difficulty progress gates set each 100 ms (i.e. at 1000 ms, 900 ms, 800 ms, 700 ms and 600 ms). Subject B, performing the same task but at a much lower overall ability, may be presented by the system a personalized difficulty progression range from 2000 ms to 1000 ms, with 5 progress gates set at 2000 ms, 1750 ms, 1500 ms, 1250 ms and 1000 ms. If the system rewards the Subjects for passing each incremental progress gate 1 through 5, for example with a visual Star on a computer screen, then each subject, despite their very different functional levels, can be similarly motivated and achieve the same rewards based on his/her completion relative to his/her own personalized difficulty progress. The system therefore enables each user to be motivated, make progress, and receive rewards based on performance relative to their own abilities as opposed to comparisons with standards that may not apply to them. In an embodiment in the present disclosure, the method and system presents rewards that are directly tied to the individual accomplishing incremental difficulty levels specified as progress gates within his/her performance range, and in a particularly preferred embodiment the rewards are given for performance distributions across the range encompassing the individual's baseline performance and maximal or target performance.

It may be preferable in some cognitive training situations for the reward to serve as the metric of cognitive abilities of the individual, such that the individual is focused solely on attaining the reward. In an embodiment of the present disclosure, the system presents to the individual rewards corresponding to the difficulty levels at which he/she succeeds, and does not receive numerical or more specific data related to his/her cognitive function. Rewards in the present disclosure can be differentially emphasized to give the individual a sense of how far they have accomplished. For instance, a visual reward such as a star may appear differently to the individual at each subsequent increasing progress gate, for instance in shape or size or brightness. Emphasis can be visual, auditory, tactile, olfactory, taste in nature. Additionally, emphasis can change based on the timing of the reward, the closeness to the attained difficulty level, or any number of similar parameters.

It is understood that many types of rewards previously known in the art can be suitable for the present disclosure. The nature of the rewards can be visual, auditory, or of another sensory modality, as commonly used in tasks that are difficult but that may need motivation. Rewards used in such common activities as video or computer games, educational software, athletics, or other similar techniques that use motivation to complete a task are suitable. Examples of suitable rewards have been previously detailed in U.S. Pat. No. 8,343,012B2, Redmann W G, U.S. Pat. No. 6,585, 518B1, Jenkins W M et al. and U.S. Pub. No. 20130091453A1, Kotler M J et al., which are hereby incorporated by reference.

It is appreciated that the exact criteria and timing of providing rewards to an individual during a training regimen, can be one of a variety of potential alternatives. Rewards can be delivered on a set schedule tied to an individual's performance and progress through the training regimen. For example, rewards may be delivered when a progress gate is achieved (i.e. the individual performs at a difficulty level specified by a progress gate). It is an embodiment of the present disclosure that rewards are delivered when an individual maintains performance at a difficulty level specified by a progress gate for a predetermined period of time. Other criteria such as time to advance to the next incremental progress gate, total duration of performance at a progress gate, time spent engaging with the training regimen, number of tasks completed or number of training modules completed may all be suitable criteria for the personalized delivery of rewards. Furthermore, rewards may be pre-programmed into the computational system, or may be interactively and dynamically assigned and modified during a training regimen.

Stimulus

The present disclosure features a method and system for enhancing cognition in an individual, entailing providing cognitive assessment and cognitive training to an individual. The assessment and training are meant to measure and improve, respectively, an individual's cognitive function or general ability. Both the cognitive assessments and training of the present disclosure entail presenting to the user a cognitive task. Any cognitive task that presents a stimulus to an individual, and receives a response of the individual to that stimulus in order to complete a goal, can be classified as a cognitive task. It is noted that various types of cognitive tasks may be used for the methods and systems of the present disclosure, since the present disclosure broadly discloses a method to present efficient cognitive training to an individual independent of the specific cognitive training task and sensory modality. Therefore, any of the many definitions of cognitive tasks known in the art are suitable for use in the present disclosure.

A cognitive task preferably has a stimulus to the user, various types of stimuli having been characterized previously in the art. Art such as U.S. Pub. No 20070299319A1, Chan S C and Hardy, describe suitable stimuli for a cognitive task and the response by a user, as well as the fact that stimulus presented to an individual may change or adapt for a variety of circumstances. These disclosures in the art are hereby incorporated by reference.

Additionally, the method and system of the present disclosure are suitable for the assessment and training of individuals in non-cognitive domains such as emotional and social intelligence, physical ability, and knowledge of educational materials. In these instances, the user may be presented with non-cognitive tasks, comprising stimuli that receives a response from the user based on his/her skill in the domain under evaluation. For example, during physical training, a user may be presented with a stimulus that receives a response in the form of a motor movement. Assessment and training of emotional and social intelligence may comprise tasks that present to a user scenes representative of a social setting, where the goal is to identify and report the emotion conveyed by the scene or the socially appropriate course of action. Therefore, the system and method of the present disclosure can be applied to any set of tasks in any domain, as long as the tasks are representative of the domain under assessment, and improvement of a subject's skill in the domain needs a personalized, adaptive training approach.

Training

The present disclosure details a system and method of enhancing cognition in an individual, which includes presenting cognitive training to the individual. Cognitive training generally refers to a series of modules or time-based segments of one or more specific tasks (i.e., a prescribed regimen) that an individual is instructed to accomplish, with the goal that commensurate with accomplishing the tasks will come a general improvement to the individual in the cognitive task on which he/she trained, or in a related cognitive ability. In certain embodiments in the present disclosure, the cognitive training regimen is presented as a computerized set of tasks, and in a particularly preferred embodiment the cognitive training regimen is presented to the user in an engaging interactive format.

As noted above, various types of cognitive tasks may be used for the methods and systems of the present disclosure, since the present disclosure broadly discloses a method to present efficient cognitive training to an individual independent of the specific cognitive training task and sensory modality. Therefore, the present method and system can also be applied towards the personalization and improvement of the efficiency of existing cognitive training systems.

It is an aspect of the present disclosure that an individual is provided a cognitive training task, with an initial difficulty level and increasing difficulty progression based on that individual's own abilities. For the methods and system of the present disclosure, the individual is kept close to their performance abilities in order to ensure an efficient cognitive training regimen. Certain aspects of the present disclosure related to difficulty progression and reward progression are detailed herein above. However, the specific algorithm or method that can change or alter or adapt difficulty over the training course can be one of a variety of methods known in the art to adapt difficulty during training. For example, methods such as block adaptation, maximum likelihood estimation methods, single- or multi-staircase procedures, and other such methods known in the art. It is the application of such algorithms in the personalized cognitive training method and system described herein that comprise some aspects of the present disclosure.

Target Populations

Individuals that can use the methods and tools of the present disclosure can be any person, especially those interested in enhancing cognitive abilities. For any of the target populations described below, diagnostics to assess one's cognitive ability (e.g. impairment or susceptibility to interference) and training are particularly useful applications of the methods of the present disclosure. It is recognized in the cognitive field that interference in cognitive function severely impacts cognitive performance across a range of functions, including perception, attention, and memory. Accordingly, there are many potential populations that would benefit from a new training method that specifically aims to enhance the ability to deal with interference.

Individuals that can benefit from the subject methods and tools include but are not limited to adults, such as aging adults. For example, the subject methods and tools can be useful for adults that are of any age. It is well-known that healthy aging adults have a significant deficit in processing of cognitive interference. Additionally, recent findings show that even young adults can show signs of such a deficit (Int. Pat. No. WO2012/064999A1 by Gazzaley, A.). Therefore, adults about 30 years old, or older, can benefit from the methods of the present disclosure. As an individual ages, there is a measurable deterioration of his/her cognitive abilities. This experience of cognitive decline may manifest itself as an occasional oversight in various daily activities and/or increasing difficulty in concentration. The decline often progresses to more frequent lapses as one ages in which there is passing difficulty performing tasks requiring extraction of visual or auditory information while multi-tasking or avoiding distractions. Avoiding dangers when driving a car, scanning a crowd for a familiar face, and reading quickly are a few of such examples. Thus, the present disclosure is particularly useful in individuals of any age desiring to improve their cognitive abilities or ameliorate an established decline or the rate of decline in cognitive function.

Such decline typically accelerates starting at age 50, and worsens over subsequent decades, such that these lapses become a noticeably more frequent, in a phenomena clinically referred to as "age-related cognitive decline." While often benign, such predictable age-related cognitive decline can severely alter quality of life by making daily tasks arduous.

Age-related cognitive decline can lead to a more severe condition now known as mild cognitive impairment (MCI), in which sufferers show specific sharp declines in cognitive function relative to their historical lifetime abilities even though the symptoms don't meet the formal clinical criteria for dementia. The subject methods and tools have the potential to reverse and/or prevent the onset of this devastating neurological disorder in humans, such as those suffering or at risk for MCI.

Aside from age-related cognitive decline, people of all ages who experience or are at risk for cognitive impairment can benefit the present disclosure. For example, the present disclosure is useful for training individuals whose cognitive losses have arisen as a consequence of injury (e.g., traumatic brain injury), medical treatments, chronic neurological, psychiatric illness, or of unknown cause. Such cognitive impairment, age related or not, can be a contributing factor or manifesting symptom of a variety of conditions, including Alzheimer's disease, Parkinson's disease, Huntington's disease, depression, schizophrenia, dementia (including, but not limited to, AIDS related dementia, vascular dementia, age-related dementia, dementia associated with Lewy bodies and idiopathic dementia), Pick's disease, cognitive deficit associated with fatigue, multiple sclerosis, post traumatic stress disorder (PTSD), obsessive-compulsive disorder (OCD), and others. Other cognitive losses can include brain damage attributable to infectious pathogens, medical intervention, alcohol or drugs, etc. Thus, cognitive decline or impairment can be a contributing factor or negative influence on a variety of adverse conditions, and thus the present disclosure can be useful in combating or diagnosing anxiety, stress, panic, depression, dysphoria, or malaise. Additionally, cognitive decline may result as a secondary symptom from a variety of disease states that are on the surface unrelated to cognition, but which significantly adversely affect the above-mentioned cognitive processes. Accordingly, individuals experiencing pain or diseases having a significant pain component, insomnia, or adverse effects of disease treatment such as chemotherapy or radiation therapy can also find use in methods of the present disclosure.

In one embodiment, progression through the cognitive enhancement training with adaptive algorithms described in this disclosure can be a diagnostic of cognitive function. The progression through a cognitive training program can be measured in many different ways including, but not limited to, at what stage the user has a plateau, how often a user plateaus during a set of progress gates from one assessment, how often a user plateaus in multiple sets of progress gates from multiple cognitive assessments, etc. When the cognitive enhancing system is used as a diagnostic of cognitive function, it can be used in any of the target populations to track disease progress and monitor progress of a therapy. When the cognitive enhancing system is used to track disease progress, the cognitive training can be initiated on a regular schedule such as daily, weekly, and monthly. When the cognitive enhancing system is used to monitor a therapy, it can be administered before therapy and then on a regular schedule, such as daily, weekly, and monthly. In one embodiment, based on the cognitive enhancing system's cognitive diagnostic outputs, decisions can be made to adjust the dose or frequency of a therapy, including termination of a therapy.

Populations that can benefit from the present methods further encompass those that suffer from attention deficit disorder (e.g. attention deficit hyperactivity disorder (ADHD)). Cognitive losses of developmentally impaired child and adult populations, encompassing general or undiagnosed developmental delays and Autism Spectrum Disorder (ASD), can also be potentially reversed by the subject method.

For individuals suffering from chronic neurological and psychiatric illness, changes in inhibitory neuron populations, myelination, response slowing, emergent response dis-coordination, degradation of response selectivity in spatial, spectral and temporal detail, and the degradation of the distinctions between background and target stimuli are very similar to the effects of age-related cognitive decline. Accordingly, individuals of any age with profiles of cognitive impairment that parallel those in aging are target populations for the methods and tools of the present disclosure. The individuals can experience substantial 'corrective' neurological changes if trained by the subject methods.

Additionally, many individuals, though not experiencing a perceptible decline in cognitive function, may desire to increase their current cognitive abilities. One example is to improve the performance of everyday tasks (e.g. multitasking, focus, memory, social skills, such as conversational skills, decision-making abilities, creativity, or reaction times to specific task). Another example is to improve general metrics of cognitive ability (e.g. to "enhance IQ"). Since people are susceptible to interference or are exposed to interference in daily life, the present methods also have a utility for training cognitive abilities in those who are not necessarily experiencing a cognitive decline or impairment. Secondary effects dependent on the above mentioned and trained cognitive abilities may also be a target for training using the present disclosure. Therefore, populations whose activities involve multitasking could increase performance in carrying out their professional duties or hobbies by interference training as described herein. Examples of such populations include, but are not limited to, athletes, airline pilots, military personnel, doctors, call center attendees, teachers and drivers of vehicles.

Other examples include learning, such as learning in a specific subject area (e.g. math or reading), a general ability to learn in the presence of interference, enhancing social interaction, etc. The present disclosure can also be applied to a more direct training on educational materials independent of interference training. For example, the methods described herein can be incorporated in a personalized, efficient and motivational intelligent tutoring system for training in a specific educational domain such as math or science. Therefore, regardless of performance level, pre-school and school-aged children, and teenagers and young adults, i.e. all individuals over the age of 5 years, would be populations that benefit from the present disclosure.

In addition to the immediate applications in cognitive training, the system and mechanics described herein are directly suited for personalized training in other domains such emotion processing and social intelligence. Developmental programs in early education designed to equip pre-school and school age children with tools necessary to perceive, process and respond to emotional stimuli in a personally effective and socially appropriate manner can benefit from the present disclosure. Teenagers and young adults can utilize such training to maximize their social skills in order to build meaningful relationships, minimize social isolation, and handle miscommunication and conflicts of interest in an efficient and positive manner. Corporate training programs designed to teach collaboration, communication, conflict resolution and negotiation skills can benefit from the present disclosure for customizing their training programs to individual employees' skills and abilities. In addition to the above groups, individuals at an increased risk of social and emotional impairment and populations that suffer from deficits in processing in these domains (for example socially marginalized individuals and convicted felons), or any individual who desires to improve his/her social and emotional intelligence can benefit from the present disclosure.

Other applications of the present disclosure include physical training and motor rehabilitation programs such as interactive platforms for physiotherapy, exercise or athletic training. These programs can be tailored to the current performance and desired skill level of the individual performing the training regimen by utilizing the methods described herein. Populations that can benefit from a personalized, adaptive physical training regimen encompass people of all ages and physical abilities, athletes, healthy individuals as well as patients recovering from musculoskeletal pain and impairment due to injury, stroke, osteoarthritis or other causes.

Demonstration of Efficacy

With the goal to diagnose or enhance cognition and related effects in individuals, it can be desirable to experimentally determine the efficacy of a training session or program. Suitable methods of experimental testing include those types of studies known in the art to test the efficacy of cognitive, behavioral, or pharmacological intervention, including pilot human studies and clinical trials. These types of experimental tests can be conducted with any group of individuals, and preferably with a group of individuals that represents the target population of the eventual training session or market products. Preferably, the studies are conducted in such a way as to give strong statistical powering to the conclusions, including methods known in the art such as placebo/sham/vehicle comparator groups, blinding of subjects and experimenters, randomization of subjects into the various groups, and the like.

As mentioned in sections above, one efficacy-testing method suitable for the present disclosure is the administration of pre-training and post-training assessments which allow for the determination of whether training has led to a measurable change in the function of which the assessment is composed. In one embodiment, the pre-training and post-training assessment is comprised of general cognitive functions, which pertain to both healthy individuals and individuals that have experienced or are at risk of experiencing cognitive deficits, including clinical patient populations. Such suitable tests include those known in the art to test any specific functions of a range of cognitions in cognitive or behavioral studies, including tests for perceptive abilities, reaction and other motor functions, visual acuity, long-term memory, working memory, short-term memory, logic, decision-making, and the like.

In another embodiment, the pre-training and post-training assessment is comprised of tests that measure improvement on actual functional activities of daily living. Examples can include tests that are specifically constructed or validated to measure such outcomes, such as Activities of Daily living that are used in clinical trials of elderly populations, or similar simple measurements such as the ability to perform a directed task, reading or conversational comprehension, efficiency in a workplace environment, and the like.

In another embodiment, the pre-training and post-training assessment is comprised of tests (e.g., cognitive ability tests) that measure improvement on symptoms or functions relevant to a specific disease or condition. Suitable types of tests include those that objectively measure symptom severity or biomarkers of a disease or condition, tests that use subjective clinician or observer measurement of symptom severity, and tests that measure cognitive functions known to be correlated with disease states. Examples of such tests include but are not limited to assessment scales or surveys such as the Mini Mental State Exam, Test of Variables of Attention, CANTAB cognitive battery, Repeatable Battery for the Assessment of Neuropsychological Status, Clinical Global Impression scales relevant to specific conditions, Clinician's interview-Based Impression of Change, Severe Impairment Battery, Alzheimer's Disease Assessment Scale, Positive and Negative Syndrome Scale, Schizophrenia Cognition Rating Scale, Conners Adult ADHD Rating Scales, Hamilton Rating Scale for Depression, Hamilton Anxiety Scale, Montgomery-Asberg Depressing Rating scale, Young Mania Rating Scale, Children's Depression Rating Scale, Penn State Worry Questionnaire, Hospital Anxiety and Depression Scale, Aberrant Behavior Checklist, Activities of Daily Living scales, General Practitioner Assessment of Cognition, Eriksen Flanker Task, Stroop Task, Intelligence quotient, Raven's Progressive Matrices, Behavior Rating Inventory of Executive Function (BRIEF), Test of Everyday Attention (and Test of Everyday Attention for Children), Test of Memory and Learning, Wisconsin Card Scoring Test, and Delis Kaplan Executive Function System; physiological tests that measure internal markers of disease or health such as detection of amyloid beta, cortisol and other stress response markers; and brain imaging studies (for example fMRI, PET, etc.) that assess a condition based on presence of specific neural signatures. In certain embodiments, part of a particular test (e.g., a sub-section or a particular index score) may be implemented. Table 1 and Table 2 include information related to certain example tests.

TABLE 1

| Test | Cognition Evaluated | Clinical Indication | Scoring System |
| --- | --- | --- | --- |
| Mini Mental State Exam | Registration, attention and calculation, recall, language, ability to follow simple commands, and orientation | Screening for dementia and Alzheimer's disease | The maximum MMSE score is 30 points. A score of 20 to 24 suggests mild dementia, 13 to 20 suggests moderate dementia, and less than 12 indicates severe dementia. |
| CANTAB cognitive battery | Memory, executive function, attention, decision making, social cognition, induction | CANTAB batteries are composed of many smaller exams which can be combined for specific disease areas such as ADHD, Schizophrenia, depression, and dementia | Each portion of the CANTAB battery has its own score, and the different portions are combined in many different ways, so there is no overall scoring system for the CANTAB battery. |

TABLE 1-continued

| Test | Cognition Evaluated | Clinical Indication | Scoring System |
|---|---|---|---|
| Test of Variables of Attention | Attention | Diagnosis or medication response for ADHD | Assess a few different domains and creates a composite score for ADHD. In the current version of the test any score below 0 on the composite is consistent with attention deficits. |
| Repeatable Battery for the Assessment of Neuropsychological Status | Immediate memory, visuospatial/ constructional, language, attention, delayed memory | Screening for dementia and other methods of cognitive deterioration, track recover, track disorders | The RBANS is composed of 12 subtests that yield 5 index scores and a total score. Index scores are given based on the mean and standard deviation of age group matched neurotypical participants. |
| Clinical Global Impression scales | Global function | Assessing function prior to and after starting a medication | There are two scores on this scale, one for severity and one for improvement. Each is a scale from 1 to 7. On the severity scale, 1 is not ill and 7 is extremely ill. On the improvement scale 1 is very much improvement and 7 is very much worse condition since treatment initiation. |
| Clinician's interview-Based Impression of Change | Global function | Assessment for dementia and Alzheimer's disease | This rating scale is based on the health care provider's "general clinical impressions" with or without the informant input (i.e. family members). It evaluates global function and is scored from 1 (very much improved) to 7 (very much worsened). |
| Severe Impairment Battery | Attention, orientation, language, memory, visuospatial ability, and construction | Cognitive abilities at the lower end of the range. | Range of possible scores is from 0-100. A score of less than 63 is considered 'very severely impaired.' |
| Alzheimer's Disease Assessment Scale | Cognition: Memory, language, praxis, attention, and cognitive abilities; Non-cognitive functions: mood and behavior | Track Alzheimer's Disease and evaluate the stage disease | The scores of 11 tasks are added for a total ADAS-Cog score. A score for of someone without Alzheimer's disease or dementia is 5. |
| Positive and Negative Syndrome Scale | Presence of positive symptoms (hallucinations) and negative symptoms (loss of normal function) for schizophrenia | Symptom severity for patients with schizophrenia | The positive and negative scales each have 7 items with a score ranging from 7-49. The general psychopathy scale has 16 items with a score from 16-112. Mean scores for patients with schizophrenia are positive: 18.20, negative: 21.01, general psychopathology: 37.74. |
| Schizophrenia Cognition Rating Scale | Functional capacity | Schizophrenia | An 18 item interview based assessment with each item rating on a four point scale. |
| Conner's Adult ADHD Rating Scales | Attention | Diagnosis and monitoring of ADHD in adults | This test relies on self-reported and observer reports of patient behaviors. The test contains a total score and subscale scores of Inattention/Memory problems, Hyperactivity/Restlessness, Impulsivity/Emotional Liability, Problems with Self-Concept. |
| Hamilton Rating Scale for Depression | Mood | Monitoring of therapy for depression | A score of 0-7 is considered to be normal. Scores of 20 or higher indicate moderate, severe, or very severe depression, and are usually required for entry into a clinical trial. |
| Hamilton Anxiety Scale | Anxiety | Monitoring of anxiety | The scale consists of 14 items designed to assess the severity of a patient's anxiety. Each of the 14 items contains a number of symptoms, and each group of symptoms is rated on a scale of zero to four, with four being the most severe. All of these scores are used to compute an overarching score that indicates a person's anxiety severity. |
| Montgomery-Asberg Depression Rating scale | Mood | Measure severity of depressive episodes in patients with mood disorders | Higher MADRS score indicates more severe depression, and each of the 10 items yields a score of 0 to 6. The overall score ranges from 0 to 60. Under 6 is considered normal, 7-19 is mild depression, 20-34 is moderate depression, and greater than 34 is severe depression |

TABLE 1-continued

| Test | Cognition Evaluated | Clinical Indication | Scoring System |
| --- | --- | --- | --- |
| Young Mania Rating Scale | Mania | Measure severity of manic episodes in patients with mood disorders, particularly bipolar disorder | There are four items that are graded on a 0 to 8 scale (irritability, speech, thought content, and disruptive/aggressive behavior), while the remaining seven items are graded on a 0 to 4 scale. These four items are given twice the weight of the others to compensate for poor cooperation from severely ill patients. There are well described anchor points for each grade of severity |
| Children's Depression Rating Scale | Mood | Diagnosis and monitoring of depression in children | This scale is a 16-item measure used to determine the severity of depression in children 6-12 years of age. Items are measured on 3-, 4-, 5-, and 6-point scales. The CDRS is derived from the Hamilton Rating Scale for Depression (HAM-D); a score of 15 on the CDRS is equivalent to a score of 0 on the HAM-D. Assessment information is based on parent, child and schoolteacher interviews. |
| Penn State Worry Questionnaire | Anxiety | Monitoring anxiety symptoms. | The questionnaire consists of 16 questions, each with a 5 possible responses. The total score ranges from 16-80. A score of 40-59 is considered moderate worry and a score above 60 is considered high worry |
| Hospital Anxiety and Depression Scale | Anxiety, mood | Detection of anxiety and depression in people with physical health problems | 14 item scale with 7 items related to mood and 7 to anxiety. |
| Aberrant Behavior Checklist | Irritability, agitation, crying, lethargy, social withdrawal, stereotypic behavior, hyperactivity, noncompliance, and inappropriate speech. | Monitoring treatment effects on severely retarded individuals | This checklist contains a 58 item scale with each item having a score from 0-3. The scores are added from each item into their respective subscale. |
| Activities of Daily living Checklist | Functionality | Monitoring condition of and planning assistance for elderly patients. | The checklist contains a list of daily living activities (Ex. Bathing, cooking, climbing stairs). The list allows notation for if a person can perform a task independently, needs help, is dependent on others, is not able to perform each activity. |

TABLE 2

| Test | Cognition Evaluated | Clinical Indication | Scoring System |
| --- | --- | --- | --- |
| General Practitioner Assessment of Cognition | Overall function | Screening for dementia and cognitive decline | There are 9 tasks in the test, each given one point for a correct completion. A score of 4 points or less indicates a person is likely to have a cognitive impairment. A cognitive interview is completed if a patients a a score from 5-8. |
| Eriksen Flanker Task | Response inhibition | Screen for ADHD and other attention conditions | Tracks ability to provide a response in the presence of congruent stimulus, incongruent stimulus, and neutral stimulus. Success measured by accuracy, reaction time, and comparison of reaction time under different stimuli. |
| Stroop Task | Response inhibition, Set shifting | Screen for ADHD and other attention conditions | Tracks ability to react to a specific stimuli (color or location) with incongruent stimulus (word describing different color) and congruent stimulus. Success measured by accuracy, reaction time, and comparison of reaction time under different stimuli. |
| Intelligence quotient | IQ | Triaging intellectual disability, educational placement | 100 is the median score and each standard deviation is 15 points (lower score indicates lower cognitive function) |

TABLE 2-continued

| Test | Cognition Evaluated | Clinical Indication | Scoring System |
|---|---|---|---|
| Raven's Progressive Matrices | Reasoning ability | Educational placement and assessment; assessment for Asperger syndrome | This test contains questions which get progressively harder. The higher a person scores the better their reasoning ability is. |
| Behavior Rating Inventory of Executive Function (BRIEF) | Inhibitory Self-Control, Flexibility, Emergent Metacognition | Assessment of ADHD and other executive function disorders | Test creates a behavior regulation index and sub-scores for the three cognitive areas tested. Answers are scored relative to a normative population based on age. |
| Test of Everyday Attention (and Test of Everyday Attention for Children) | Selective attention, sustained attention, and mental shifting | Assessment of ADHD, dementia, Alzheimer's disease and other attention disorders | This test has different subsets with are all scored. |
| Test of Memory and Learning | Verbal memory, nonverbal memory, composite memory index | Assessment of memory in dementia and Alzheimer's disease | Scores are based on the number of correct answers and how that relates to normative data. |
| Wisconsin Card Scoring Test | Concept generation, set shifting, strategic planning | Assessment of ADHD, Autism, neurodegenerative disease, acute brain injury, schizophrenia, and other cognitive disorders | This test is scored on the number of categories achieved, trials, errors, and perseverative errors. |
| Delis Kaplan Executive Function System | Verbal and non-verbal executive function | Used to assess frontal lobe disorders, ADHD, learning disabilities, mood disorders, autism, traumatic brain injury, and spina bifida | This test is composed of 9 individual tasks, each of which are scored seperately |

In another embodiment, the pre-training and post-training assessment is comprised of survey or questionnaire-styles test that measure a subject's self-reported perception of themselves. These can include self-report scales of healthy function or feelings, or disease function or symptoms. Examples of suitable self-report tests include but are not limited to ADHD self-report scale, Positive and Negative Affect Schedule, Depression Anxiety Stress Scales, Quick Inventory of Depressive Symptomatology, PTSD Checklist, and any other types of surveys that can be conducted for a subject to report on their general feelings of symptoms of a condition or satisfaction with real-world functional status or improvement.

EXAMPLES

It is understood that the examples and embodiments described herein are for illustrative purposes only and that various modifications or changes in light thereof will be suggested by persons skilled in the art and are to be included within the spirit and purview of this application and scope of the appended claims. All publications, patents, and patent applications cited herein are hereby incorporated by reference in their entirety for all purposes.

Example 1-Project: EVO-Computational Cognitive Training System

We have designed and built an adaptive cognitive training system as the underlying software mechanics in a clinical prototype cognitive intervention entitled "Project: EVO," which is operated by an individual on a mobile tablet or smart phone. The adaptive cognitive training system that powers Project: EVO uses the methods of the present disclosure to present to an individual a personalized cognitive training experience.

Background of Project: EVO

Project: EVO is built as a mobile video game as a way to improve the executive function of an individual by adaptively increasing the load and complexity of two tasks done concurrently by the individual (multitasking), in an engaging computer environment. To date, the game has been deployed in multiple clinical studies that use standard intervention protocols and standard pre-training and post-training assessments to determine any effect that the product has on cognition, behavioral, and symptomatic measurements. Example screenshots from the functional clinical version of Project: EVO are shown in FIG. 5A-FIG. 5F.

Project: EVO presents two types of tasks to an individual; a perceptual reaction task (called "Tapping" in the game) and a visuomotor tracking task (called "Navigation" in the game). The perceptual reaction task may need an individual to respond by tapping on the screen of the mobile tablet/phone when a visual target of interest appears (for example, a green circular fish) but to inhibit their response and not tap the screen when a target that is not the target of interest appears (for example, a green square-shaped fish, or a red circular fish). The visuomotor task may need an individual to "steer" a visual figure/avatar down a river by subtly tilting the screen of the mobile tablet/phone so as to keep the avatar in the middle of the river. The individual may avoid obstacles that are generated in the avatar's path in order to succeed. The two tasks are based on the basic framework of the multitasking paradigms used to cognitively train individuals in previous publications and patent art (Anguera J A et al., 2013 Nature, 501: 97-101; Int. Pat. No. WO2012/

064999A1 by Gazzaley A). Thus, the personalized cognitive training system has the ability to deploy previously reported cognitive tasks in a personalized format to provide an individual with a tailored cognitive training experience not hindered by the issues with standard deployment of such tasks, as discussed in the Background of the present disclosure.

Difficulty Levels in Project: EVO

The difficulty level of the reaction task is modified based on user performance. The difficulty level is made to increase as an individual properly performs the tapping task in the proper amount of time. The difficulty level is made to decrease as an individual fails to perform the tapping task-either by responding to a non-target or not responding in the proper amount of time to a target of interest. Similarly, the difficulty level of the navigation task is made to increase as an individual properly performs the navigation task by avoiding obstacles in the avatar's path. The difficulty level is made to decrease as an individual fails to properly perform the navigation task-either by crashing into obstacles in the user's path or the walls of the course. The difficulty levels that an individual can attain are represented to the user as a variety of rewards within the game environment (FIG. 6). For example, after an assessment the difficulty level that the individual obtained is presented as the attainment of a certain level of "super-coin" in a post-assessment wrap-up screen (FIG. 6A). As another example, during and after a training run, the difficulty level at which an individual may perform is represented by stars that the individual can attain by performing at a certain level (FIG. 6B). More is discussed in the sections below.

Adaptivity of Tasks

Project: EVO adapts the difficulty level of the cognitive tasks in real-time, in order to properly keep a user challenged as he/she performs the cognitive tasks. Therefore, the individual's performance on the last event of gameplay determines the exact difficulty of the next event, and the aggregate performance over an extended period of time generally determines the average difficulty level that an individual may be experiencing at any one time. FIG. 1C shows data from a specific subject during a training regimen, and highlights the upward and downward adaptation of difficulty in real-time throughout the training run.

During dual-task assessment and during Training modules (described below), each task adapts using the above-described methods independently as the two tasks are being simultaneously performed. Project: EVO adapts the complexity of the task (i.e., presents an entirely new variant, including a new rule-set, of the cognitive tasks to an individual) after the individual is determined by the system to have mastered the current task version. In the current version of Project: EVO, after the system deems the user to have mastered the task after measuring progress through multiple re-assessment cycles, the system then "unlocks" the next task challenge (greater complexity), which in Project: EVO is represented as a new world (see FIG. 6C).

Assessments and Training in Project: EVO

Project: EVO employs a personalized assessment, re-assessment, and training system. When an individual begins a training regimen in Project: EVO, the system triggers an initial "Baseline Assessment" where his performance on single task Tapping, single task Navigation, and dual-task (Tapping and Navigation each measured while conducting both tasks at the same time) are each measured in consecutive phases. Performance levels on Project: EVO assessments are calculated by the methods described above in the present disclosure.

The Baseline Assessment also establishes the individual's first Performance Range. In Project: EVO, the increase in ability during multitasking is the intended goal of the training regimen, and within each assessment/training phase the goal is to increase the individual's executive abilities to the point where he can multitask nearly as well as he is able to perform the individual tasks in isolation. The individual's dynamic performance range, which will be used to set his goals in the training module, uses certain values obtained during single-tasking and during multitasking and is defined as the range between and inclusive of these performance values.

After finishing a Challenge, an individual is shown his performance scores and then progresses to the "Training" module. The Training module of Project: EVO entails performing an adaptive dual-task for multiple consecutive runs. The goal of Training is to improve abilities on the tasks (Tapping and Navigation) when done simultaneously. Improvement goals are set by the system and displayed to the user as 5 "stars" that he/she needs to obtain, each star set at a higher difficulty level of dual-task performance. The difficulty levels that each star represents correspond to certain progress gates obtained during the recent assessments. On obtaining a star, the individual is able to sample a higher range of performance difficulty levels on both tasks, and so on for each remaining star.

FIGS. 8A-8D show de-identified data from a recent study participant's data as he progressed through assessments, re-assessments, and training in a single world of EVO gameplay. FIG. 8A shows the participant's baseline assessment data. The average difficulty level of the single task and dual-task phases are shown visually by horizontal lines that cross they-axis, those levels being used to set the progress gates for the Training module. FIG. 8B shows data from the first training run performed by the individual. FIG. 8C shows the same individual's progress over multiple training runs. The individual took 10 training runs to get the first 5 stars, 15 training runs to attain the next 5 stars, and 25 training runs to attain the final 5 stars, thus demonstrating the importance of re-assessment in continually challenging the player.

Other Rewards in Assessment and Training

In addition to the awards discussed above (e.g., super-coins and stars), Project: EVO contains a variety of rewards that are meant to incentivize and motivate individuals to play at their maximal ability, both moment-to-moment and over extended periods of time. Every tapping event includes visual and auditory feedback to signal to the user if he is responding appropriately to the visual stimuli. Additionally, navigation events also have visual and auditory stimuli to help the user stay on track. Points are allotted for successfully executed events, for attaining stars during training, and for completing a number of daily plays. These points are displayed on the user's home base map screen, and can be "spent" to purchase avatars and costumes that show themselves in subsequent user game play. State of the art visual graphics and current audio sound tracks enhance the overall user experience.

Example 2-Validation of Efficient Cognitive Training

Multiple pilot studies have been conducted with versions of Project: EVO at various phases of product development. The data and feedback from early studies allows for product iteration to directly address mechanical or engagement issues experienced in various subject populations. These testing cycles afforded us the opportunity to directly compare an early version of the Project: EVO system that had the core cognitive tasks in an adaptive format but did NOT have the personalized difficulty and re-assessment system in place, with the current version of Project: EVO that had the full personalized system configured.

We conducted an at-home cognitive training study with 8-12 year old children from a variety of clinical categories: neurotypical, autistic, and attentional/sensory issues. The study was conducted at an academic medical research center trained in cognitive studies of healthy and diagnosed pediatric populations. The children each received a ~30-minute introduction to Project: EVO at the direction of a clinical coordinator, and were sent home with mobile devices that housed the game, with directions to engage in the game 5 days per week for ~30 minutes per day, for 1 week. Project: EVO mechanics are self-adaptive, meaning that no clinician interaction was necessary with the device and the children could play on their own at home. Each study subject's cognitive and play data in the game were wirelessly uploaded to a secure database, allowing for high-resolution parsing of individual progress.

After the study completed, individual progress curves were analyzed to determine the dynamics by which study participants progressed through the protocol, their compliance, and any interesting behavioral patterns that emerged. The progression data of an exemplary individual from this study (in this case, a neurotypical child), is shown in FIG. 7A. The data shows that the subject was able to complete the training goals in 9 runs, progressing through the first world of the game and moving on to another world. Cognitive measurements made in the game were also taken before and after the training. As shown in FIG. 7B, the subject improved his cognitive performance on the Navigation task from level 11.9 to level 15.7, and improved interference processing costs from −23.7% to −9.3% on Tapping, and −0.8% to −0.6% on Navigation over the course of training in world one. On average, subjects in this study took ~s runs to complete the world, improving their multitasking performances by 0.43±1.50 (mean±std. dev.) levels i.e. by an average reaction time of 2.6 s on the Tapping task, and 1.03±1.55 levels on the Navigation task.

After configuration of the personalized training system, with progress gate setting and re-diagnoses intact, we re-ran the above study to determine the feasibility of the new cognitive training version, and to examine the effects of our new system at enhancing challenging training time for subjects. This follow-up study was conducted at the same academic medical research center, with the same clinical coordinators, and the same inclusion criteria to get similar patients and healthy participants in the same age-range, thus providing for a direct comparison and reducing the chance that effects seen are due to variance between study site geography, study staff, or subject profile. All subjects were run through the same protocol, which entailed an in clinic visit followed by a 1-week at-home training module. Data was collected as previously described.

The progression data of an exemplary individual from this follow-up study (in this case, a neurotypical child) is shown in FIG. 8C. The data shows that the subject was able to complete the training goals in 50 runs, progressing through the first world of the game and moving on to another world. In comparison with the subject from the earlier study (FIG. 7C), the training progression curve of this subject from the new study shows that the individual spends far more time training to get through the world. The curves are more drawn out. Additionally, looking at each 5-star increment (where re-assessments are made in the new system), it is clear that a single assessment would have provided a minimal training baseline, as the individual reached his ceiling in 10 runs. After each re-diagnosis (5 stars and 10 stars), the subject's training becomes harder and more drawn out, signaling that the system continues to challenge the user and tap into an incremental cognitive opportunity as the subject approaches his improvement ceiling.

The effects of the more drawn-out training module can be seen in the cognitive outcome measurements made before and after training (FIG. 8D). This subject in the newly configured personalized version improved his cognitive performance from level 11.2 to 12.5 on Tapping, and level 10.7 to 15.4 on Navigation and improved interference processing costs~3 fold on Tapping over the course of training Navigation commonly shows inverse costs in this population (multitask is better than isolated task) for a variety of putative reasons, and thus we prospectively do not include Navigation cost as a reliable measure of cognitive function in these studies. Notably, this graph allows us to view the benefits that the re-assessment had, as the second phase of training (after the first 5 stars were attained) expanded on the improvements of the first training progress gate, seeing the individual further improve his interference costs from −15.4% to −11.4% on Tapping.

On the whole, subjects in the new version of the game averaged 31 runs to complete the world, improving their multitasking performance by 2.10±1.85 (mean±std. dev.) levels i.e. by an average reaction time of 12.6 s on the Tapping task. This compares quite favorably to the first study using the simplified early version without the personalization system.

Example 3-Validation of Effective Cognitive Training

As one step towards validating that the cognitive training system can have pro-cognitive benefits, a pilot clinical study was conducted in which pediatric ADH patients were recruited to perform a 4 week at-home cognitive training protocol, with a clinical visit before and after the 4 weeks that measured the individual not only on Project: EVO play but also gold-standard clinical measures of cognitive/executive function on which the subject did not receive training. These tests represent accepted measures to know if the training progress in the cognitive training environment "transferred" or "generalized" to broader measures of cognition and were not solely specific to measurements in the training software.

FIG. 11 is a results summary from the study participants, showing that cognitive improvements were made not only on EVO measurements but also excitingly on gold-standard tests of attention, impulsivity, and working memory. The ADHD group saw robust improvements on EVO measurements (FIGS. 11A-C) as well as on clinical standards (FIG. 11D), suggesting that training on Project: EVO resulted in significant cognitive benefits that were transferrable to the real world. The control group also demonstrated improvements on clinical scales, with the greatest benefits observed on the memory measures (data not shown). This demonstrates that the cognitive training system built in accordance with the system and methods of the present disclosure can efficiently and effectively train both diseased and neurotypical populations, and personalization is to properly place an individual at his baseline and adapt the system to him in order to tap into robust cognitive benefits.

The present disclosure features systems and methods for the implementation of efficient cognitive training. For example, the present disclosure has leveraged the insight that the lack of efficiency in cognitive training is an issue with personalization of difficulty and reward levels, to design a unique set of algorithms and an integrated, interactive computational system that sets the difficulty and rewards based on the individual's own abilities. While addressing efficiency problems has appeared unfeasible previously, this insight has enabled a holistic approach towards the construction of a seamless computational platform for personalization of difficulty and reward progression that allows for efficient training for individuals of a wide range of ability levels, in a format suitable for an engaging user experience.

Various embodiments of methods and systems are disclosed herein for setting a personalized adaptive difficulty progression of a cognitive training protocol of an individual, in which the training difficulty levels, progression and rewards are set and modulated based on an assessment of the individual's own current and maximal cognitive abilities. According to some embodiments, a method includes assessment of an individual's performance on a cognitive task followed by presenting to the individual a subsequent training regimen on such cognitive task, the difficulty and difficulty progression of which are determined by that prior assessment. Hence, the method provides a specific way to utilize information specific to the individual's performance range in order to adapt and increase difficulty, as opposed to a standard, pre-defined, non-individualized difficulty schedule. In certain embodiments, the process of assessment followed by training can be delivered as a cycle, where new assessment and training phases can be presented to the individual if the individual's performance during training reaches his/her personalized difficulty goal as defined by the system.

In certain embodiments, the difficulty levels of a cognitive task are distributed across the individual's performance range, between the individual's current ability to the individual's maximal ability. For example, a single assessment phase prior to a training phase is used to determine both the individual's current and target maximal ability. In one embodiment, the cognitive task is a dual- or multi-task, and the individual's range is defined as between his/her performance on the multi-task and his/her performance on the single-tasks.

In certain embodiments, the difficulty levels are tied to and represented by progress gates that the individual may perform at in order to progress through and complete the cognitive training protocol. As an example, progress gates are tied to rewards that the individual experiences as he/she matches those difficulty levels, and rewards can be a variety of modalities. In an embodiment, the rewards tied to difficulty levels include visual and auditory feedback suitable to an interactive environment. In some embodiments, the rewards are dynamically shifted to other difficulty levels than the original level to which they were tied, in order to ensure an individual's progress when the individual cannot go past certain difficulty levels.

In certain embodiments, personalized lower bounds are placed on the difficulty levels that an individual may sample during training, in order to ensure that an uncharacteristically poor performance does not lead to the training becoming too easy and that training is continually challenging and efficient. In an embodiment, the lower bound is set at an increment relative to the individual's current performance level as calculated in the most recent assessment phase.

In certain embodiments, personalized upper bounds are placed on the difficulty levels that an individual may sample during training, in order to ensure that uncharacteristically high performance does not significantly increase training pace and subsequent training is not too difficult. In one embodiment, the upper bound is set at an increment relative to the individual's target or maximal performance level as calculated in the most recent assessment phase.

In some embodiments, each of the above methods of setting the difficulty and rewards of an adaptive cognitive training regimen constitute system components that can each independently be implemented to personalize and improve training efficiency. Alternately, as described in other embodiments, the methods described herein can be combined into a single, integrated platform for personalized and efficient cognitive training.

This written description uses examples to disclose the invention, including the best mode, and also to enable a person skilled in the art to make and use the invention. The patentable scope of the invention may include other examples. As an example, the processor-implemented systems and methods disclosed herein can be configured to provide proper personalization and adjustment of difficulty based on a user's true capabilities for the user to work on a task at a difficulty level that is within the user's ability but challenging in order for the cognitive training to have benefits for the user. Specifically, the processor-implemented system and method can be configured to set difficulty levels and attainment goals for a specific individual performing a regimen (neither arbitrarily nor based upon the average ability of a group), which leads to personalized pacing through the training regimen and helps to reduce plateauing effects when a user can no longer progress. As an example, the processor-implemented system and method disclosed herein can be beneficial to disease populations, where variation of ability level can be high and certain subsets of the patient population who are significantly below the mean difficulty level may be unable to partake in effective cognitive training within conventional cognitive training schemes.

As another example, the processor-implemented system and method disclosed herein can be configured to provide algorithms to define a precise target for maximal ability of a specific individual and set proper increases in difficulty level over time to ensure the individual is trained across his/her full cognitive range. For example, the processor-implemented system and method disclosed herein can remedy issues related to traditional cognitive training systems which adapt task difficulty after blocks (sets of multiple stimuli, each requiring a response from the individual) and lead to the potential for significant periods of time in which an individual is at a training level far too easy (after performing uncharacteristically poor for one of a variety of reasons, such as having been distracted by an external event) or far too difficult (after performing uncharacteristically well, for instance during a heightened state of arousal) during one block. Moreover, the processor-implemented system and method disclosed herein can remedy issues related to conventional real-time thresholding approaches (such as single-event staircase and maximum likelihood procedures taught by U.S. Pub. No. 20070299319A1, Chan S C and Hardy J L).

For example, the processor-implemented system and method disclosed herein can be configured to deploy effective cognitive training through differentiating an individual's actual improvement in cognition from "practice effects" (getting better at a task due to familiarity), so as to keep training regimens for the individual challenging and provide sufficient opportunities to train the individual in his/her full dynamic range. As an example, the processor-implemented system and method disclosed herein can be configured to provide personalized difficulty tuning, precise target setting, and accurate measurements of performance improvement so as to improve user experience and motivate users to engage in cognitive training tasks with dedicated effort. Specifically, the processor-implemented system and method disclosed herein can be configured to provide a better rewards structure tied to proper personalized difficulty so that the rewards are not too easy or too difficult to achieve, compared with certain conventional approaches (such as those taught by U.S. Pat. No. 6,585,518B1, Jenkins W M et al.).

As an example, the processor-implemented system and method disclosed herein can be configured to seamlessly incorporate various elements needed for efficient training into a platform to provide a suitable interactive environment for motivated engagement and to provide truly effective and personalized cognitive training. Specifically, the processor-implemented system and method disclosed herein can be configured to provide a unique computational system and associated set of algorithms set in an interactive framework that allow for an efficient and personalized training experience by customizing the difficulty and reward cycles based on assessment of an individual's recent baseline performance levels.

For example, the processor-implemented system and method disclosed herein can be configured to afford a general scheme for personalization and improvement of the efficiency of an adaptive training regimen. Therefore, the systems and methods described herein are not restrictive to cognitive training, and can be effectively applied towards personalized and efficient learning in other domains including, but not limited to, training of emotion processing and social intelligence, physical training and motor rehabilitation, and mastery of educational materials. The systems and methods described herein can also be applied to interactive gaming environments, such as computer and video games, where the game difficulty and advancement are personalized to an individual's capabilities and skill level.

Further embodiments are explained with the help of the following examples:

EXAMPLES

1. A method of operating a data processing system including one or more data processors and a non-transitory machine readable storage medium, the method comprising: performing, using the one or more data processors, a cognitive assessment of a user using a set of assessment tasks; estimating, using the one or more data processors, a maximal performance of the user related to the set of assessment tasks; determining, using the one or more data processors, a performance range based at least in part on the maximal performance of the user; dividing, using the one or more data processors, the performance range into a plurality of progress gates, the plurality of progress gates corresponding to a plurality of task difficulty levels, data related to the performance range being stored in a data structure in the non-transitory machine-readable storage medium; selecting, using the one or more data processors, a first progress gate within the performance range; generating, using the one or more data processors, a first set of training tasks associated with the first progress gate; collecting the user's first training responses to the first set of training tasks; determining, using the one or more data processors, whether the user succeeds at the first progress gate based at least in part on the user's first training responses. The method further includes: in response to the user succeeding at the first progress gate, selecting, using the one or more data processors, a second progress gate within the performance range; generating, using the one or more data processors, a second set of training tasks associated with the second progress gate; and collecting the user's second training responses to the second set of training tasks for determining whether the user succeeds at the second progress gate.

2. The method according to example 1, further comprising: determining a plurality of rewards; and associating the plurality of rewards with the plurality of progress gates.

3. The method according to example 1 or example 2, further comprising: in response to the user succeeding at the first progress gate, presenting a first reward associated with the first progress gate to the user.

4. The method according to one of the preceding examples, further comprising: determining whether the user succeeds at the second progress gate based at least in part on the user's second training responses; and in response to the user succeeding at the second progress gate, presenting a second reward associated with the second progress gate to the user.

5. The method according to one of the preceding examples, wherein the plurality of rewards include one or more of the following: visual rewards, auditory rewards, tactile rewards, olfactory rewards, and taste rewards.

6. The method according to one of the preceding examples, wherein the plurality of rewards are dynamically determined and modified.

7. The method according to one of the preceding examples, further comprising: in response to the user performing a predetermined number of training tasks associated with the first progress gate, presenting a first reward associated with the first progress gate to the user.

8. The method according to one of the preceding examples, further comprising: in response to the user performing the first set of training tasks for a predetermined duration, presenting a first reward associated with the first progress gate to the user.

9. The method according to one of the preceding examples, further comprising: in response to the user advancing from the first progress gate to the second progress gate within a predetermined time period, presenting a first reward associated with the first progress gate to the user.

10. The method according to one of the preceding examples, further comprising: in response to the user performing tasks associated with the plurality of progress gates for a predetermined duration, presenting the plurality of rewards to the user.

11. The method according to one of the preceding examples, wherein the plurality of rewards include indications associated with the plurality of progress gates.

12. The method according to one of the preceding examples, wherein: the first progress gate corresponds to a first task difficulty level; the second progress gate corresponds to a second task difficulty level; and the second task difficulty level is higher than the first task difficulty level.

13. The method according to one of the preceding examples, further comprising: in response to the user not succeeding at the first progress gate for a predetermined duration, determining a third task difficulty level to be associated with the second progress gate, the third task difficulty level being lower than the second task difficulty level; generating a third set of training tasks according to the third task difficulty level; and collecting the user's third training responses to the third set of training tasks for determining whether the user succeeds at the second progress gate.

14. The method according to one of the preceding examples, further comprising: in response to the user not succeeding at the first progress gate, generating a third set of training tasks associated with the first progress gate; and collecting the user's third training responses to the third set of training tasks for further determining whether the user succeeds at the first progress gate.

15. The method according to one of the preceding examples, further comprising: determining whether the user succeeds at the second progress gate based at least in part on the user's second training responses; in response to the user succeeding at the second progress gate, selecting, using the one or more data processors, a third progress gate within the performance range; generating, using the one or more data processors, a third set of training tasks associated with the third progress gate; and collecting the user's third training responses to the third set of training tasks for determining whether the user succeeds at the third progress gate.

16. The method according to one of the preceding examples, wherein: the second progress gate corresponds to a second task difficulty level; the third progress gate corresponds to a third task difficulty level; and the third task difficulty level is higher than the second task difficulty level.

17. The method according to one of the preceding examples, further comprising: determining a baseline performance of the user related to the set of assessment tasks; wherein the performance range is determined based at least in part on the baseline performance and the maximal performance of the user.

18. The method according to one of the preceding examples, wherein: the baseline performance is determined based at least in part on the user's performance of the set of assessment tasks in a distracting environment; and the maximal performance is determined based at least in part on the user's performance of the set of assessment tasks in an isolated environment.

19. The method according to one of the preceding examples, wherein: the baseline performance is determined based at least in part on the user's performance of the set of assessment tasks in a dual-task situation or a multi-task situation; and the maximal performance is determined based at least in part on the user's performance of the set of assessment tasks in a single-task situation.

20. The method according to one of the preceding examples, wherein the maximal performance is determined by an extension or an extrapolation based at least in part on the user's performance of the set of assessment tasks.

21. The method according to one of the preceding examples, wherein the maximal performance is determined by using data distributions from normative data curves or comparison data of individuals of a target population performing the set of assessment tasks.

22. The method according to one of the preceding examples, wherein the performing of the cognitive assessment of the user using the set of assessment tasks includes: presenting, through a user interface, the set of assessment tasks to the user; and collecting, through the user interface, the user's assessment responses to the set of assessment tasks.

23. The method according to one of the preceding examples, wherein: the first set of training tasks are presented to the user through a user interface; the user's first training responses to the first set of training tasks are collected through the user interface; the second set of training tasks are presented to the user through the user interface; and the user's second training responses to the second set of training tasks are collected through the user interface.

24. The method according to one of the preceding examples, wherein the user interface includes a touch-screen display.

25. The method according to one of the preceding examples, wherein the set of assessment tasks are performed by the user simultaneously.

26. The method according to one of the preceding examples, wherein the set of assessment tasks are performed by the user sequentially.

27. The method according to one of the preceding examples, wherein: the first set of training tasks are performed by the user simultaneously; and the second set of training tasks are performed by the user simultaneously.

28. The method according to one of the preceding examples, wherein: the first set of training tasks are performed by the user sequentially; and the second set of training tasks are performed by the user sequentially.

29. A method of operating a data processing system including one or more data processors and a non-transitory machine readable storage medium, the method comprising: performing, using the one or more data processors, an initial cognitive assessment of a user using a first set of assessment tasks; estimating, using the one or more data processors, an initial maximal performance of the user related to the first set of assessment tasks; determining, using the one or more data processors, the initial performance range based at least in part on the initial maximal performance of the user; dividing, using the one or more data processors, the initial performance range into a first plurality of progress gates, the first plurality of progress gates corresponding to a first plurality of task difficulty levels, data related to the initial performance range being stored in a first data structure in the non-transitory machine-readable storage medium; selecting, using the one or more data processors, a first progress gate within the initial performance range; generating, using the one or more data processors, a first set of training tasks associated with the first progress gate; collecting the user's first training responses to the first set of training tasks; determining, using the one or more data processors, whether the user succeeds at the first progress gate based at least in part on the user's first training responses. The method further includes: in response to the user succeeding at the first progress gate, performing, using the one or more data processors, a cognitive assessment of the user using a second set of assessment tasks; estimating, using the one or more data processors, an updated maximal performance of the user related to the second set of assessment tasks; determining, using the one or more data processors, an updated performance range based at least in part on the updated maximal performance of the user, data related to the updated performance range being stored in a second data structure in the non-transitory machine-readable storage medium; dividing, using the one or more data processors, the updated performance range into a second plurality of progress gates, the second plurality of progress gates corresponding to a second plurality of task difficulty levels; selecting, using the one or more data processors, a second progress gate within the updated performance range; generating, using the one or more data processors, a second set of training tasks associated with the second progress gate; and collecting the user's second training responses to the second set of training tasks for determining whether the user succeeds at the second progress gate.

30. The method according to one of the preceding examples, further comprising: determining a plurality of rewards; and associating the plurality of rewards with the first plurality of progress gates.

31. The method according to one of the preceding examples, further comprising: in response to the user succeeding at the first progress gate, presenting a first reward associated with the first progress gate to the user.

32. The method according to one of the preceding examples, further comprising: determining whether the user succeeds at the second progress gate based at least in part on the user's second training responses; and in response to the user succeeding at the second progress gate, presenting a second reward associated with the second progress gate to the user.

33. The method according to one of the preceding examples, wherein the plurality of rewards are dynamically determined and modified.

34. The method according to one of the preceding examples, further comprising: in response to the user performing a predetermined number of training tasks associated with the first progress gate, presenting a first reward associated with the first progress gate to the user.

35. The method according to one of the preceding examples, further comprising: in response to the user performing the first set of training tasks for a predetermined duration, presenting a first reward associated with the first progress gate to the user.

36. The method according to one of the preceding examples, further comprising: in response to the user advancing from the first progress gate to the second progress gate within a predetermined time period, presenting a first reward associated with the first progress gate to the user.

37. The method according to one of the preceding examples, wherein the plurality of rewards include indications associated with the plurality of progress gates.

38. The method according to one of the preceding examples, further comprising: determining a plurality of rewards; and associating the plurality of rewards with the second plurality of progress gates.

39. The method according to one of the preceding examples, wherein: the first progress gate corresponds to a first task difficulty level; the second progress gate corresponds to a second task difficulty level; and the second task difficulty level is higher than the first task difficulty level.

40. The method according to one of the preceding examples, further comprising: in response to the user not succeeding at the first progress gate, generating a third set of training tasks associated with the first progress gate; and collecting the user's third training responses to the third set of training tasks for further determining whether the user succeeds at the first progress gate.

41. The method according to one of the preceding examples, further comprising: determining whether the user succeeds at the second progress gate based at least in part on the user's second training responses; in response to the user succeeding at the second progress gate, performing a cognitive assessment of the user using a third set of assessment tasks; estimating a third maximal performance of the user related to the third set of assessment tasks; determining a third performance range based at least in part on the updated maximal performance of the user; dividing the third performance range into a third plurality of progress gates, the third plurality of progress gates corresponding to a third plurality of task difficulty levels; selecting a third progress gate within the third performance range; generating a third set of training tasks associated with the third progress gate; and collecting the user's third training responses to the third set of training tasks for determining whether the user succeeds at the third progress gate.

42. The method according to one of the preceding examples, wherein: the second progress gate corresponds to a second task difficulty level; the third progress gate corresponds to a third task difficulty level; and the third task difficulty level is higher than the second task difficulty level.

43. The method according to one of the preceding examples, further comprising: determining an initial baseline performance of the user related to the first set of assessment tasks; wherein the initial performance range is determined based at least in part on the initial baseline performance and the initial maximal performance of the user.

44. The method according to one of the preceding examples, wherein: the initial baseline performance is determined based at least in part on the user's performance of the first set of assessment tasks in a distracting environment; and the initial maximal performance is determined based at least in part on the user's performance of the first set of assessment tasks in an isolated environment.

45. The method according to one of the preceding examples, wherein: the initial baseline performance is determined based at least in part on the user's performance of the first set of assessment tasks in a dual-task situation or a multi-task situation; and the initial maximal performance is determined based at least in part on the user's performance of the first set of assessment tasks in a single-task situation.

46. The method according to one of the preceding examples, wherein the initial maximal performance is determined by an extension or an extrapolation based at least in part on the user's performance of the first set of assessment tasks.

47. The method according to one of the preceding examples, wherein the initial maximal performance is determined by using data distributions from normative data curves or comparison data of individuals of a target population performing the first set of assessment tasks.

48. The method according to one of the preceding examples, further comprising: determining an updated baseline performance of the user related to the second set of assessment tasks; wherein the updated performance range is determined based at least in part on the updated baseline performance and the updated maximal performance of the user.

49. The method according to one of the preceding examples, wherein the updated baseline performance is the same as the initial baseline performance.

50. The method according to one of the preceding examples, wherein the updated maximal performance is the same as the initial maximal performance.

51. The method according to one of the preceding examples, wherein the performing of the initial cognitive assessment of the user using the first set of assessment tasks includes: presenting, through a user interface, the first set of assessment tasks to the user; and collecting, through the user interface, the user's assessment responses to the first set of assessment tasks.

52. The method according to one of the preceding examples, wherein: the first set of training tasks are presented to the user through a user interface; the user's first training responses to the first set of training tasks are collected through the user interface; the second set of training tasks are presented to the user through the user interface; and the user's second training responses to the second set of training tasks are collected through the user interface.

53. The method according to one of the preceding examples, wherein: the first set of training tasks are performed by the user simultaneously; and the second set of training tasks are performed by the user simultaneously.

54. The method according to one of the preceding examples, wherein: the first set of training tasks are performed by the user sequentially; and the second set of training tasks are performed by the user sequentially.

55. The method according to one of the preceding examples, further comprising: selecting, using the one or more data processors, a third progress gate within the initial performance range, prior to the selection of the first progress gate; generating, using the one or more data processors, a third set of training tasks associated with the third progress gate; collecting the user's third training responses to the third set of training tasks; and determining, using the one or more data processors, whether the user succeeds at the third progress gate based at least in part on the user's third training responses; wherein the first progress gate within the initial performance range is selected in response to the user succeeding at the third progress gate.

56. The method according to one of the preceding examples, further comprising: selecting, using the one or more data processors, a third progress gate within the initial performance range, prior to the selection of the first progress gate; generating, using the one or more data processors, a third set of training tasks associated with the third progress gate; collecting the user's third training responses to the third set of training tasks; and determining, using the one or more data processors, whether the user succeeds at the third progress gate based at least in part on the user's third training responses; wherein the first progress gate within the initial performance range is selected in response to the user succeeding at the third progress gate.

57. Device for a diagnostic system for enhancing a cognitive ability in a subject in need thereof, wherein said device is configured to perform the method according to one of the preceding examples.

58. The device according to example 57, wherein the subject's cognitive ability is assessed by a cognitive ability test, wherein the cognitive ability test is selected from the group consisting of Mini Mental State Exam, CANTAB cognitive battery, Repeatable Battery for the Assessment of Neuropsychological Status, Clinical Global Impression scales, Clinician's interview-Based Impression of Change, Severe Impairment Battery, Alzheimer's Disease Assessment Scale, Positive and Negative Syndrome Scale, Schizophrenia Cognition Rating Scale, Conners Adult ADHD Rating Scales, Hamilton Rating Scale for Depression, Hamilton Anxiety Scale, Montgomery-Asberg Depressing Rating scale, Young Mania Rating Scale, Children's Depression Rating Scale, Penn State Worry Questionnaire, Hospital Anxiety and Depression Scale, Aberrant Behavior Checklist, Activities of Daily Living scales, General Practitioner Assessment of Cognition, Eriksen Flanker Task, Stroop Task, Intelligence quotient, Raven's Progressive Matrices, Behavior Rating Inventory of Executive Function (BRIEF), Test of Everyday Attention (and Test of Everyday Attention for Children), Test of Memory and Learning, Wisconsin Card Scoring Test, and Delis Kaplan Executive Function System.

59. The device according to one of the preceding examples, wherein the subject's cognitive ability is enhanced as indicated by a score improvement in a cognitive ability test, wherein the cognitive ability test is selected from the group consisting of Mini Mental State Exam, CANTAB cognitive battery, Repeatable Battery for the Assessment of Neuropsychological Status, Clinical Global Impression scales, Clinician's interview-Based Impression of Change, Severe Impairment Battery, Alzheimer's Disease Assessment Scale, Positive and Negative Syndrome Scale, Schizophrenia Cognition Rating Scale, Conners Adult ADHD Rating Scales, Hamilton Rating Scale for Depression, Hamilton Anxiety Scale, Montgomery-Asberg Depressing Rating scale, Young Mania Rating Scale, Children's Depression Rating Scale, Penn State Worry Questionnaire, Hospital Anxiety and Depression Scale, Aberrant Behavior Checklist, Activities of Daily Living scales, General Practitioner Assessment of Cognition, Eriksen Flanker Task, Stroop Task, Intelligence quotient, Raven's Progressive Matrices, Behavior Rating Inventory of Executive Function (BRIEF), Test of Everyday Attention (and Test of Everyday Attention for Children), Test of Memory and Learning, Wisconsin Card Scoring Test, and Delis Kaplan Executive Function System.

60. The device according to one of the preceding examples, wherein the subject's cognitive ability is assessed by pre-training and post-training physiological tests that measure internal markers of disease or health such as detection of amyloid beta, cortisol and other stress response markers; and brain imaging studies that assess a condition based on presence of specific neural signatures.

61. The device according to one of the preceding examples, wherein the subject suffers from age-related cognitive decline, mild cognitive impairment, Alzheimer's disease, Parkinson's disease, Huntington's disease, depression, schizophrenia, dementia, Pick's disease, cognitive deficit associated with fatigue, multiple sclerosis, post traumatic stress disorder, obsessive-compulsive disorder, brain damage, anxiety, stress, panic, depression, dysphoria, malaise, attention deficit disorder, Autism Spectrum Disorder, chronic neurological illnesses or chronic psychiatric illnesses.

62. Device for a diagnostic system for monitoring a treatment of a disease that results in impaired cognition in a subject, said device being configured to: (i) perform the method according to one of the preceding examples to obtain a first set of performance data; (ii) administer to the subject a treatment for said disease for a period of time; (iii) after the period of time, perform the method according to one of the preceding examples to obtain a second set of performance data; (iv) compare first set of performance data and the second set of performance data; and (v) adjust the treatment for said disease in the subject.

The above only describes several scenarios presented by this invention, and the description is relatively specific and detailed, yet it cannot therefore be understood as limiting the scope of this invention's patent. It should be noted that ordinary persons skilled in the art may also, without deviating from the invention's conceptual premises, make a number of variations and modifications, which are all within the scope of this invention. As a result, in terms of protection, the patent claims shall prevail.

For example, some or all components of various embodiments or examples in the present disclosure each are, individually and/or in combination with at least another component, implemented using one or more software components, one or more hardware components, and/or one or more combinations of software and hardware components. In another example, some or all components of various embodiments or examples in the present disclosure each are, individually and/or in combination with at least another component, implemented in one or more circuits, such as one or more analog circuits and/or one or more digital circuits. In yet another example, various embodiments or examples in the present disclosure can be combined.

Additionally, the methods and systems described herein may be implemented on many different types of processing devices by program code comprising program instructions that are executable by the device processing subsystem. The software program instructions may include source code, object code, machine code, or any other stored data that is operable to cause a processing system to perform the methods and operations described herein. Other implementations may also be used, however, such as firmware or even appropriately designed hardware configured to perform the methods and systems described herein.

The systems' and methods' data (e.g., associations, mappings, data input, data output, intermediate data results, final data results, etc.) may be stored and implemented in one or more different types of computer-implemented data stores, such as different types of storage devices and programming constructs (e.g., RAM, ROM, Flash memory, flat files, databases, programming data structures, programming variables, IF-THEN (or similar type) statement constructs, etc.). It is noted that data structures describe formats for use in organizing and storing data in databases, programs, memory, or other computer-readable media for use by a computer program. The systems and methods may be provided on many different types of computer-readable media (e.g., non-transitory storage media), including computer storage mechanisms (e.g., CD-ROM, diskette, RAM, flash memory, computer's hard drive, etc.) that contain instructions (e.g., software) for use in execution by a processor to perform the methods' operations and implement the systems described herein.

The computer components, software modules, functions, data stores and data structures described herein may be connected directly or indirectly to each other in order to allow the flow of data needed for their operations. It is also noted that a module or processor includes but is not limited to a unit of code that performs a software operation, and can be implemented for example as a subroutine unit of code, or as a software function unit of code, or as an object (as in an object-oriented paradigm), or as an applet, or in a computer script language, or as another type of computer code. The software components and/or functionality may be located on a single computer or distributed across multiple computers depending upon the situation at hand. The computing system can include client devices and servers. A client device and server are generally remote from each other and typically interact through a communication network. The relationship of client device and server arises by virtue of computer programs running on the respective computers and having a client device-server relationship to each other.

While this specification contains many specifics, these should not be construed as limitations on the scope or of what may be claimed, but rather as descriptions of features specific to particular embodiments. Certain features that are described in this specification in the context or separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

Although specific embodiments of the present invention have been described, it will be understood by those of skill in the art that there are other embodiments that are equivalent to the described embodiments. Accordingly, it is to be understood that the invention is not to be limited by the specific illustrated embodiments, but only by the scope of the appended claims.

What is claimed is:

1. A processor-implemented method for enhancing cognitive abilities of a user by personalizing a cognitive training regimen through difficulty progression, the method comprising:

performing, using one or more data processors, a cognitive assessment of a user using a set of assessment tasks;

estimating, using the one or more data processors, a maximal performance of the user related to the set of assessment tasks;

determining, using the one or more data processors, a performance range based at least in part on the maximal performance of the user;

dividing, using the one or more data processors, the performance range into a plurality of progress gates, the plurality of progress gates corresponding to a plurality of task difficulty levels that the user may perform to progress within the training regimen, data related to the performance range being stored in a data structure in a non-transitory machine-readable storage medium;

selecting, using the one or more data processors, a first progress gate within the performance range;

generating, using the one or more data processors, a first set of training tasks associated with the first progress gate;

collecting the user's first training responses to the first set of training tasks;

determining, using the one or more data processors, whether the user succeeds at the first progress gate based at least in part on the user's first training responses; and in response to the user succeeding at the first progress gate,
  selecting, using the one or more data processors, a second progress gate within the performance range;
  generating, using the one or more data processors, a second set of training tasks associated with the second progress gate; and
  collecting the user's second training responses to the second set of training tasks for determining whether the user succeeds at the second progress gate,
  wherein (i) the plurality of task difficulty levels are within a range personalized for the user, and (ii)

difficulties of the generated first and second sets of training tasks are within the personalized range of task difficulty levels.

2. The method of claim 1, further comprising:
determining a plurality of rewards; and
associating the plurality of rewards with the plurality of progress gates.

3. The method of claim 2, further comprising:
in response to the user succeeding at the first progress gate, presenting a first reward associated with the first progress gate to the user.

4. The method of claim 2, further comprising:
in response to the user performing the first set of training tasks for a predetermined duration, presenting a first reward associated with the first progress gate to the user.

5. The method of claim 1, wherein:
the first progress gate corresponds to a first task difficulty level;
the second progress gate corresponds to a second task difficulty level; and
the second task difficulty level is higher than the first task difficulty level.

6. The method of claim 5, further comprising:
in response to the user not succeeding at the first progress gate for a predetermined duration,
determining a third task difficulty level to be associated with the second progress gate, the third task difficulty level being lower than the second task difficulty level;
generating a third set of training tasks according to the third task difficulty level; and
collecting the user's third training responses to the third set of training tasks for determining whether the user succeeds at the second progress gate.

7. The method of claim 1, further comprising:
in response to the user not succeeding at the first progress gate,
generating a third set of training tasks associated with the first progress gate; and
collecting the user's third training responses to the third set of training tasks for further determining whether the user succeeds at the first progress gate.

8. The method of claim 1, further comprising:
determining whether the user succeeds at the second progress gate based at least in part on the user's second training responses;
in response to the user succeeding at the second progress gate,
selecting, using the one or more data processors, a third progress gate within the performance range;
generating, using the one or more data processors, a third set of training tasks associated with the third progress gate; and
collecting the user's third training responses to the third set of training tasks for determining whether the user succeeds at the third progress gate.

9. The method of claim 1, further comprising:
determining a baseline performance of the user related to the set of assessment tasks;
wherein the performance range is determined based at least in part on the baseline performance and the maximal performance of the user.

10. The method of claim 9, wherein:
the baseline performance is determined based at least in part on the user's performance of the set of assessment tasks in a distracting environment; and
the maximal performance is determined based at least in part on the user's performance of the set of assessment tasks in an isolated environment.

11. The method of claim 9, wherein:
the baseline performance is determined based at least in part on the user's performance of the set of assessment tasks in a dual-task situation or a multi-task situation; and
the maximal performance is determined based at least in part on the user's performance of the set of assessment tasks in a single-task situation.

12. The method of claim 1, wherein the maximal performance is determined by an extension or an extrapolation based at least in part on the user's performance of the set of assessment tasks.

13. The method of claim 1, wherein the maximal performance is determined by using data distributions from normative data curves or comparison data of individuals of a target population performing the set of assessment tasks.

14. The method of claim 1, wherein:
the first set of training tasks are presented to the user through a user interface;
the user's first training responses to the first set of training tasks are collected through the user interface;
the second set of training tasks are presented to the user through the user interface; and
the user's second training responses to the second set of training tasks are collected through the user interface.

15. A processor-implemented method for enhancing cognitive abilities of a user by personalizing a cognitive training regimen through difficulty progression, the method comprising:
performing, using one or more data processors, an initial cognitive assessment of a user using a first set of assessment tasks;
estimating, using the one or more data processors, an initial maximal performance of the user related to the first set of assessment tasks;
determining, using the one or more data processors, the initial performance range based at least in part on the initial maximal performance of the user;
dividing, using the one or more data processors, the initial performance range into a first plurality of progress gates, the first plurality of progress gates corresponding to a first plurality of task difficulty levels that the user may perform to progress within the training regimen, data related to the initial performance range being stored in a first data structure in a non-transitory machine-readable storage medium;
selecting, using the one or more data processors, a first progress gate within the initial performance range;
generating, using the one or more data processors, a first set of training tasks associated with the first progress gate;
collecting the user's first training responses to the first set of training tasks;
determining, using the one or more data processors, whether the user succeeds at the first progress gate based at least in part on the user's first training responses; and
in response to the user succeeding at the first progress gate,
performing, using the one or more data processors, a cognitive assessment of the user using a second set of assessment tasks;

estimating, using the one or more data processors, an updated maximal performance of the user related to the second set of assessment tasks;

determining, using the one or more data processors, an updated performance range based at least in part on the updated maximal performance of the user, data related to the updated performance range being stored in a second data structure in the non-transitory machine-readable storage medium;

dividing, using the one or more data processors, the updated performance range into a second plurality of progress gates, the second plurality of progress gates corresponding to a second plurality of task difficulty levels;

selecting, using the one or more data processors, a second progress gate within the updated performance range;

generating, using the one or more data processors, a second set of training tasks associated with the second progress gate; and collecting the user's second training responses to the second set of training tasks for determining whether the user succeeds at the second progress gate, wherein (i) each of the first and second pluralities of task difficulty levels are within a range personalized for the user, and (ii) difficulties of the generated first and second sets of training tasks are within the personalized range of task difficulty levels.

16. The method of claim 15, further comprising:
determining a plurality of rewards; and
associating the plurality of rewards with the first plurality of progress gates.

17. The method of claim 16, further comprising: in response to the user succeeding at the first progress gate, presenting a first reward associated with the first progress gate to the user.

18. The method of claim 16, further comprising: in response to the user performing a predetermined number of training tasks associated with the first progress gate, presenting a first reward associated with the first progress gate to the user.

19. The method of claim 16, further comprising: in response to the user performing the first set of training tasks for a predetermined duration, presenting a first reward associated with the first progress gate to the user.

20. The method of claim 16, further comprising: in response to the user advancing from the first progress gate to the second progress gate within a predetermined time period, presenting a first reward associated with the first progress gate to the user.

21. The method of claim 15, further comprising:
determining a plurality of rewards; and
associating the plurality of rewards with the second plurality of progress gates.

22. The method of claim 15, wherein:
the first progress gate corresponds to a first task difficulty level;
the second progress gate corresponds to a second task difficulty level; and
the second task difficulty level is higher than the first task difficulty level.

23. The method of claim 15, further comprising:
in response to the user not succeeding at the first progress gate,
generating a third set of training tasks associated with the first progress gate; and
collecting the user's third training responses to the third set of training tasks for further determining whether the user succeeds at the first progress gate.

24. The method of claim 15, further comprising:
determining whether the user succeeds at the second progress gate based at least in part on the user's second training responses;
in response to the user succeeding at the second progress gate,
performing a cognitive assessment of the user using a third set of assessment tasks;
estimating a third maximal performance of the user related to the third set of assessment tasks;
determining a third performance range based at least in part on the updated maximal performance of the user;
dividing the third performance range into a third plurality of progress gates, the third plurality of progress gates corresponding to a third plurality of task difficulty levels;
selecting a third progress gate within the third performance range;
generating a third set of training tasks associated with the third progress gate; and
collecting the user's third training responses to the third set of training tasks for determining whether the user succeeds at the third progress gate.

25. The method of claim 15, further comprising:
determining an initial baseline performance of the user related to the first set of assessment tasks;
wherein the initial performance range is determined based at least in part on the initial baseline performance and the initial maximal performance of the user.

26. The method of claim 25, wherein:
the initial baseline performance is determined based at least in part on the user's performance of the first set of assessment tasks in a distracting environment; and
the initial maximal performance is determined based at least in part on the user's performance of the first set of assessment tasks in an isolated environment.

27. The method of claim 25, wherein:
the initial baseline performance is determined based at least in part on the user's performance of the first set of assessment tasks in a dual-task situation or a multi-task situation; and
the initial maximal performance is determined based at least in part on the user's performance of the first set of assessment tasks in a single-task situation.

28. The method of claim 15, wherein the initial maximal performance is determined by an extension or an extrapolation based at least in part on the user's performance of the first set of assessment tasks.

29. The method of claim 15, wherein the initial maximal performance is determined by using data distributions from normative data curves or comparison data of individuals of a target population performing the first set of assessment tasks.

30. The method of claim 15, further comprising:
selecting, using the one or more data processors, a third progress gate within the initial performance range, prior to the selection of the first progress gate;
generating, using the one or more data processors, a third set of training tasks associated with the third progress gate;
collecting the user's third training responses to the third set of training tasks; and determining, using the one or more data processors, whether the user succeeds at the third progress gate based at least in part on the user's third training responses;
wherein the first progress gate within the initial performance range is selected in response to the user succeeding at the third progress gate.

31. A processor-implemented system for enhancing cognitive abilities of a user by personalizing a cognitive training regimen through difficulty progression, the system comprising:
one or more processors configured to:
perform a cognitive assessment of a user using a set of assessment tasks;
estimate a maximal performance of the user related to the set of assessment tasks;
determine a performance range based at least in part on the maximal performance of the user;
divide the performance range into a plurality of progress gates, the plurality of progress gates corresponding to a plurality of task difficulty levels that the user may perform to progress within the training regimen;
select a first progress gate within the performance range;
generate a first set of training tasks associated with the first progress gate;
collect the user's first training responses to the first set of training tasks;
determine whether the user succeeds at the first progress gate based at least in part on the user's first training responses; and
in response to the user succeeding at the first progress gate,
select a second progress gate within the performance range;
generate a second set of training tasks associated with the second progress gate; and
collect the user's second training responses to the second set of training tasks to determine whether the user succeeds at the second progress gate; and
one or more non-transitory machine-readable storage media configured to store data related to the first set of training tasks, data related to the second set of training tasks, and data related to the performance range,
wherein (i) the plurality of task difficulty levels are within a range personalized for the user, and (ii) difficulties of the generated first and second sets of training tasks are within the personalized range of task difficulty levels.

32. A processor-implemented system for enhancing cognitive abilities of a user by personalizing a cognitive training regimen through difficulty progression, the system comprising:
one or more processors configured to:
perform an initial cognitive assessment of a user using a first set of assessment tasks;
estimate an initial maximal performance of the user related to the first set of assessment tasks;
determine the initial performance range based at least in part on the initial maximal performance of the user;
divide the initial performance range into a first plurality of progress gates, the first plurality of progress gates corresponding to a first plurality of task difficulty levels that the user may perform to progress within the training regimen;
select a first progress gate within the initial performance range;
generate a first set of training tasks associated with the first progress gate;
collect the user's first training responses to the first set of training tasks;
determine whether the user succeeds at the first progress gate based at least in part on the user's first training responses; and
in response to the user succeeding at the first progress gate,
perform a cognitive assessment of the user using a second set of assessment tasks;
estimate an updated maximal performance of the user related to the second set of assessment tasks;
determine an updated performance range based at least in part on the updated maximal performance of the user;
divide the updated performance range into a second plurality of progress gates, the second plurality of progress gates corresponding to a second plurality of task difficulty levels that the user may perform to progress within the training regimen;
select a second progress gate within the updated performance range;
generate a second set of training tasks associated with the second progress gate; and
collect the user's second training responses to the second set of training tasks to determine whether the user succeeds at the second progress gate; and
one or more non-transitory machine-readable storage media configured to store data related to the first set of training tasks, data related to the second set of training tasks, date related to the initial performance range, and data related to the updated performance range,
wherein (i) the first and second pluralities of task difficulty levels are within a range personalized for the user, and (ii) difficulties of the generated first and second sets of training tasks are within the personalized range of task difficulty levels.

33. A non-transitory computer-readable medium encoded with instructions for commanding one or more processors to execute operations of a method for enhancing cognitive abilities of a user by personalizing a cognitive training regimen through difficulty progression, the method comprising:
performing a cognitive assessment of a user using a set of assessment tasks;
estimating a maximal performance of the user related to the set of assessment tasks;
determining a performance range based at least in part on the maximal performance of the user;
dividing the performance range into a plurality of progress gates, the plurality of progress gates corresponding to a plurality of task difficulty levels that the user may perform to progress within the training regimen;
selecting a first progress gate within the performance range;
generating a first set of training tasks associated with the first progress gate;
collecting the user's first training responses to the first set of training tasks;
determining whether the user succeeds at the first progress gate based at least in part on the user's first training responses; and
in response to the user succeeding at the first progress gate,
selecting a second progress gate within the performance range;

generating a second set of training tasks associated with the second progress gate; and collecting the user's second training responses to the second set of training tasks for determining whether the user succeeds at the second progress gate, wherein (i) the plurality of task difficulty levels are within a range personalized for the user, and (ii) difficulties of the generated first and second sets of training tasks are within the personalized range of task difficulty levels.

34. A non-transitory computer-readable medium encoded with instructions for commanding one or more processors to execute operations of a method for enhancing cognitive abilities of a user by personalizing a cognitive training regimen through difficulty progression, the method comprising:

performing an initial cognitive assessment of a user using a first set of assessment tasks;

estimating an initial maximal performance of the user related to the first set of assessment tasks;

determining the initial performance range based at least in part on the initial maximal performance of the user;

dividing the initial performance range into a first plurality of progress gates, the first plurality of progress gates corresponding to a first plurality of task difficulty levels that the user may perform to progress within the training regimen;

selecting a first progress gate within the initial performance range;

generating a first set of training tasks associated with the first progress gate;

collecting the user's first training responses to the first set of training tasks;

determining whether the user succeeds at the first progress gate based at least in part on the user's first training responses; and in response to the user succeeding at the first progress gate, performing a cognitive assessment of the user using a second set of assessment tasks;

estimating an updated maximal performance of the user related to the second set of assessment tasks;

determining an updated performance range based at least in part on the updated maximal performance of the user;

dividing the updated performance range into a second plurality of progress gates, the second plurality of progress gates corresponding to a second plurality of task difficulty levels that the user may perform to progress within the training regimen;

selecting a second progress gate within the updated performance range;

generating a second set of training tasks associated with the second progress gate; and collecting the user's second training responses to the second set of training tasks for determining whether the user succeeds at the second progress gate, wherein (i) the first and second pluralities of task difficulty levels are within a range personalized for the user, and (ii) difficulties of the generated first and second sets of training tasks are within the personalized range of task difficulty levels.

35. A method for enhancing a cognitive ability in a subject in need thereof, wherein said method comprises performing by the subject the processor-implemented method of any one of claims 1 to 30.

36. The method of claim 35, wherein the subject's cognitive ability is assessed by a cognitive ability test, wherein the cognitive ability test is selected from the group consisting of Mini Mental State Exam, CANTAB cognitive battery, Repeatable Battery for the Assessment of Neuropsychological Status, Clinical Global Impression scales, Clinician's interview-Based Impression of Change, Severe Impairment Battery, Alzheimer's Disease Assessment Scale, Positive and Negative Syndrome Scale, Schizophrenia Cognition Rating Scale, Conners Adult ADHD Rating Scales, Hamilton Rating Scale for Depression, Hamilton Anxiety Scale, Montgomery-Asberg Depressing Rating scale, Young Mania Rating Scale, Children's Depression Rating Scale, Penn State Worry Questionnaire, Hospital Anxiety and Depression Scale, Aberrant Behavior Checklist, Activities of Daily Living scales, General Practitioner Assessment of Cognition, Eriksen Flanker Task, Stroop Task, Intelligence quotient, Raven's Progressive Matrices, Behavior Rating Inventory of Executive Function (BRIEF), Test of Everyday Attention (and Test of Everyday Attention for Children), Test of Memory and Learning, Wisconsin Card Scoring Test, and Delis Kaplan Executive Function System.

37. The method of claim 35, wherein the subject's cognitive ability is enhanced as indicated by a score improvement in a cognitive ability test, wherein the cognitive ability test is selected from the group consisting of Mini Mental State Exam, CANTAB cognitive battery, Repeatable Battery for the Assessment of Neuropsychological Status, Clinical Global Impression scales, Clinician's interview-Based Impression of Change, Severe Impairment Battery, Alzheimer's Disease Assessment Scale, Positive and Negative Syndrome Scale, Schizophrenia Cognition Rating Scale, Conners Adult ADHD Rating Scales, Hamilton Rating Scale for Depression, Hamilton Anxiety Scale, Montgomery-Asberg Depressing Rating scale, Young Mania Rating Scale, Children's Depression Rating Scale, Penn State Worry Questionnaire, Hospital Anxiety and Depression Scale, Aberrant Behavior Checklist, Activities of Daily Living scales, General Practitioner Assessment of Cognition, Eriksen Flanker Task, Stroop Task, Intelligence quotient, Raven's Progressive Matrices, Behavior Rating Inventory of Executive Function (BRIEF), Test of Everyday Attention (and Test of Everyday Attention for Children), Test of Memory and Learning, Wisconsin Card Scoring Test, and Delis Kaplan Executive Function System.

38. The method of claim 35, wherein the subject's cognitive ability is assessed by pre-training and post-training physiological tests that measure internal markers of disease or health such as detection of amyloid beta, cortisol and other stress response markers; and brain imaging studies that assess a condition based on presence of specific neural signatures.

39. The method of claim 35, wherein the subject suffers from age-related cognitive decline, mild cognitive impairment, Alzheimer's disease, Parkinson's disease, Huntington's disease, depression, schizophrenia, dementia, Pick's disease, cognitive deficit associated with fatigue, multiple sclerosis, post traumatic stress disorder, obsessive-compulsive disorder, brain damage, anxiety, stress, panic, depression, dysphoria, malaise, attention deficit disorder, Autism Spectrum Disorder, chronic neurological illnesses or chronic psychiatric illnesses.

40. A method of monitoring a treatment of a disease that results in impaired cognition in a subject, said method comprising:

(i) performing by the subject the processor-implemented method of any one of claims 1 to 30 to obtain a first set of performance data;

(ii) administering to the subject a treatment for said disease for a period of time;
(iii) after the period of time, performing by the subject the processor-implemented method of any one of claims 1 to 30 to obtain a second set of performance data;
(iv) comparing first set of performance data and the second set of performance data; and
(v) adjusting the treatment for said disease in the subject.

* * * * *